(12) United States Patent
Barnea

(10) Patent No.: US 9,737,585 B2
(45) Date of Patent: Aug. 22, 2017

(54) COMPOSITIONS AND METHODS FOR TREATMENT OF INTRACELLULAR DAMAGE AND BACTERIAL INFECTION

(75) Inventor: Eytan R. Barnea, Cherry Hill, NJ (US)

(73) Assignee: BioIncept, LLC

( * ) Notice: Subject to any disclaimer, the term of this patent is extended or adjusted under 35 U.S.C. 154(b) by 235 days.

(21) Appl. No.: 14/009,505

(22) PCT Filed: Mar. 2, 2012

(86) PCT No.: PCT/US2012/027480
§ 371 (c)(1),
(2), (4) Date: Feb. 13, 2014

(87) PCT Pub. No.: WO2012/119072
PCT Pub. Date: Sep. 7, 2012

(65) Prior Publication Data
US 2014/0147414 A1    May 29, 2014

Related U.S. Application Data

(60) Provisional application No. 61/448,446, filed on Mar. 2, 2011.

(51) Int. Cl.
*A61K 38/00* (2006.01)
*A61K 38/21* (2006.01)
*A61K 38/10* (2006.01)
*A61K 38/08* (2006.01)

(52) U.S. Cl.
CPC .............. *A61K 38/08* (2013.01); *A61K 38/10* (2013.01); *A61K 38/217* (2013.01)

(58) Field of Classification Search
None
See application file for complete search history.

(56) References Cited

U.S. PATENT DOCUMENTS

| 5,279,941 | A | 1/1994 | Lessey |
| 5,393,534 | A | 2/1995 | Cavanaugh et al. |
| 5,646,003 | A | 7/1997 | Barnea et al. |
| 5,648,340 | A | 7/1997 | Barnea |
| 5,658,792 | A | 8/1997 | Nuell et al. |
| 5,665,355 | A | 9/1997 | Primi |
| 5,981,198 | A | 11/1999 | Barnea et al. |
| 6,171,591 | B1 | 1/2001 | Hall |
| 6,225,097 | B1 | 5/2001 | Obata et al. |
| 6,365,727 | B1 | 4/2002 | Yoon et al. |
| 6,585,979 | B1 | 7/2003 | Berman |
| 7,273,708 | B2 | 9/2007 | Barnea et al. |
| 7,670,850 | B2 | 3/2010 | Barnea et al. |
| 7,670,851 | B2 | 3/2010 | Barnea et al. |
| 7,670,852 | B2 | 3/2010 | Barnea et al. |
| 7,678,582 | B2 | 3/2010 | Barnea et al. |
| 7,695,977 | B2 | 4/2010 | Barnea et al. |
| 7,723,289 | B2 | 5/2010 | Barnea |
| 7,723,290 | B2 | 5/2010 | Barnea |
| 8,454,967 | B2 | 6/2013 | Barnea |
| 9,097,725 | B2 | 8/2015 | Barnea |
| 2002/0004205 | A1 | 1/2002 | Consler et al. |
| 2003/0099643 | A1 | 5/2003 | June et al. |
| 2003/0109690 | A1 | 6/2003 | Ruben et al. |
| 2003/0203410 | A1 | 10/2003 | Barnea et al. |
| 2005/0064520 | A1 | 3/2005 | Barnea et al. |
| 2007/0231310 | A1 | 10/2007 | Friedlander et al. |
| 2008/0003178 | A1 | 1/2008 | Barnea |
| 2008/0227778 | A1* | 9/2008 | Dinsmore ............. C04B 35/632 514/235.2 |
| 2008/0269137 | A1* | 10/2008 | Barnea ............... G01N 33/6854 514/6.9 |
| 2008/0293149 | A1 | 11/2008 | Barnea et al. |
| 2008/0299677 | A1 | 12/2008 | Barnea et al. |
| 2008/0305468 | A1 | 12/2008 | Barnea et al. |

(Continued)

FOREIGN PATENT DOCUMENTS

| CA | 2490538 A1 | 1/2003 |
| DE | 4400640 A1 | 7/1995 |

(Continued)

OTHER PUBLICATIONS

Kraus TA et al., Oral Tolerance and Inflammatory Bowel Disease, Cuff Opin in Gastroenterol, 2005, 21(6):692-696.
Lederman MM et al., Defective suppressor cell generation in juvenile onset diabetes, J Immunol, 1981, 127 (5):2051-2055.
Li J et al., Both corepressor proteins SMRT and N-CoR exist in large protein complexes containing HDAC3, EMBO J, 2000, 19(16):4342-4350.
Liu JO, The yins of T cell activation, Sci STKE, 2005, (265):re1.
Loke YW et al., Immunology of Implantation, Ballieres Best Pract ResClin Obstet Gynecol, 2000, 14(5):827-837.
Margolis RL et al., cDNAs with long CAG trinucleotide repeats from human brain, Hum Genet, 1997, 100(1):114-122.
Marketletter, AutoImmune shares collapse on Colloral data in rheumatoid arthritis, Marketletter Publications Ltd. (Sep. 13, 1999), 2 pp.
Mashima K et al., Multiple forms of growth inhibitors secreted from cultured rat liver cells: purification and characterization, J Biochem, 1988, 103(6):1020-1026.

(Continued)

*Primary Examiner* — Christine J Saoud
*Assistant Examiner* — Jegatheesan Seharaseyon
(74) *Attorney, Agent, or Firm* — John A. Zurawski, Esq.

(57) ABSTRACT

Pre-implantation factor (PIF) may be used to treat intracellular damage. Aspects of the invention are directed to a method of treating intracellular damage comprising administering PIF to a subject in need thereof. Some aspects may be directed to methods of increasing cytokine secretion in response to intracellular damage comprising administering PIF to a subject in need thereof. The intracellular damage may be a result of a disease such as *Listeria monocytogenes* infection, malaria, Lyme disease, cardiovascular disease, duodenal peptic ulcer, atherosclerosis, peritonitis or tuberculosis. In some aspects, a method of treating tuberculosis is disclosed, comprising administering PIF to a subject in need thereof. In some aspects, a method of treating atherosclerosis is disclosed, comprising administering PIF to a subject in need thereof. In some aspects, a method of treating peritonitis is disclosed, comprising administering PIF to a subject in need thereof.

13 Claims, 36 Drawing Sheets

(56) References Cited

U.S. PATENT DOCUMENTS

| | | |
|---|---|---|
| 2008/0305552 A1 | 12/2008 | Barnea et al. |
| 2009/0011427 A1 | 1/2009 | Barnea et al. |
| 2009/0081225 A1 | 3/2009 | Barnea |
| 2010/0197040 A1 | 8/2010 | Barnea et al. |
| 2011/0112016 A1 | 5/2011 | Barnea |
| 2012/0107318 A9 | 5/2012 | Barnea |
| 2012/0301921 A1 | 11/2012 | Williams et al. |

FOREIGN PATENT DOCUMENTS

| | | |
|---|---|---|
| EP | 1404877 A2 | 4/2004 |
| JP | 4593106 B2 | 12/2010 |
| MX | 277034 | 7/2010 |
| WO | 9209294 A1 | 6/1992 |
| WO | 9406464 A1 | 3/1994 |
| WO | 9526982 A2 | 10/1995 |
| WO | 9709418 A1 | 3/1997 |
| WO | 9852550 A1 | 11/1998 |
| WO | 0001402 A1 | 1/2000 |
| WO | 0240717 A2 | 5/2002 |
| WO | 02053092 A2 | 7/2002 |
| WO | WO03/004601 | 1/2003 |
| WO | 2004053086 A2 | 6/2004 |
| WO | WO2005/030791 | 4/2005 |
| WO | 2005040196 A2 | 5/2005 |
| WO | 2006113898 A2 | 10/2006 |
| WO | 2012119072 A2 | 9/2012 |

OTHER PUBLICATIONS

Matsuyama K et al., Purification of three antibacterial proteins from the culture medium of NIH-Sape-4, an embryonic cell line of Sarcophaga peregrina, J Biol Chem, 1988, 263(32):17112-17116.

Mattson R et al., Placental MCH class I antigen expression is induced in mice following in vivo treatment with recombinant interferon gamma, J Reprod Immunol, 1991, 19(2):115-129.

May 1988, "Infertility. Medical and Social Choices" U.S. Congress, Office of Technology Assessment. DTA BA 358. U.S. Government Printing Office, Washington, D.C.

McFarland HF, Correlation between MR and clinical findings of disease activity in multiple sclerosis, AJNR Am J Neuroradiol, 1999, 20(10):1777-1778.

McGuirk P et al., Pathogen-specific regulatory T cells provoke a shift in the Th1/Th2 paradigm in immunity to infectious diseases, Trends Immunol, 2002, 23(9):450-455.

Medrano L et al., Sequence Analysis of the polymerase domain of HIV-1 reverse transcriptase in naive and zidovudine-treated individuals reveals a higher polymorphism in alpha-helices as compared with beta-strands, Virus Genes, 1999,18(3):203-210.

Mellor AL et al., Extinguishing maternal immune responses during pregnancy: implications for immunosuppression, Semin Immunol, 2001, 13(4):213-218.

Mielcarek M et al., Graft-vs-host disease after non-myeloablative hematopoietic cell transplantation, Leuk Lymphoma, 2005, 46(9):1251-1260.

Miller DH et al., A controlled trial of natalizumab for relapsing multiple sclerosis, N Engl J Med, 2003, 348(1):15-23.

Minhas BS et al., Platelet activating factor and conception, Am J Reprod Immunol, 1996, 35(3):267-271.

Mirhashemi, (Barnea et al. eds), Cancer and Pregnancy, 2002, New England J. of Med. Book Review 346(24): 1921.

Mirhashemi, Cancer and Pregnancy, Edited by Eytan R. Barnea, Eric Jaunlaux, and Peter E. Schwartz, The New England Journal of Medicine Book Review (Jun. 13, 2002), 346(24):1921-1922.

Mocellin S et al., The dual role of IL-10, Trends Immunol, 2003, 24(1):36-43.

Moffett-King A, Natural killer cells and pregnancy, Nat Rev Immunol, 2002 2(9):656-663.

Morgan, et al., Approaches to the Discovery of Non-Peptide Ligands for Peptide Receptors and Peptidases, Annual Report in Medicinal Chemistry (1989), 24(VI): 243-252.

Morton H et al., An early pregnancy factor detected in human serum by the rosette inhibition test, Lancet, 1977, 1 (8008)394-397.

Morton H et al., Studies of the rosette inhibition test in pregnant mice: evidence of immunosuppression?, Proc R Soc Lond B Biol Sci, 1976, 193(1113):413-419.

Nahhas F et al., Human embryonic origin early pregnancy factor before and after implantation, Am J Reprod Immunol, 1990, 22(3-4):105-108.

Nahhas, et al., Early Pregnancy Factor (EPF) Determination in Pregnant and IVF/ET Patients, and in Human Embryo Cultures, American Fertility Society 15.sup.th Ann. Mtg., San Francisco, CA (1989), pp. S53-S54 (Abstract O-130).

Navot D et al., Poor oocyte quality rather than implantation failure as a cause of age-related decline female fertility, Lancet, 1991, 337(8754):1375-1377.

O'Neill C et al., Use of a bioassay for embryo-derived platelet activating factor as a means of assessing quality and pregnancy potential of human embryos, Fertil Steril, 1987, 47(6):969-975.

O'Neill C, Partial characterization of the embryo-derived platelet-activating factor in mice, J Reprod Fertil, 1985, 75 (2):375-380.

O'Neill C, Thrombocytopenia is an initial maternal response to fertilization in the mouse, J Reprod Fertil, 1985, 73 (2):559-566.

Olsen JV et al., Global, in vivo, and site-specific phosphorylation dynamics in signaling networks, Cell, 2006, 127 (3):635-648.

Or R et al., The prophylactic potential of fludarabine monophosphate in graft-versus-host disease after bone marrow Transplantation in murine models, Bone Marrow Transplant, 2000, 25(3):263-266.

Ordentlich P et al., Unique forms of human and mouse nuclear receptor corepressor SMRT, Proc Natl Acad Sci USA, 1999, 96(6):2639-2644.

Paidas et al., Pregnancy Implantation Factor (PIF) activity is correlated with a pro-imflammatory response, 2002, 23.sup.rd Annual Society for Maternal-Fetal Medicine Conference, San Francisco, CA (abstract).

Paidas, et al., Preimplantation Factor (PIF) Upregulates First Trimester Toll Like Receptor-2, Supporting the Role of PIF as an Embryo Derived Factor Influencing Maternal Innate Immunity, 27.sup.th Annual Scientific Meeting of the Society forMaternal-Fetal Medicine, San Francisco, CA (Feb. 5-10, 2007), S140 (Abstract 448).

Park EJ et al., SMRTe, a silencing mediator for retinoid and thyroid hormone receptors-extended isoform that is more related to the nuclear receptor corepressor, Proc Natl Acad Sci USA, 1999, 96(7):3519-3524.

Piccinni MP et al., Production of IL-4 and leukemia inhibitory factor by T cells of the cumulus oophorus: a favorable microenvironment for pre-implantation embryo development, Eur J Immunol, 2001, 31(8):2431-2437.

Pinkas H et al., Immunesuppressive activity in culture media containing human oocytes fertilized in vitro, Arch Androl, 1992, 28(1):53-59.

Pozzilli P et al., No effect of oral insulin on residual beta-cell function in recent-onset type 1 diabetes (the IMDIAB VII). IMDIAB group, Diabetologia, 2000, 43(8):1000-1004.

Qin ZH et al., Detection of early pregnancy factor in human sera, Am J Reprod Immunol Microbiol, 1987, 13(1):15-18.

Raghupathy R, Pregnancy: success and failure within the Th1/Th2/Th3 paradigm, Semin Immunol, 2001, 13 (4):219-227.

Raghupathy R, Th1-type immunity is incompatible with successful pregnancy, Immunol Today, 1997, 18(1)478-482.

Rayburn, Embryonic Medicine and Therapy, (Jauniaux, E., Barnea, E.R., Edwards, R.G., Eds.), The New England Journal of Medicine Book Review (May 13, 1999), 340(19):1519.

Raz I et al., Beta-cell function in new-onset type 1 diabetes and immunomodulation with heat-shock protein peptide (DialPrep277): a randomized, double-blind, phase II trial. Lancet, 2001, 358(9295):1749-1753.

Resnick IB et al., Nonmyeloablative stem cell transplantation and cell therapy for malignant and non-malignant diseases, Transpl Immunol, 2005, 14(3-4):207-219.

(56) References Cited

OTHER PUBLICATIONS

Rieger L et al., Th1- and Th2-like cytokine production by first trimester decidual large granular lymphocytes is influenced by HLA-G and HLA-E, Mol Hum Reprod, 2002, 8(3):255-261.
Ripka AS et al., Peptidomimetic design, Curr Opin Chem Biol, 1998, 2(4):441-452.
Rogers AM et al., Maternal-fetal tolerance is maintained despite transgene-driven trophoblast expression of MHC class I, and defects in Fas and its ligand, Eur J Immunol, 1998, 28(11):3479-3487.
Rolfe BE, Detection of fetal wastage, Fertil Steril, 1982, 37(5):655-660.
Zhang J et al., The N-CoR-HDAC3 nuclear receptor corepressor complex inhibits the JNK pathway through the integral subunit GPS2, Mol Cell, 2002, 9(3):611-623.
Zhou M et al., Expanded cohorts of maternal CD8+ T-cells specific for paternal MCH class I accumulate during pregnancy, J Reprod Immunol, 1998, 40(1):47-62.
Dermer (BiolTechnology, 1994, 12:320).
Dinh et al., The epidemiology of cancer in pregnancy, 2005, In Cancer and Pregnancy, Barnea et al. eds., Springer 1:1-6.
Diouf I et al., Monocyte activation and T cell inhibition in plasmodium falciparum-infected placenta, J Infect Dis, 2004, 189(12):2235-2242.
Dong VM et al., Transplantation tolerance: the concept and its applicability, Pediatr Transplant, 1999, 3(3):181-189.
Dressman HK et al., Gene expression profiles of multiple breast cancer phenotypes and response to neoadjuvant chemotherapy, Clin Cancer Res, 2006, 12(3 Pt 1):819-826.
Dyement DA et al., Genetics of multiple sclerosis, Lancet Neurol, 2004, 3(2):104-110.
Eisenbarth GS et al., Anti-thymocyte globulin and prednisone immunotherapy of recent onset type 1 diabetes mellitus, Diabetes Res, 1985, 2(6):271-276.
Elad S et al., Budesonide: a novel treatment for oral chronic graft versus host disease, Oral Surg Oral Med Oral Pathol Oral Radiol Endod, 2003, 95(3):308-311.
Elkin G et al., Prevention of diabetes in nonbese diabetic mice by nonmyeloablative allogenic bone marrow transplantation, Exp Hematol, 2004, 32(6):579-584.
Fernandez et al., Cancer and pregnancy:Clinical management and biological analyogy, 1994. In Barnea et al. (eds), Implantation and Early Pregnancy in Humans, pp. 355-377, Carnforth: Parthenon Publishing.
Ferrara JL et al., Acute graft versus host disease: pathophysiology, risk factors, and prevention strategies, Clin Adv Hematol Oncol, 2005, 3(5):415-419.
Fiocchi C, Intestinal inflammation: a complex interplay of immune and nonimmune cell interactions, Am J Physiol, 1997, 273(4 Pt 1):G769-G775.
Fischer DD et al., Isolation and characterization of a novel class II histone deacetylase, HDAC10, J Biol Chem, 2002, 277(8):6656-6666.
Fortin M et al., TGF-beta 2 and PGE2 in rabbit blastocoelic fluid can modulate GM-CSF production by human lymphocytes, Am J Reprod Immunol, 1997, 38(2):129-139.
Freshney (Culture of Animal Cells, A Manual of Basic Technique, Alan R. Liss, Inc., 1983, New York, p. 4).
Fresney et al, The Culture of Animal Cells, 1994, p. 5.
Fuzzi B et al., HLA-G expression in early embryos is a fundamental prerequisite for the obtainment of pregnancy, Eur J Immunol, 2002, 32(2):311-315.
Gardner DK et al., Culture of viable human blastocysts in defined sequential serum-free media, Hum Reprod, 1998, 13 (suppl 3):148-159.
Gardner et al., Complex physiologically based serum-free culture media increase mammalian embryo development, in in vitro fertilization and assisted reproduction, Proc 10.sup.th World Congress. 1997: 187, Gomel. V, Leung, PCK, eds, 187-191.
Gonzales et al., Preimplantation factor (PIF) could be a portion of CD2 or a homologue peptide, 2001, 57.sup.th Annual Meeting of the American Society for Reproductive Medicine, Orlando, FL (abstract).
Gonzales et al., Preimplantation factors (PIF) embryo-derived immunomodulatory peptides: possible implications for maternal recognition and allograft tolerance, 2002, 22.sup.nd Annual Meeting of the American Society for Reproductive Immunology,Chicago, IL (abstract).
Gonzales, R.R., Leavis, P.C., Ramos, M.P., Kolenko, V.M., Coulam, C.B., Barnea, E.R., 2001, Preimplantation factor (PIF) may modulate maternal cellular immunity (CD2), VII International Congress of Reproductive Immunology, Organized by ISIR, TheInternational Society for Immunology of Reproduction, Opatja, Croatia.
Gonzalez et al. Immunomodulatory features of preimplantation factors (PIF) from mouse embryos, 11th World Congress on Human Reproduction, Jun. 1-4, 2002, Montreal, Canada (abstract).
Gonzalez et al., Preimplantation Factor (PIF) may modulate maternal cellular immunity (CD2), SIEP, American Journal of Reproductive Immunology, 2001, 46(1):68-69.
Gonzalez et al., Preimplantation Factors (PIF) embryo-derived immunomodulatory peptides: possible implications for maternal recognition and allograft tolerance, American Journal of Reproductive Immunology, 2002, 47(6):347.
Gonzalez, et al., Preimplantation factor (PIF) could be a portion of CD2 or a homologue peptide, 57.sup.th Annual Meeting of the American Society for Reproductive Medicine, Orlando, FL (Oct. 20-25, 2001), (Abstract).
Gonzalez, et al., Preimplantation Factors (Pif) Embryo-Derived Immunomodulatory Peptides: Possible Implications for Maternal Recognition and Allograft Tolerance, 22.sup.nd Annual Meeting of the American Society for Reproductive Immunology, Chicago,IL (2002), (Abstract)—Also pub. at Am J Reprod Immunol. 47(6):347.
Goodman, et al., The Pharmacological Basis of Therapeutics, 6.sup.th Ed., MacMillan Publ. Co., New York (1980), (TOC).
Goodnow CC, Pathways for self-tolerance and the treatment of autoimmune diseases, Lancet, 2001, 357 (9274):2115-2121.
Guenther MG et al., A core SMRT corepressor complex containing HDAC3 and TBL1, a WD40-repeat protein linked to deafness, Genes Dev, 2000, 14(9):1048-1057.
Guller S et al., The role of placental Fas ligand in maintaining immune privilege at maternal-fetal interfaces, Semin Reprod Endocrinol, 1999, 17(1):39-44.
Gura T, Systems for identifying new drugs are often faulty, Science, 1997, 278(5340):1041-1042.
Hafler DA, Multiple Sclerosis, J Clin Invest, 2004, 113(6):788-794.
Hardy K et al., Growth factor expression and function in the human and mouse preimplantation embryo, J Endocrinol, 2002, 172(2):221-236.
Herold KC et al., Anti-CD3 monoclonal antibody in new-onset type 1 diabetes mellitus, N Engl J Med, 2002, 346 (22):1692-1698.
Heyner S, Growth factors in preimplantation development: role of insulin and insulin-like growth factors, Early Pregnancy, 1997, 3(3):153-163.
Ho HN et al., Distribution of Th1 and Th2 cell populations in human peripheral and decidual T cells from normal and anembryonic pregnancies, Fertil Steril, 2001, 76(4):797-803.
Hrbuy VJ et al., Synthesis of oligopeptide and peptidomimetic libraries, Curr Opin Chem Biol, 1997, 1(1):114-119.
Hruby VJ et al., Conformational and topographical considerations in designing agonist peptidomimetics from peptide leads, Curr Med Chem, 2000, 7(9): 945-970.
Huggett AC et al., Characterization of a hepatic prolifeation inhibitor (HPI): effect of HPI on the growth of normal liver cells—comparison with transforming growth factor beta, J Cell Biochem, 1987, 35(4):305-314.
Hughes RA, Systematic reviews of treatment for inflammatory demyelinating neuropathy, J Anat, 2002, 200 (4):331-339.
Jain RK, Barriers to drug delivery in solid tumors, Sci Am, 1994, 271(1):58-65.
Janeway, et al., Immunobiology, the Immune System in Health and Disease, Third Edition, Garland Publishing Inc. (Jan. 8, 1997), pp. 7:25 and 9:31.

(56) References Cited

OTHER PUBLICATIONS

Jauniaux et al., Embryonic Medicine and Therapy, 1997, Editorial Position, Oxford: Oxford University Press.
Jauniaux et al., Preface: Future Directions and Limitations, 1997. In Jauniaux et al. (eds), Embryonic Medicine and Therapy, pp. 7-8, Oxford: Oxford University Press.
Jiang SP et al., Multiple mechanisms of peripheral T cell tolerance to the fetal "allograft", J Immunol, 1998, 160 (7):3086-3090.
Johnson and Tracey, 'Peptide and Protein Drug Delivery', In: Encyclopedia of Controlled Drug Delivery, vol. 2, 1999, pp. 816-833.
Johnson KP et al., Copolymer 1 reduces relapse rate and improves disability in relapsing-remitting multiple sclerosis: results of phase III multicenter, double-blind placebo-controlled trial, Neurology, 1995, 45(7)1268-1276.
Kaaja RJ et al., Manifestations of chronic disease during pregnancy, JAMA, 2005, 294(21):2751-2757.
Karussis DM et al., Inhibition of acute, experimental autoimmune encephalomyelitis by the synthetic immunomodulator linomide, Ann Neurol, 1993, 34(5):654-660.
Barnea ER, Current progress in early pregnancy investigation and the steps ahead, Early Pregnancy, 2000, 4(1):1-4.
Barnea ER, Dual effects of embryo-derived factors on hCG secretion by placental explants, 1994. In Barnea et al. (eds), Implantation and Early Pregnancy in Humans, pp. 271-282, Carnforth: Parthenon Publishing.
Barnea ER, Embryo-Material dialogue: Linking pregnancy recognition and proliferation control, 4th World Conference on Early Pregnancy, under the auspices of the Hungarian Society of Obstetrics and Gynecology and SIEP, the Society or the Investigationof Early Pregnancy, Pecs, Hungary (Jun. 1-3, 2000), (Abstract).
Barnea ER, Embryo-Maternal dialogue: from pregnancy recognition to proliferation control, 14.sup.th Rochester Trophoblast Conference, by Trophoblast Conference and SIEP, Rochester, NY (Oct. 4-8, 2000), (Abstract).
Barnea ER, Embryo-Maternal dialogue: linking pregnancy recognition to proliferation control, Rochester Trophoblast Conference 2000, under the auspices of the Trophoblast Conference and SIEP, the Society for the Investigation of EarlyPregnancy, 2000, Rochester, NY.
Barnea ER, EnVision the field of early pregnancy investigation, Early Pregnancy, Biol & Med, 1995, 1:169-170.
Barnea ER, Epilogue: Cancer and Pregnancy—a reason for hope, 2001. In Cancer and Pregnancy, Barnea et al. (eds), pp. 296-298, Springer London.
Barnea ER, From PIF identification to clinical applications: Immunemodulatory Embryo-Derived Novel Peptide: True BioMarker Dx and Nontoxic Rx Application, Mining the Plasma Proteone Meeting, Success Stories Session, PepTalk Conf., CHI CambridgeHealthtech Institute, Coronado, San Diego CA (Jan. 7-9, 2008) (Abstract).
Barnea ER, Immune system and proliferation control evolution from embryo to adulthood: Roles of preimplantation factor (PIF)* and development proteins (DPs), Renaissance Congress of the 21st Century: The Mother and Child, before, during andafter pregnancy. 2001. A Global union of Scientific Congresses, under the high patronage of the President of the Italian Republic, 5th SIEP World Conference, 1st International Congress of the Mediterranean Society of Reproduction and Neonatology, 4th International Congress of the International Society for New Technology in Gynecology, Reproduction and Neonatology, (2001).
Barnea ER, Insight into early pregnancy events: the emerging role of the embryo, Am J Reprod Immunol, 2004, 51 (5)319-322.
Barnea ER, Maternal Immune Recognition of Pregnancy is Initiated by Novel Embryo-Derived Preimplantation Factor (PIF), Invited Speaker. Hippokration Congress on Reproductive Immunology (4.sup.th ESRADI C) European Society for Reproductive and-Developmental Immunology, Rhodes, Greece (2003), pp. 123-124 (Abstract 1.32)—Also pub. in J. Reprod. Immun. pp. 23-24.
Barnea ER, New frontiers in early pregnancy investigation, Early Pregnancy, 1995, 1(1):1-3.
Barnea ER, Novel Preimplantation Factors (PIF) and Developmental Peptides (DPs) are involved in safeguarding pregnancy, The Fetus as a Patient, 2002, Budapest, Hungary (abstract).
Barnea ER, Preimplantation Factor: A specific embryo viability factor, The First National Congress on Human Assisted Reproduction with International Participation under the patronage of the Romanian Academy, Timisoara, Romania (May 27-29, 1999),(Abstract).
Barnea ER, Safeguards established at conception influence peri and postnatal life: Roles of Preimplantation Factors (PIF) and Developmental Proteins (DPs), World Congress of Perinatal Medicine, Parallel Scientific SIEP Meeting, Barcelona, Spain (Sep. 23-27, 2001), (Abstract).
Barnea ER, Signaling Between Embryo and Mother in Early Pregnancy: Basis for Development of Tolerance, Recurrent Pregnancy Loss Causes, Controversies and Treatment. Series in Maternal-Fetal Medicine, Informa Healthcare, Taylor and Francis Group publ.(2007), 2:15-22.
Barnea ER, The embryo: a privileged entity in a privileged site: lessons learnt from embryonal development, Early Pregnancy, 1997, 3(2):77-80.
Barnea ER, The role of preimplantation factor (PIF) in the immune response of pregnancy, Second International Congress on Autoimmunity, Mar. 1999, Tel Aviv, Israel.
Barnea ER, Underlying mechanisms and treatment of early pregnancy failure, Ferti Magazine, 2001, Ferti.Net Worldwide Fertility Network.
Bates MD et al., Aberrant cytokine production by peripheral blood mononuclear cells in recurrent pregnancy loss?, Hum Reprod, 2002, 17(9):2439-2444.
Battye KM et al., Production of platelet-activating factor by the pre-implantation sheep embryo, J Reprod Fertil, 1991, 93(2):507-514.
Beausoleil SA et al., Large-scale characterization of HeLa cell nuclear phosphoproteins, Proc Natl Acad Sci USA, 2004, 101(33):12130-12135.
Bell JJ et al., In trans T cell tolerance diminishes autoantibody responses and exacerbates experimental allergic encephalomyelitis, J Immunol, 2008, 180(3):1508-1516.
Bodian DL et al., Crystal structure of the extracellular region of the human cell adhesion molecule CD2 at 2.5 a resolution, Structure, 1994, 2(8):755-766.
Boklage CE, Survival probability of human conceptions from fertilization to term, Int J Fertil, 1990, 35(2):75, 79-94.
Bose R et al., Purified human early pregnancy factor from preimplantation embryo possesses immunosuppresive properties, Am J Obstet Gynecol, 1989, 160(4):954-960.
Bose R, Properties of human pre- and post-implantation embryo-associated immunosuppressor factor(s), Immunol Lett, 1991, 30(3):325-332.
Bresson D et al., Mechanisms underlying type I diabetes, Drug Discovery Today: Disease Mechanisms, 2004, 1 (3):321-327.
Bringer, et al., PIF-1 Improves Graft vs. Host Disease (GVHD) while maintaining Graft vs. Leukemia (GVL) effect after bone marrow transplantation in mice, The 5.sup.th Annual Congress of the Federation of the Israel Societies for ExperimentalBiology, Eilat, Israel (Jan. 28-31, 2008), (Abstract).
Burgess WH et al., Possible dissociation of the heparin-binding and mitogenic activities of heparin-binding (acidic fibroblast) growth factor-1 from its receptor-binding activities by site-directed mutagenesis of a single lysine residue, J Cell Biol, 1990, 111(5 Pt 1):2129-2138.
Burt RK et al., Hematopoietic stem cell transplantation for progressive multiple sclerosis: failure of a total body irradiation-based conditioning regimen to prevent disease progression in patients with high disability scores, Blood, 2003, 102(7):2373-2378.
Campbell A.M., Monoclonal Antibody Technology, Elsevier Science Publishing Company Inc., 1984, pp. 1-32.
Cavanaugh AC et al., The purification of early-pregnancy factor to homogeneity from human platelets and identification as chaperonin 10, Eur J Biochem, 1994, 222(2):551-560.

(56) References Cited

OTHER PUBLICATIONS

Chakrabarti L et al., Sequence of simian immunodeficiency virus from macaque and its relationship to other human and simian retroviruses, Nature, 1987, 328(6130):543-547.
Chaouat G et al., Control of fetal survival in CBAxDBA/2 mice by lymphokine therapy, J Reprod Fertil, 1990, 89 (2):447-458.
Chaouat G et al., IL-10 prevents naturally occurring fetal loss in the CBAxDBA/2 mating combination and local defect in IL-10 production in this abortion-prone combination is corrected by in vivo injection of IFN-tau, J Immunol, 1995, 154 (9):4261-4268.
Chaouat G et al., TH1/TH2 paradigm in pregnancy: paradigm lost? Cytokines in pregnancy/early abortion re-examining the TH1 and TH2 paradigm, Int Arch Allergy Immunol, 2004, 134(2):93-119.
Chard T et al., Early pregnancy factor, Biol Res Pregnancy Perinatol, 1987, 8(2 2D Half):53-56.
Chen C et al., Monitoring embryos after in vitro fertilization using early pregnancy factor, Ann N Y Acad Sci, 1985, 442:420-428.
Chen JD et al., A transcriptional co-repressor that interacts with nuclear hormone receptors, Nature, 1995, 377 (6548):454-457.
Choudhury SR et al., Human reproductive failure I: immunological factors, Hum Reprod Update, 2001, 7(2):113-134.
Clarke FM et al., Identification of molecules involved in the 'early pregnancy factor' phenomenon, J Reprod Fertil, 1991, 93(2):525-539.
Clarke FM, Identification of molecules and mechanisms involved in the 'early pregnancy factor' system, Reprod Fertil Dev, 1992, 4(4):423-433.
Collier M et al., Biochemical and pharmacological characterization of human embryo-derived activating factor, Hum Reprod, 1988, 3(8):993-998.
Cooper DW et al., Failure to detect altered rosette inhibition titres in human pregnancy serum, J Reprod Fertil, 1981, 61(1):241-245.
Coulam CB et al., Preimplantation factor (PIF) predicts subsequent pregnancy loss, Am J Reprod Immunol, 1995, 34 (2):88-92.
Coulam, et al., Preimplantation Factors (PIF) Predicts Subsequence Pregnancy Loss, The American Fertility Society 50.sup.th Annual Meeting, San Antonio, TX (Nov. 5-10, 1994), (Abstract).
Critser, E.S. et al., The Role of Platelet-Activating Factor in Reproduction, Chapter 15 in Immunological Obstetrics, W.W. Norton, New York, 1992, pp. 202-215.
Curti BD, Physical barriers to drug delivery in tumors, Crit Rev Oncol Hematol, 1993, 14(1):29-39.
Database YbuOrit [Online], Nuclear receptor corepressor 2 (N-CoR2) (Silencing mediator of retinoic acid and thyroid hormone receptor) (SMRT) (SMRTe) (Thyroid-.sub.a retinoic-acid-receptor-associated corepressor) (T3 receptor-associating factor)(TRAC) (CTG repeat protein 26) (SMAP270), retrieved from Ebi accession No. UNIPROT:Q9Y618 Database accession No. Q9Y618 (Nov. 1, 1999).
Rolfe FG et al., Cyclosporin A and FK506 reduce interleukin-5 mRNA abundance by inhibiting gene transcription, Am J Respir Cell Mol Biol, 1997, 17(2):243-250.
Romagnani S, Lymphokine production by human T cells in disease states, Annu Rev Immunol, 1994, 12:227-257.
Rosario GX et al., Morphological events in the primate endometrium in the presence of a preimplantation embryo, detected by the serum preimplantation assay, Hum Reprod, 2005, 20(1):61-71.
Rose et al., Manual of Clinical Laboratory Immunology, 5th edition, 1997, ASM Press, pp. 20-29.
Roussev et al., A novel bioassay for detection of preimplantation factor (PIF), 1994, American Society of Reproductive Immunology, XVI Annual Meeting, June, Philadelphia, PA (abstract).
Roussev et al., Clinical validation of preimplantation factor (PIF) assay, 1994, Second World Conference on Preimplantation and Early Pregnancy in Humans, May, Atlantic City, NJ (abstract).
Roussev RG et al., A novel bioassay for detection of preimplantation factor (PIF), Am J Reprod Immunol, 1995, 33 (1):68-73.
Roussev RG et al., Development and validation of an assay for measuring preimplantation factor (PIF) of embryonal origin, Am J Reprod Immunol, 1996, 35(3):281-287.
Roussev RG et al., Embryonic origin of preimplantation factor (PIF): biological activity and partial characterization, Mol Hum Reprod, 1996, 2(11):883-887.
Roussev, et al., Embryonic Origin of Preimplantation Factor (PIF), Society for Gynecological Investigation 42.sup.nd Meeting, Chicago, IL (1995), (Abstract).
Roussev, R.G., Barnea, E.R., Thomason, E.J., Coulam, C.B., 1994, A novel bioassay for detection of preimplantation factor (PIF), American Society of Reproductive Immunology, XVI Annual Meeting, June, Philadelphia, PA.
Runmarker B et al., Pregnancy is associated with a lower risk of onset and better prognosis in multiple sclerosis, Brain, 1995, 188(Pt 1):253-261.
Salomon B et al., B7/CD28 costimulation is essential for the homeostasis of the CD4+CD25+ immunoregulatory T cells that control autoimmune diabetes, Immunity, 2000, 12(4):431-440.
Sande S et al., Identification of TRACs (T3 receptor-associating cofactors), a family of cofactors that associate with, and modulate the activity of, nuclear hormone receptors, Mol Endocrinol, 1996, 10(7):813-825.
Sanyal MK et al., Immunoregulatory activity in supernatants from cultures of normal human trophoblast cells of the first trimester, Am J Obstet Gynecol, 1989, 161(2):446-453.
Schroeder RA et al., Tolerance and the 'Holy Grail' of transplantation, J Surg Res, 2003, 111(1):109-119.
Schumacher et al., Primer on the Rheumatic Diseases, 10th edition, 1993, Arthritis Foundation, pp. 86-89 and 100-105.
Shainer et al., Immue regulation and oxidateive stress reduction by preimplantation factor following syngeneic or allogeneic bone marrow transplantation, Conference Papers in Medicine 2013 2013:1-8.
Sharma S et al., Genes regulating implantation and fetal development: a focus on mouse knockout models, Front Biosci, 2006, 11:2123-2137.
Shi Y et al., Sharp, an inducible cofactor that integrates nuclear receptor repression and activation, Genes Dev, 2001, 15(9):1140-1151.
Shurtz-Swirski R et al., Human embryo modulates placental function in the first trimester: effects of neural tissues upon chorionic gonadotropin and progesterone secretion, Placenta, 1991, 12(5):521-531.
Shurtz-Swirski R et al., In vitro effect of anticardiolipin autoantibodies upon total and pulsatile placental hCG secretion luring early pregnancy, Am J Reprod Immunol, 1993, 29(4):206-210.
Shurtz-Swirski R et al., Patterns of secretion of human chorionic gonadotropin by superfused placental explants and the embryo-placental relationship following maternal use of medications, Hum Reprod, 1992, 7(3)300-304.
Shurtz-Swirski, et al., Anti-Cardiolipin Antibodies Affect Total and Pulsatile Placental Hcg Secretion During Early Pregnancy, Israel Conference of Fertility, Tel Aviv, Israel (1993), (Abstract).
Sicotte NL et al., Onset of multiple sclerosis associated with anti-TNF therapy, Neurology, 2001, 57(10):1885-1888.
Sipka S et al., Glucocorticosteroid dependent decrease in the activity of calcineurin in the peripheral blood mononuclear cells of patients with systemic lupus erythematosus, Ann Rheum Dis, 2001, 60(4):380-384.
Skolnick J et al., From genes to protein structure and function: novel applications of computational approaches in the genomic era, Trends Biotechnol, 2000, 18(1):34-39.
Skyler JS et al., Use of inhaled insulin in a basal/bolus insulin regimen in type 1 diabetic subjects: a 6-month, randomized, comparative trial, Diabetes Care, 2005, 28(7):1630-1635.
Slavin S et al., Non-myeloablative stem cell transplantation for the treatment of cancer and life-threatening non-malignant disorders; past accomplishments and future goals, Transfus Apher Sci, 2002, 27(2):159-166.
Slavin S et al., The graft-versus-leukemia (GVL) phenomenon: is GVL separable from GVHD?, Bone Marrow Transplant, 1990, 6(3):155-161.
Smart YC et al., Early pregnancy factor: its role in mammalian reproduction—research review, Fertil Steril, 1981, 35 (4):397-402.

(56) References Cited

OTHER PUBLICATIONS

Smart YC et al., Validation of the rosette inhibition test for the detection of early pregnancy in women, Fertil Steril, 1982, 37(6):779-785.
Somerset DA et al., Normal human pregnancy is associated with an elevation in the immune suppressive CD25+ CD4+ regulatory T-cell subset, Immunology, 2004, 112(1)38-43.
Sospedra M et al., Immunology of multiple sclerosis, Annu Rev Immunol, 2005, 23:683-747.
Spika S et al., Glucocorticosteroid dependent decrease in the activity of calcineurin in the peripheral blood mononuclear cells of patients with systemic lupus erythematosus, Ann Rheum Dis, 2001, 60(4):380-384.
Stewart CL et al., Preimplantation development of mammalian embryo and its regulation by growth factors, Dev Genet, 1997, 21(1):91-101.
Sturzebecher S et al., Expression profiling identifies responder and non-responder phenotupes to interferon-beta in multiple sclerosis, Brain, 2003, 126(Pt 6):1419-1429.
Szekeres-Bartha J, Immunological relationship between the mother and the fetus, Int Rev Immunol, 2002, 21 (6):471-495.
Tangri S et al., Maternal anti-placental reactivity in natural, immunologically-mediated fetal resorptions, J Immunol, 1994, 152(10):4903-4911.
Taubes G, Vaccines. Malaria parasite outwits the immune system, Science, 2000, 290(5491):435.
Than, et al., Embryo-Placento-Maternal Interaction and Biomarkers: From Diagnosis to Therapy—A Workshop Report, Placenta (Jan. 26, 2007), 28(Suppl. A)(21):S107-S110.
TNF Neutralization in MS, Neurology, 1999, 53:457-465.
Truitt RL, The mortimer M. Bortin Lecture: To destroy by the reaction of immunity: the search for separation of graft-versus-leukemia and graft-versus-host, Biol Blood Marrow Transplant, 2004, 10(8):505-523.
Wegmann TG et al., Bidirectional cytokine interactions in the maternal-fetal relationship: is successful pregnancy a TH2 phenomenon?, Immunol Today, 1993, 14(7):353-356.
Weiss L et al., Induction of resistance to diabetes in non-obese diabetic mice by targeting CD44 with a specific monoclonal antibody, Proc Natl Acad Sci USA, 2000, 97(1):285-290.
Weiss L et al., Preimplantation factor (PIF) reverses neuroinflammation while promoting neural repair in EAE model, J Neurol Sci, 2012, 312(1-2):146-157.
Whyte A et al., Reproductive immunology. Early pregnancy factor, Nature, 1983, 304(5922):121-122.
Wickramasinghe SN et al., Blood and bone marrow changes in malaria, Baillieres Best Pract Res Clin Flaematol, 2000, 13(2):277-299.
Wu AJ et al., Tumor necrosis factor-alpha regulation of CD4+CD25+ T cell levels in NOD mice, Proc Natl Acad Sci USA, 2002, 99(19):12287-12292.
Wu MY et al., Increase in the production of interleukin-10 early after implantation is related to the success of pregnancy, Am J Reprod Immunol, 2001, 46(6):386-392.
Abbas AK et al., Functional diversity of helper T lymphocytes, 1996, Nature 383(6603):787-793.
Ancsin JB et al., A binding site for highly sulfated heparin sulphate is identified in the N terminus of the circumsporozoite protein: significance for malarial sporozoite attachment to hepatocytes, J Biol Chem, 2004, 279 (21):21824-21832.
Aplin JD et al., Trophoblast-uterine interaction at implantation, Reprod Biol Endocrinol, 2004, 2:48.
Asano M et al., Autoimmune disease as a consequence of developmental abnormality of a T cell subpopulation, J Exp Med, 1996, 184(2):387-396.
Atkinson MA et al., The NOD mouse model of type 1 diabetes: as good as it gets?, Nat Med, 1999, 5(6):601-604.
Bainbridge D et al., HLA-G remains a mystery, Trends Immunol, 2001, 22(10):548-552.
Banker et al., Modern Pharmaceutics, Marcel Dekker, Inc., 1979 (TOC).
Barnea ER et al., Cancer and Pregnancy, 2001, Editorial Position, Springer: London.
Barnea ER et al., Control of cell proliferation by embryonal-origin factors, Am J Reprod Immunol, 1996, 35(4):318-324.
Barnea ER et al., Embryo-derived Preimplantation Factor (PIF*): Methods to assess embryo viability towards successful pregnancy, Vth Indian Congress of Gynecologic Endoscopy and ART and SIEP, Khajuraho, India (Nov. 2004), (Abstract).
Barnea ER et al., Embryo-maternal signaling prior to implantation, in Obstetrics & Gynecology, Section 2 Human Reproduction—Anatomy, Physiology, Embryology, Munteanu Ed. (Romanian Academy of Science Publishers), pp. 112-117, 2001.
Barnea ER et al., Embryonic Signals, in Jauniaux, 1997, Jauniaux, E., Barnea, E.R., Edwards, R.G. (eds.) Embryonic Medicine and Therapy, pp. 63-75 (Oxford University Press).
Barnea ER et al., Endocrinology of the placental and embryo-placental interaction, 1992. In Barnea et al. (eds), The First Twelve Weeks of Gestation, pp. 128-153, Berlin: Springer-Verlag.
Barnea ER et al., Epilogue, 1992. In Barnea et al. (eds), The First Twelve Weeks of Gestation, pp. 542-548, Berlin: Springer-Verlag.
Barnea ER et al., Evolution of the feto-placental unit, in Obstetrics & Gynecology, 2001, Section 2 Human Reproduction—Anatomy, Physiology, Embryology, Munteanu Ed. (Romanian Academy of Science Publishers), pp. 170-175.
Barnea ER et al., Expression of Novel Immunomodulators (PIF*) and Proliferation Controllers (DPs) by the Embryo and by the Placenta, Invited Speaker at the 32.sup.nd Conference of the European Teratology Society, Thessaloniki, Greece, ReproductiveToxicology (2004), 18:707-756 (Abstract.
Barnea ER et al., Further validation of an assay for preimplantation factor (PIF), 1994, Second World Conference on Preimplantation and Early Pregnancy in Humans. May, Atlantic City, NJ (abstract).
Barnea ER et al., Human embryo regulates placental function in first trimester, 1988, International Congress of Endocrinology, Kyoto, Japan (Abstract).
Barnea ER et al., Human embryonal extracts modulate placental function in the first trimester: effects of visceral tissues upon chorionic gonadotropin and progesterone secretion, Placenta, 1989, 10(4):331-344.
Barnea ER et al., Identification and validation of an assay for preimplantation (PIF), 1994, Society for Gynecological Investigation 41.sup.st Meeting, April, Chicago, IL (abstract).
Barnea ER et al., Identification and Validation of an Assay for Preimplantation Factor (PIF), 1994, Second World Conference on Implantation and Early Pregnancy in Humans, May, Atlantic City, NJ (abstract).
Barnea ER et al., Immune Modulation, by Embryo-Specific Peptides, Allow for Embryo Tolerance whilst Preserving the Maternal Host's Ability to Fight Pathogens: Preimplantation Factor (PIF), First Brown-Linkoping meeting on Basic and Clinical Aspects ofReproductive Immunology, Providence, RI (Nov. 15, 2002), (Abstract).
Barnea ER et al., Immune System (IS) and Proliferation Control (PC) from Embryo to Adulthood: Roles of Preimplantation Factor (PIF) and of Developmental Proteins (DPs), 2001. In the Woman and Child Before, During and After Pregnancy, E.V. Cosmi Ed(Monduzzi Editore).
Barnea ER et al., Immune System (IS) and Proliferation Control (PC) from Embryo to Adulthood: Roles of Preimplantation Factor (PIF) and of Developmental Proteins (DPs), from Renaissance Congress of 21.sup.st Century: The Woman and Child Before, Duringand After Pregnancy, Cosmi ed., Monduzzi Editore, Rome, Italy (May 22-26, 2001), pp. 93-102.
Barnea ER et al., Implantation and Early Pregnancy in Humans, 1994, Editorial Position, Carnforth: Parthenon Publishing.
Barnea ER et al., Implantation in Obstetrics and Gynecology, 2001, Section 2 Human Reproduction-Anatomy, Physiology, Embryology, Munteanu Ed. (Romanian Academy of Science Publishers) pp. 117-123 (TOC only).

(56) References Cited

OTHER PUBLICATIONS

Barnea ER et al., Maternal Immune Response to Trophoblast, GTD and Cancer, In: Shoenfeld, Y. and Gerhwin, M.E. (eds) Cancer and Autoimmunity, 2000, pp. 343-350, Elsevier Science B.V. Publishers.
Barnea ER et al., Maternal Immune Response to Trophoblast, GTD, and Cancer, Elsevier Science B.V. Publishers (1999), pp. 309-316.
Barnea ER et al., New perspectives on prevention of environmentally-induced damage to the embryo, Reproduction Humaines et Hormones, 1996, 7:423-428.
Barnea ER et al., Novel Embryo-Derived Preimplantation Factor (PIF): An Immune-Modulatory Therapy Approach for Immune Disorders, 5.sup.th International Congress on Autoimmunity, Sorrento, Italy (2006).
Barnea ER et al., Partial characterization of embryo-derived preimplantation factor (PIF), Ninth World Congress on Human Reproduction, May 1996, Philadelphia, PA.
Barnea ER et al., Partial characterization of mammalian preimplantation factor (PIF) in culture and in vivo, 1998, Fourth International Meeting Mechanisms in Local Immunity: and join meeting Fourth Meeting of Alps Adria Society for Immunology of Reproduction. (AASIR), September, Opatija, Croatia (abstract).
Barnea ER et al., Prediction of Implantation in ART using Molecular Biology, Assisted Reproductive Technology (2004), pp. 183-194.
Barnea ER et al., Pregnancy derived compounds that control proliferation, 2001, In Cancer and Pregnancy, Bernea et al. eds., Springer 2:277-286.
Barnea ER et al., Pregnancy derived compounds that control proliferation, Cancer and Pregnancy, 2000, 22:275-284.
Barnea ER et al., Preimplantation Factor (PIF): Current Developments, 1996, Third World Conference on Early Pregnancy—An Interdisciplinary Approach, October, Atlantic City, NJ (abstract).
Barnea ER et al., Preimplantation Factor (PIF): Novel Immunemodulatory Peptide and Expression by Gestational Tissues, 12.sup.th International Federation of Placenta Association (IFPA), Kobe, Japan (Sep. 6-9, 2006), (Abstract).
Barnea ER et al., Preimplantation Factor (PIF): Relevance for Human Pregnancy, 24.sup.th Ann. Mtg. of the American Society for Reproductive Immunology, St. Louis, MO (2004), (Abstract).
Barnea ER et al., Preimplantation Factor: From Embryo Tolerance to Embryo Viability Detection and Treatment of Autoimmune Diseases, Eleventh International Symposium for Immunology of Reproduction. (ISIR) International House of Scientists, Vama,Bulgaria (2006).
Barnea ER et al., Preimplantation signalling by the embryo, 3rd World Conference on Early Pregnancy, Oct. 3-6, 1996 (abstract).
Barnea ER et al., Progress in characterization of pre-implantation factor (PIF) in embryo cultures and in vivo, Am J Reprod Immunol, 1999, 42(2):95-99.
Barnea ER et al., Reflections on early pregnancy: organizing chaos or organized chaos?, Early Pregnancy, 1996, 2 (2):77-79.
Barnea ER et al., The Embryo-Trophoblast Paradox, Embryonic Medicine and Therapy, Oxford University Press (1997), 15:256-279.
Barnea ER et al., The epidemiology of cancer in pregnancy, Cancer and Pregnancy, 2006, 1:1-6.
Barnea ER et al., The First Twelve Weeks of Gestation: A New Frontier in Investigation and Intervention, 1992, Editorial Position, Berlin: Springer-Verlag.
Barnea ER et al., Use of lymphocyte platelet binding assay for detecting a preimplantation factor: a quantitative assay, Am J Reprod Immunol, 1994, 32(3):133-138.
Barnea ER, (Editor-in-Chief), 1995, Early Pregnancy: Biology & Medicine cover page only.
Barnea ER, Apply Embryo Derived Tolerance for Managing Reproductive and Immune Disorders: Preimplantation Factor (PIF), 27.sup.th Annual Meeting of the American Society for Reproductive Immunology, Toronto, Canada (2007), (Abstract).
Barnea ER, Applying embryo-derived immune tolerance to the treatment of immune disorders, Ann N Y Acad Sci, 2007, 1110: 602-618.
Barnea ER, Critical Elements for Early Development and Beyond: Immune Tolerance (PIF) and Proliferation Control (DPs), Sixth World Conference of Early Pregnancy: Workshop on Embryology Early Pregnancy Investigation, Organized by SIEP, supported byRotunda the Center for Human Reproduction and Mangeshikar Center for Gynaelogical Endoscopic Surgery, Jodphur, India (2002), (Abstract).
Nakamura et al. "Delayed and acute effects of enterferon-γ on activity of an inwardly rectifying $K^+$ channel in cultured human proximal tubule cells," Am. J Physiol Renal Physiol,. Jan. 2009,298(1):F46-F52.
Valverde et al. "Potassium Channel-blockers as Therapeutic Agents to Interfere with Bone Resporption of Periodontal Disease," J. Dental Research, Jun. 2005, 84(6):488-499.
International Search Report dated Nov. 5, 2012 received in corresponding PCT/US2012/027480.
Hunter et al. "Selective Inhibitors of Kv11.1 Regulate IL-6 Expression by Macrophages in Response to TRL/IL-1R Ligands" 2010, The Scientific World Journal 10:1580-1596.
Ljungdahl et al. "Immune Cell Distribution in Gut-Associated Lymphoid Tissue and Synthesis of IL-6 in Experimental Porcine Peritonitis" 2000, European Surgical Research 32 :323-330.

\* cited by examiner

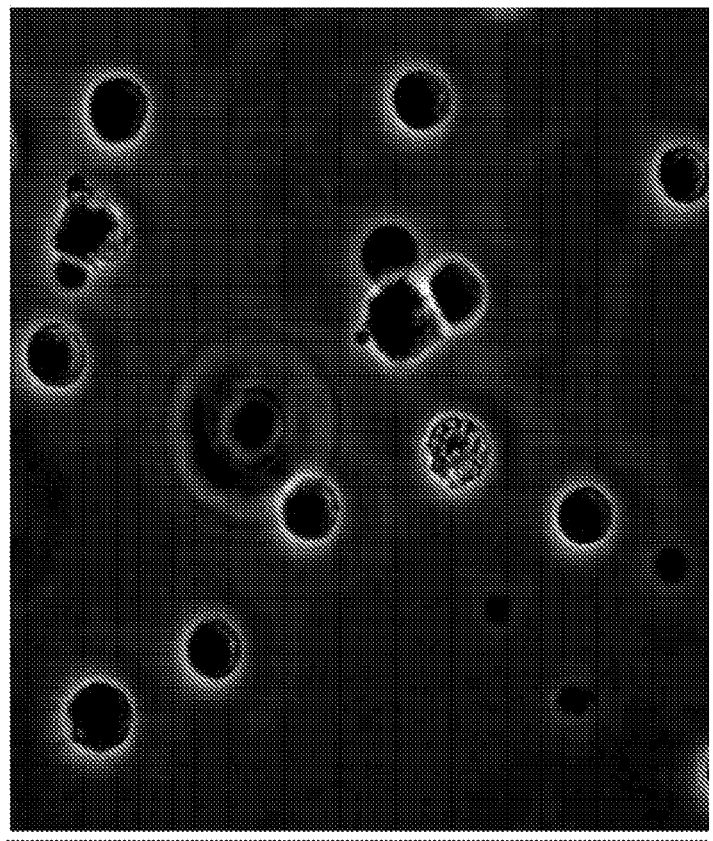
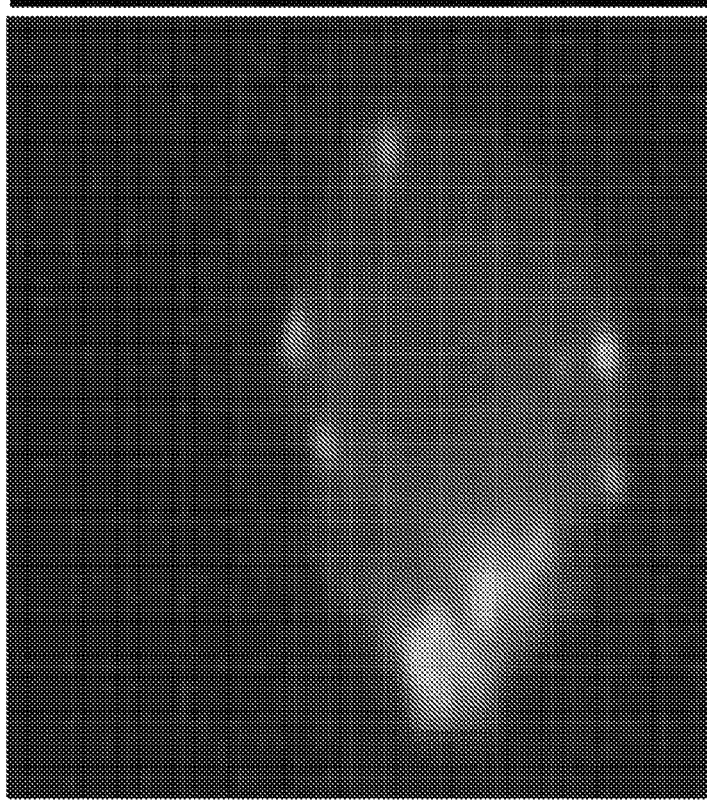
FIG. 1B
FIG. 1A

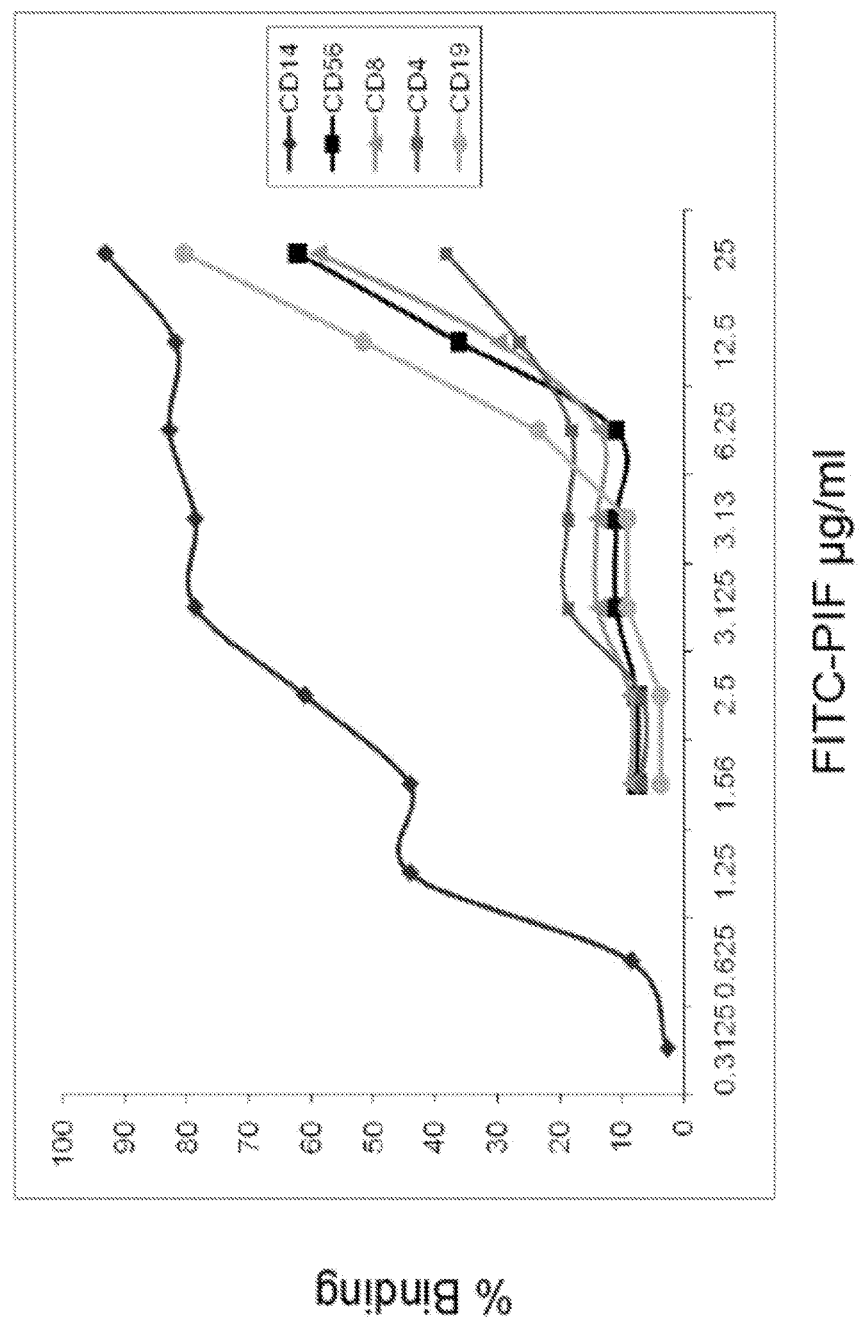

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: synthesized

<400> SEQUENCE: 1
```

```
Met Val Arg Ile Lys Pro Gly Ser Ala
1               5
```

<210> SEQ ID NO 2
<211> LENGTH: 13
<212> TYPE: PRT
<213> ORGANISM: Artificial Sequence
<220> FEATURE:
<223> OTHER INFORMATION: synthesized

<400> SEQUENCE: 2

```
Met Val Arg Ile Lys Pro Gly Ser Ala Asn Lys Pro Ser
1               5                   10
```

<210> SEQ ID NO 3
<211> LENGTH: 15
<212> TYPE: PRT
<213> ORGANISM: Artificial Sequence
<220> FEATURE:
<223> OTHER INFORMATION: synthesized

<400> SEQUENCE: 3

```
Met Val Arg Ile Lys Pro Gly Ser Ala Asn Lys Pro Ser Asp Asp
1               5                   10                  15
```

<210> SEQ ID NO 4
<211> LENGTH: 14
<212> TYPE: PRT
<213> ORGANISM: Artificial Sequence
<220> FEATURE:
<223> OTHER INFORMATION: synthesized

<400> SEQUENCE: 4

```
Met Val Arg Ile Lys Tyr Gly Ser Tyr Asn Lys Pro Ser Asp
1               5                   10
```

<210> SEQ ID NO 5
<211> LENGTH: 18
<212> TYPE: PRT
<213> ORGANISM: Artificial Sequence
<220> FEATURE:
<223> OTHER INFORMATION: synthesized

<400> SEQUENCE: 5

```
Ser Gly Ile Val Ile Tyr Gln Tyr Met Asp Asp Arg Tyr Val Gly Ser
1               5                   10                  15

Asp Leu
```

<210> SEQ ID NO 6
<211> LENGTH: 9
<212> TYPE: PRT
<213> ORGANISM: Artificial Sequence
<220> FEATURE:
<223> OTHER INFORMATION: synthesized

<400> SEQUENCE: 6

```
Val Ile Ile Ile Ala Gln Tyr Met Asp
1               5
```

<210> SEQ ID NO 7
<211> LENGTH: 10
<212> TYPE: PRT
<213> ORGANISM: Artificial Sequence
<220> FEATURE:
<223> OTHER INFORMATION: synthesized

```
<400> SEQUENCE: 7

Ser Gln Ala Val Gln Glu His Ala Ser Thr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (12)..(12)
<223> OTHER INFORMATION: Xaa can be any naturally occurring amino acid

<400> SEQUENCE: 8

Ser Gln Ala Val Gln Glu His Ala Ser Thr Asn Xaa Gly
1               5                   10
```

COMPOSITIONS AND METHODS FOR TREATMENT OF INTRACELLULAR DAMAGE AND BACTERIAL INFECTION

CLAIM OF PRIORITY

This application is a U.S. national stage filing under 35 U.S.C. §371 of International Application No. PCT/US2012/027480, filed Mar. 2, 2012, which claims priority to U.S. Provisional Application No. 61/448,446, filed Mar. 2, 2011, the disclosures of which are incorporated by reference in their entirety.

SUMMARY

Embodiments herein are directed to pre-implantation factor (PIF) for use in the treatment of intracellular damage. Embodiments are directed to a method of treating intracellular damage comprising administering a PIF peptide to a subject in need thereof. In some embodiments, the PIF peptide administered is in a therapeutically effective amount. In some embodiments, the intracellular damage may be the result of a disease. In some embodiments, the disease is caused by an intracellular bacterium. In some embodiments, the intracellular bacterium may be selected from *Listeria monocytogenes, Mycobacterium tuberculosis, Heliobacter pylori, Borrelia burgdorferi sensu stricto, Borelia afzelii*, and *Borrelia garinii*. In further embodiments, the disease may be selected from *Listeria*, malaria, Lyme disease, cardiovascular disease, duodenal peptic ulcer, atherosclerosis, peritonitis and tuberculosis. In some embodiments, the method of treating intracellular damage further comprises administering a potassium channel inhibitor. In some embodiments, the potassium channel inhibitor may be a Kv1.3 inhibitor. In some embodiments, the potassium channel inhibitor may be IFNγ.

Embodiments are directed to a method of treating tuberculosis comprising administering a PIF peptide. In some embodiments, PIF may neutralize local immune suppression induced by *Mycobacterium tuberculosis* (Mtb)-infected macrophages and/or increase host's immune response against Mtb infection. In further embodiments, PIF may prevent intracellular damage caused by tuberculosis. In some embodiments, a subject is diagnosed with tuberculosis. In some embodiments, a subject is at risk for tuberculosis. In some embodiments, the method may further comprise administering PIF in combination with other anti-tuberculosis agents.

Embodiments are directed to a method of decreasing dissemination of tuberculosis bacteria comprises administering PIF to a subject in need thereof. In some embodiments, the PIF peptide administered is in a therapeutically effective amount. In some embodiments, the method may further comprise administering PIF in combination with other anti-tuberculosis agents.

Embodiments are directed to a method of protecting against inflammation in intracellular damage comprising administering a PIF peptide to a subject in need thereof. Some embodiments describe a method of increasing cytokine secretion in response to intracellular damage comprising administering a PIF peptide to a subject in need thereof. In some embodiments, the PIF administered is in a therapeutically effective amount. In some embodiments, the intracellular damage may be the result of a disease. In some embodiments, the disease is caused by an intracellular bacterium. In further embodiments, the disease may be selected from a *Listeria monocytogenes* infection, malaria, Lyme disease, cardiovascular disease, diabetes, duodenal peptic ulcer, atherosclerosis and tuberculosis. In some embodiments, the method of protecting against inflammation in intracellular damage further comprises administering a potassium channel inhibitor. In some embodiments, the potassium channel inhibitor may be a Kv1.3 inhibitor. In some embodiments, the potassium channel inhibitor may be IFNγ.

Embodiments are directed to a method of modulating a potassium channel comprising administering a PIF peptide. In some embodiments, the potassium channel is Kv1.3. In some embodiments, modulating comprises blocking the activity of the potassium channel. In some embodiments, the PIF peptide modulates the potassium channel by binding to the channel. In some embodiments, the PIF administered is in a therapeutically effective amount.

Embodiments are directed to a method of treating atherosclerosis in a subject comprising administering a PIF peptide. In some embodiments, a therapeutically effective amount of PIF is administered. In some embodiments, a subject is diagnosed with atherosclerosis. In some embodiments, the subject is at risk for atherosclerosis. In some embodiments, the method may further comprise administering PIF in combination with other anti-atherosclerotic agents.

In some embodiments, PIF may treat atherosclerosis by reducing plaque in the aortic root. In some embodiments, PIF may treat atherosclerosis by reducing plaque in the aortic arch. In some embodiments, PIF may treat atherosclerosis by reducing a monocyte protein in the aortic arch. In further embodiments, the monocyte protein may be selected from vascular cell adhesion molecules (VCAM-1), monocyte chemotactic proteins (MCP-1) and clusters of differentiation (CD68). In some embodiments, PIF may treat atherosclerosis by reducing a monocyte protein in the aortic root. In further embodiments, the monocyte protein may be selected from vascular cell adhesion molecules (VCAM-1), monocyte chemotactic proteins (MCP-1) and clusters of differentiation (CD68). In some embodiments, PIF may treat atherosclerosis by reducing lipids in the aortic root. In some embodiments, PIF may treat atherosclerosis by reducing a cytokine in THP-1 cells. In further embodiments, the cytokine may be selected from interleukein 12, subunit beta (IL-12b) and interferon gamma (IFN-γ). The effect on plaque reduction on the aorta is direct without affecting circulating lipids.

Embodiments are directed to a method of treating peritonitis in a subject comprising administering a PIF peptide. In some embodiments, a therapeutically effective amount of PIF is administered. In some embodiments, a subject is diagnosed with peritonitis. In some embodiments, the subject is at risk for peritonitis. In some embodiments, the method may further comprise administering PIF in combination with other anti-peritonitis agents.

In embodiments, the PIF peptide may be selected from SEQ ID NO: 1; SEQ ID NO: 2; SEQ ID NO: 3; SEQ ID NO: 4; SEQ ID NO: 5; SEQ ID NO: 6; SEQ ID NO: 7; or SEQ ID NO: 8. In embodiments, the PIF peptide may be selected from SEQ ID NO: 1; SEQ ID NO: 2; SEQ ID NO: 3 and SEQ ID NO: 4. In embodiments, the PIF peptide may be selected from SEQ ID NO: 1; SEQ ID NO: 2; and SEQ ID NO: 3.

BRIEF DESCRIPTION OF THE FIGURES

For a fuller understanding of the nature and advantages of the present invention, reference should be had to the following detailed description taken in connection with the accompanying drawings, in which:

FIG. 1A illustrates a magnified immune cell showing FITC-PIF binding (fluorescent microscopy) at ×2000 magnification; the uptake appears to be intracellular. FIG. 1B illustrates minimal FITC-PIF binding to naïve PBMCs (phase-contrast microscopy) ×40 magnification. FIG. 1J illustrates dose-dependent binding of FITC-PIF to CD14+ cells, coupled with incomplete saturation of CD8+, CD4+, CD56+ (NK cells) and CD19+ cells even at 10-fold higher concentrations of FITC-PIF. Results are mean values of 4-10 samples per cell lineage.

FIG. 3B illustrates sPIF (50 nM); FIG. 3C illustrates PIFscr (50 nM); FIG. 3D illustrates sPIF (50 nM)+anti-CD3 mAb; FIG. 3E illustrates PIFscr+anti-CD3 mAb. sPIF affected variably stimulated PBMCs individual cytokines secretion. In contrast, some cytokine secretion in naïve PBMCs decreased (not shown). PIFscr affected only TNFα secretion (N=5). Cytokine secretion determined by Luminex 10-plex. FIG. 3F illustrates PIF promotes anti-CD3/CD28 induced TH2 and TH1 cytokines secretion. PBMCs were cultured in the presence of anti-CD3/anti-CD28-Mab for 24-48 hours. PIF increased both types of cytokines following TCR stimulation. PIF alone had no significant promoting effect on cytokine secretion, representative of three different experiments. The effect on PBMCs at 48 hours was less pronounced (data not shown). At the end of experiment mRNA was extracted and global gene expression was analyzed by using an Affymetrix chip.

FIG. 9A signifies PIF 1 mg/kg/day treatment causes a significant reduction in lipids compared to ScPIF 1 mg/kg/day in the aortic root ((n=8, p<0.01, **p=<0.0001). To confirm the reduction in lipids and foam cells were due to PIF's actions on the atherosclerotic lesion and not fat levels as a whole, Cobas was used to determine the cholesterol levels using mouse plasma from different treatment groups. All animals still had very high cholesterol levels and to obtain a reading, the plasma was diluted to 1:10. After analysis, no statistical difference was seen between any group using one way ANOVA paired with Tukey's Multiple Comparison Test.

DETAILED DESCRIPTION

Figure 1C:
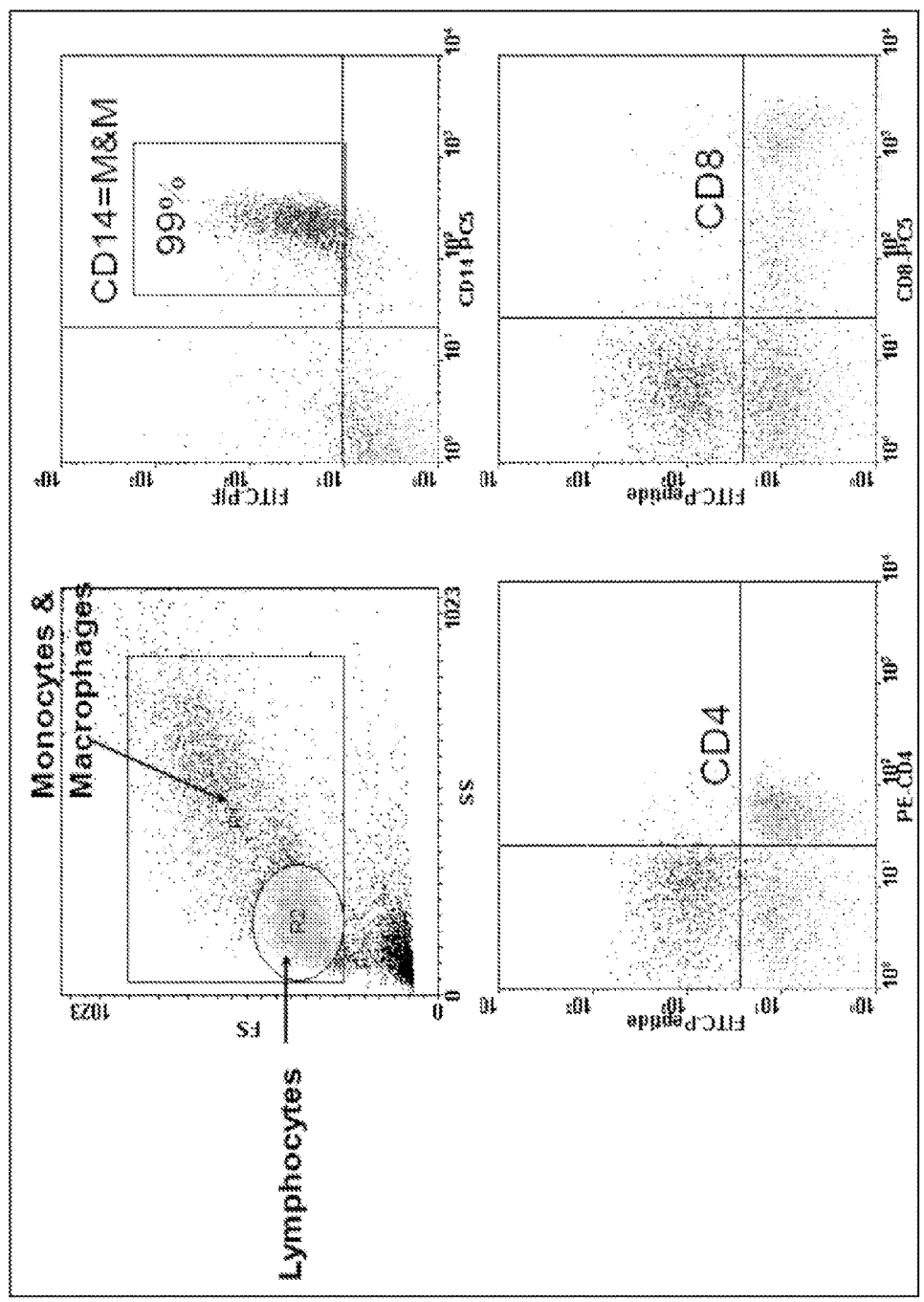
FIG. 1C illustrates FITC-PIF binds all unstimulated CD14+ cells (upper right panel); minimal binding to unstimulated CD4+ and CD8+ cells (lower left and right panels).
Figure 1D:
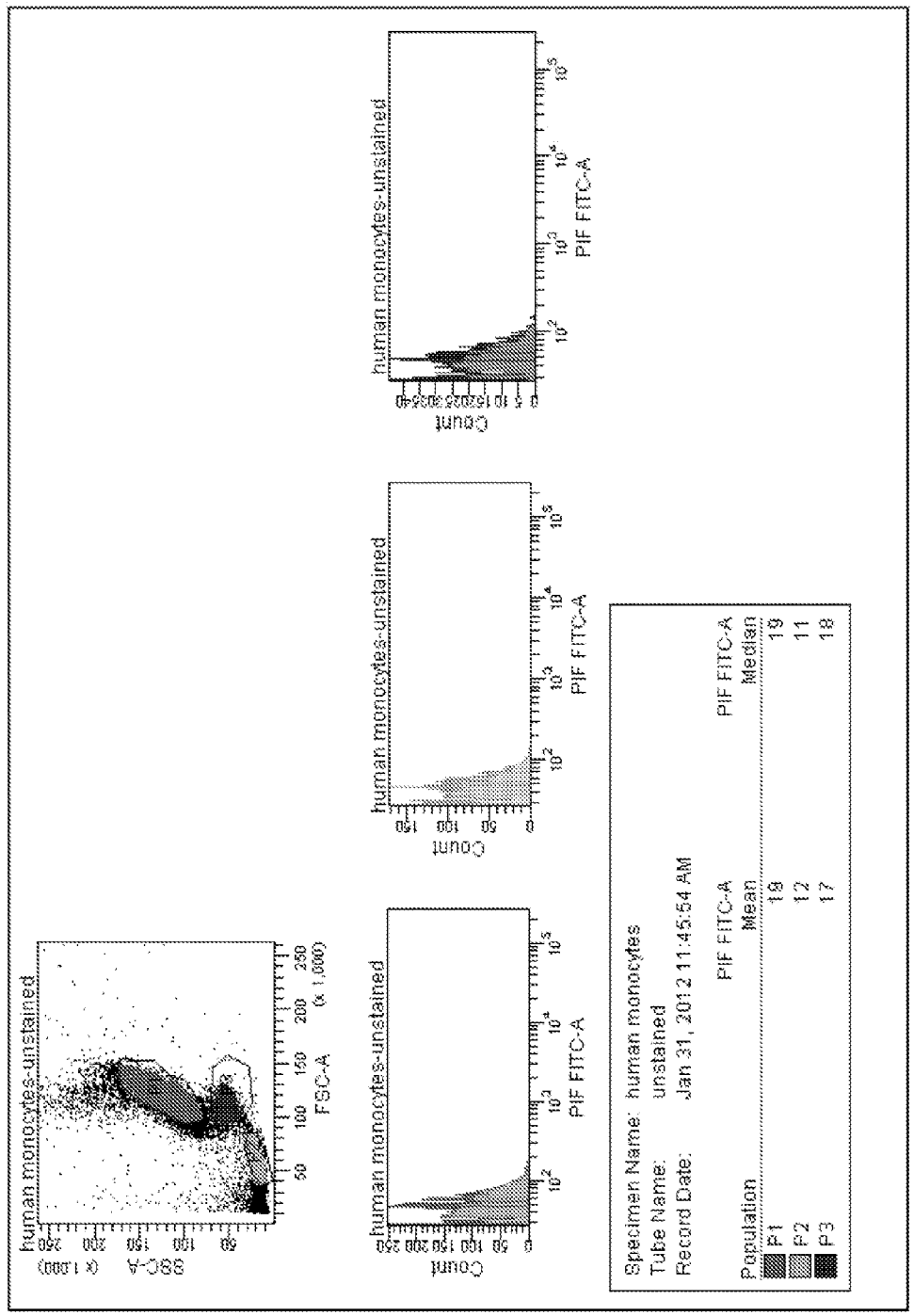
FIG. 1D illustrates unstained negative control and FIG. 1E illustrates test human blood underwent RBC lysis procedure and was incubated with PIF-FITC (1 uM) or PBS for 15 mins. The results indicated the PIF-FITC binds mainly to granulocyte population based on FSC/SSC.
Figure 1E:
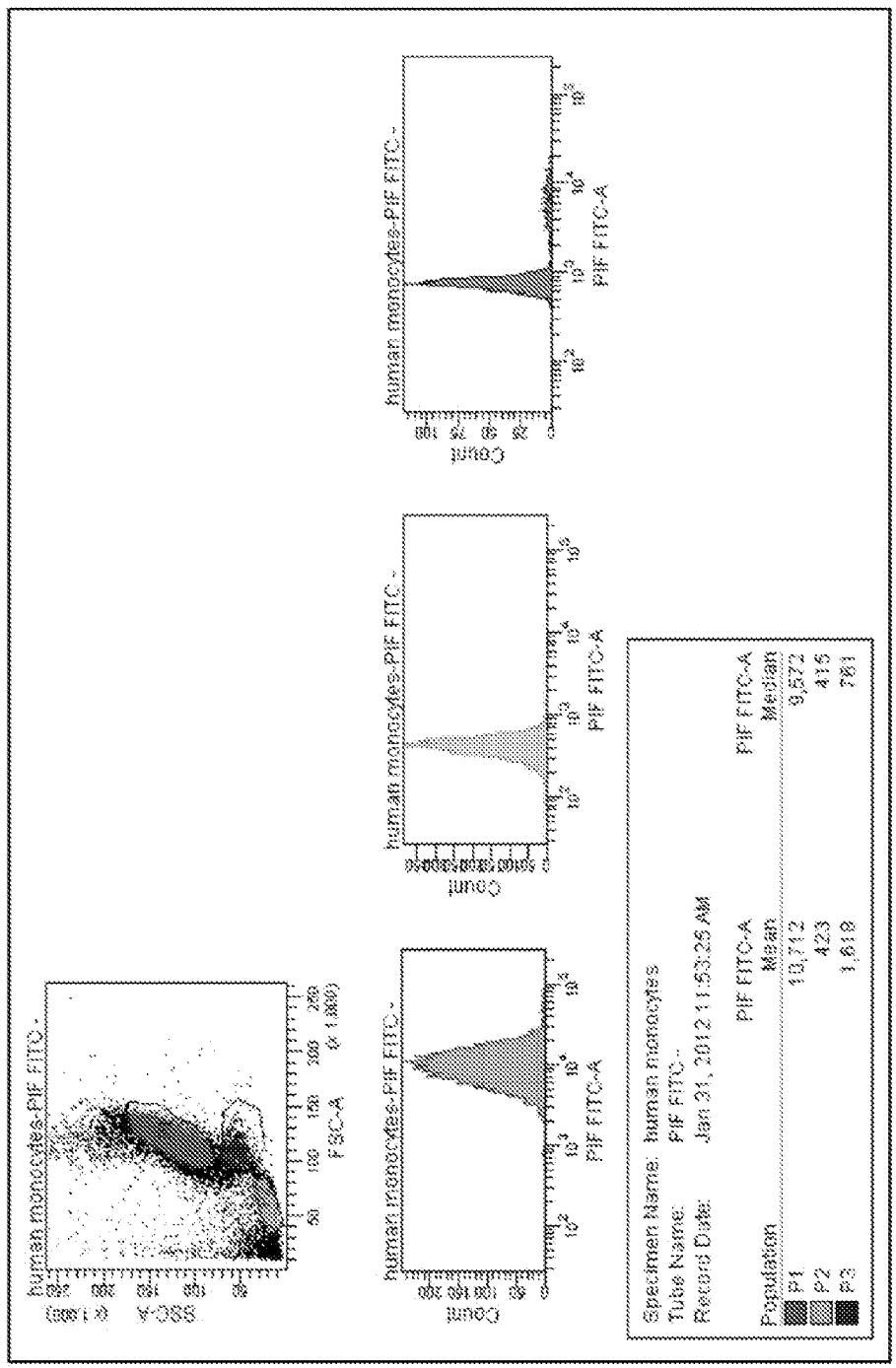
Figure 1F:
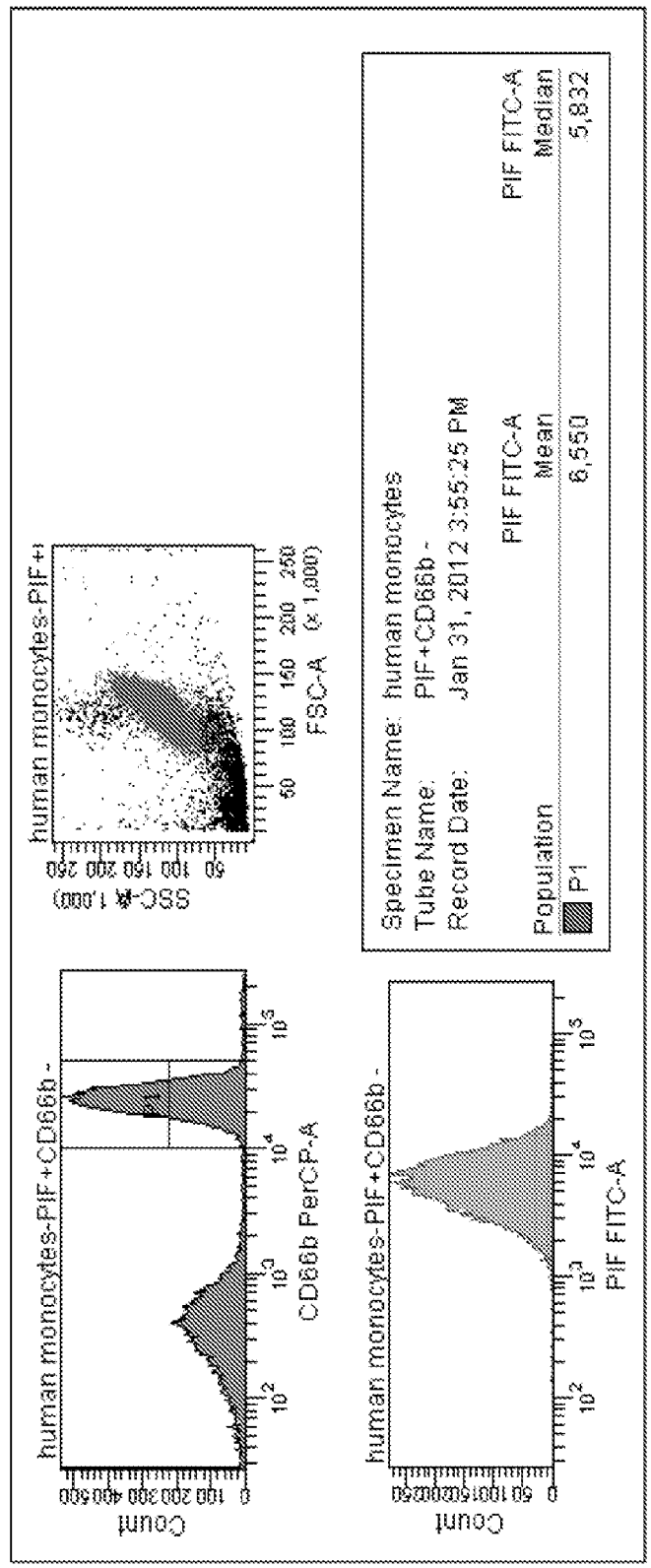
FIG. 1F illustrates human whole blood was incubated with PIF-FITC+CD66b (top graphs) or CD14 (bottom graphs). Results indicated the PIF-FITC binds strongly to CD66b positive granulocytes follow by CD14 positive monocytes.
Figure 1G:
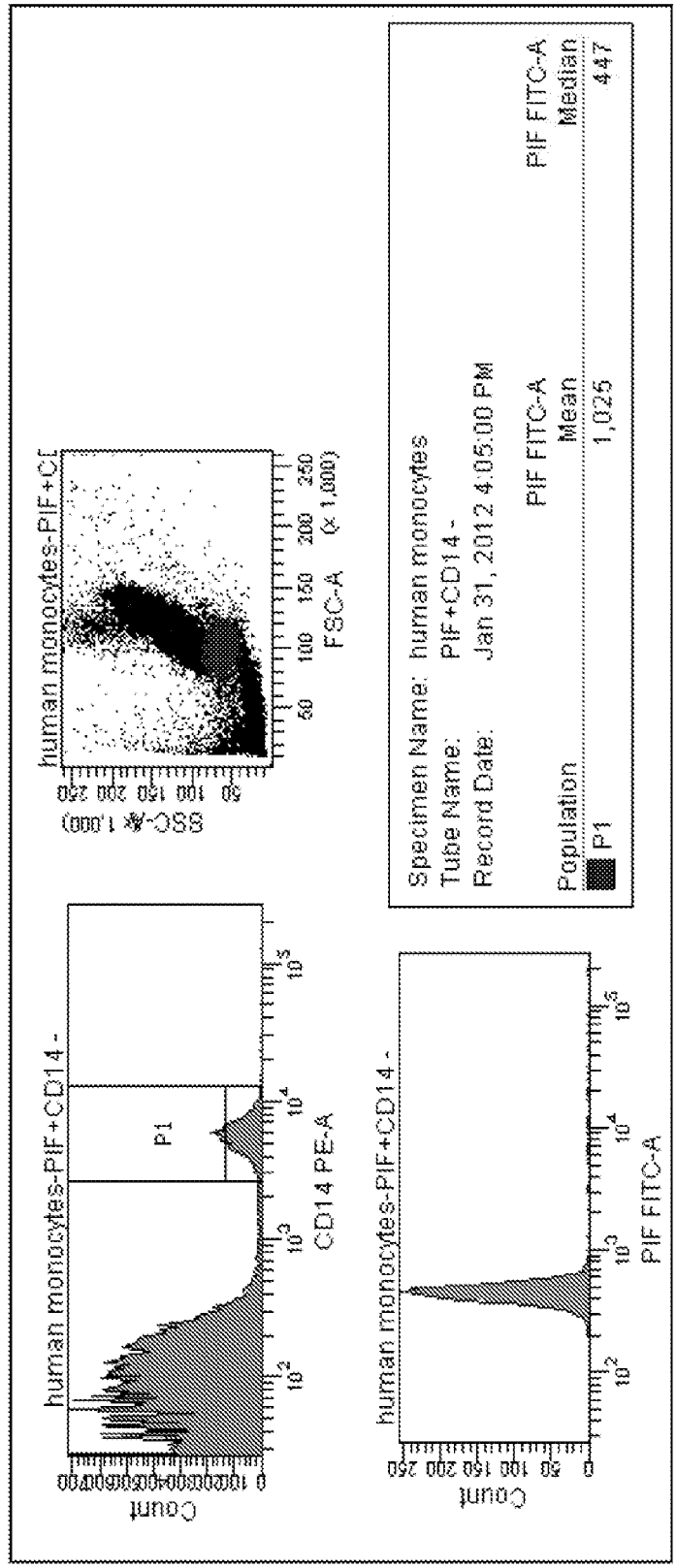
FIG. 1G illustrates 100 uM PIF-FITC (50 ul) (top row) was injected to 25 g C57/BL6 mice through the jugular vein. The mice were culled 5 minutes after injection. Blood was collected through the inferior vena cava in a heparin tube. Red blood cells were lysed by a lysis buffer. Cell was resuspended in FACS buffer and stained for CD14-PE (middle row) and CD45-APC (bottom row). The results indicated the binding of PIF-FITC to granulocytes (P3); these granulocyte may have CD14 and CD45 markers.
Figure 1H:
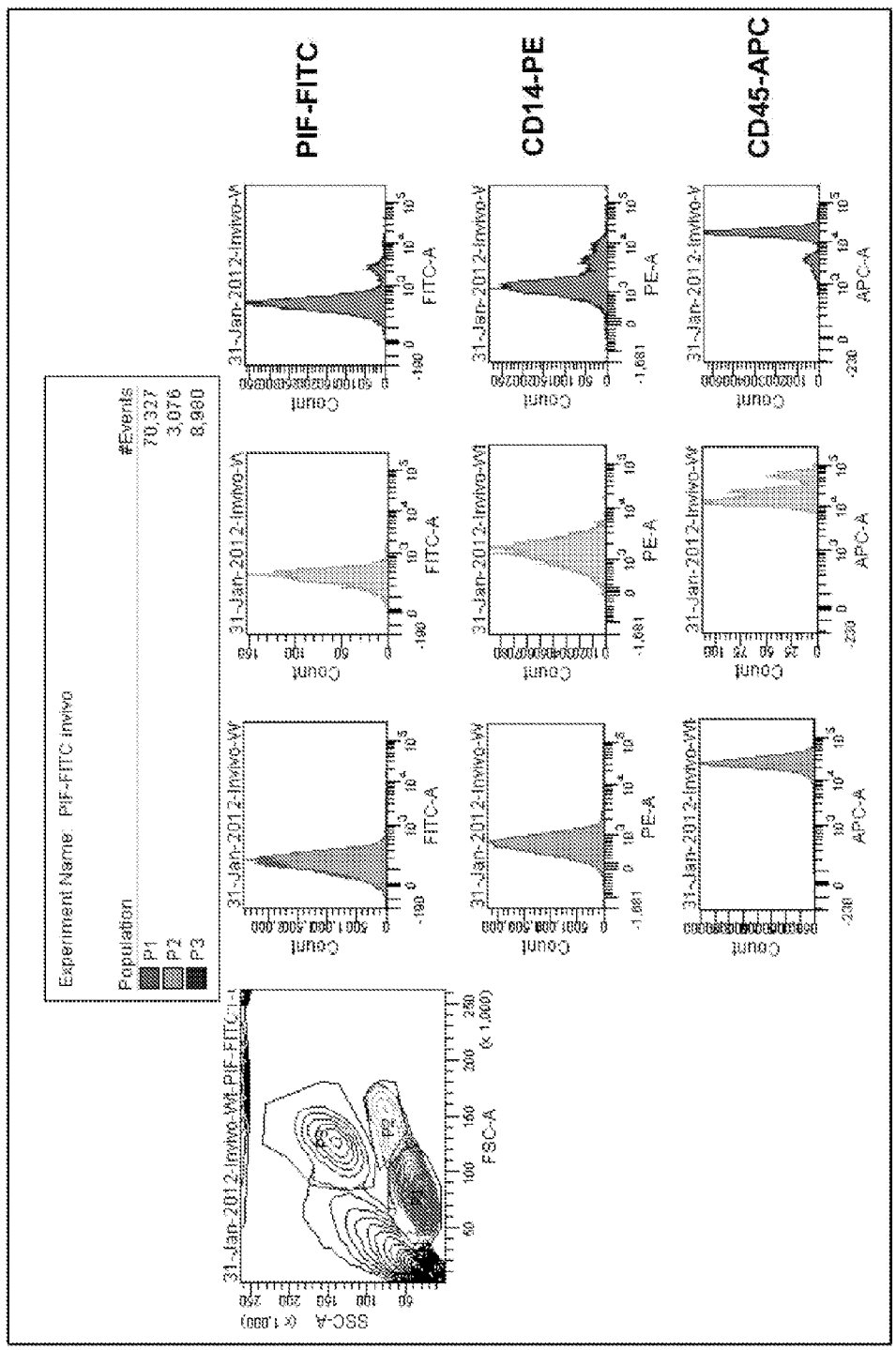
FIG. 1H and FIG. 1I illustrate cell types that interact with PIF. Mouse blood and bone marrow cells were stained for one hour with PIF-FITC conjugate and markers for immune cell sub-populations. FACS analysis revealed that PIF preferably interacts with CD11b+ Monocytes.
Figure 1I:
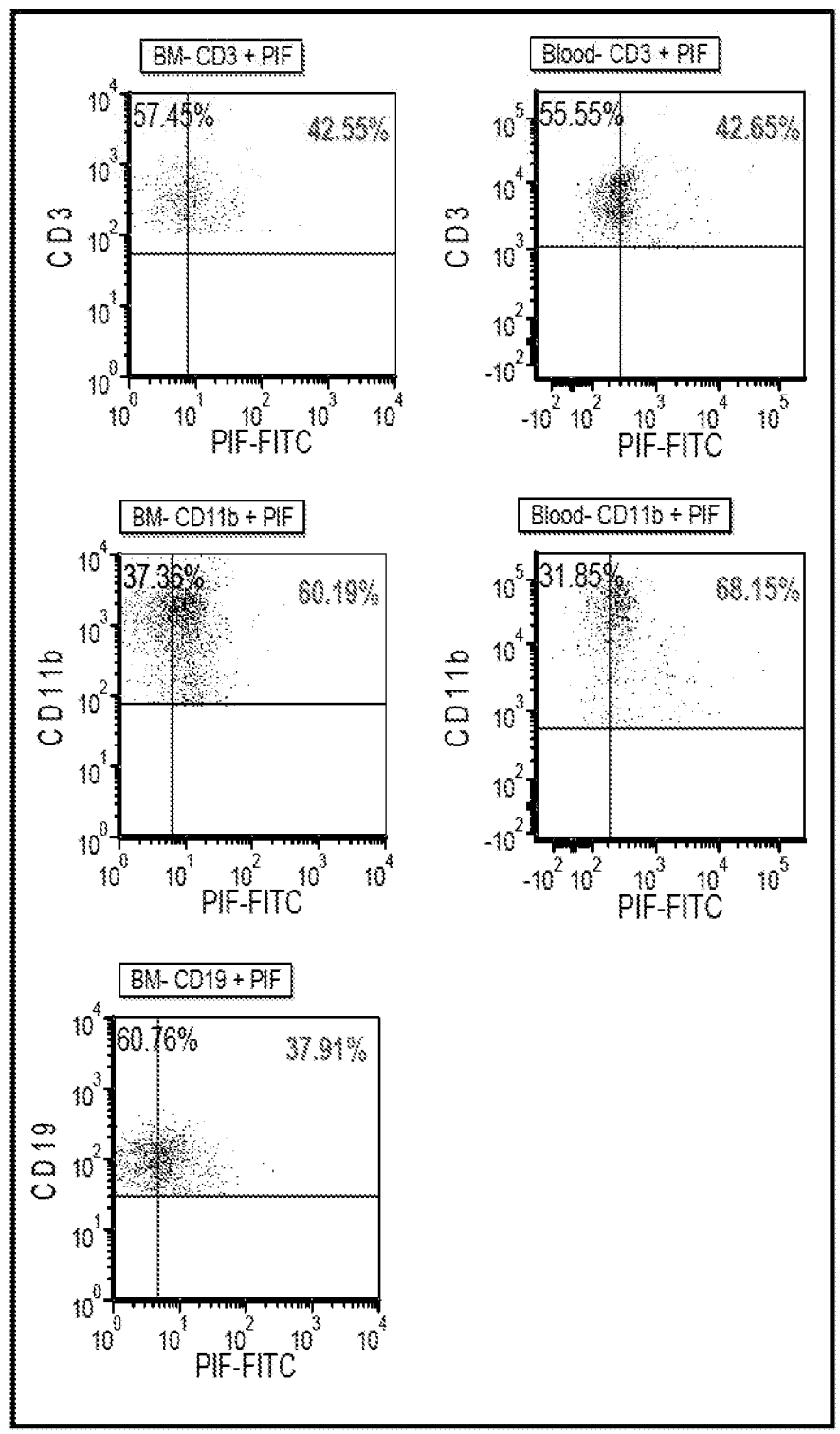
Figure 2A:
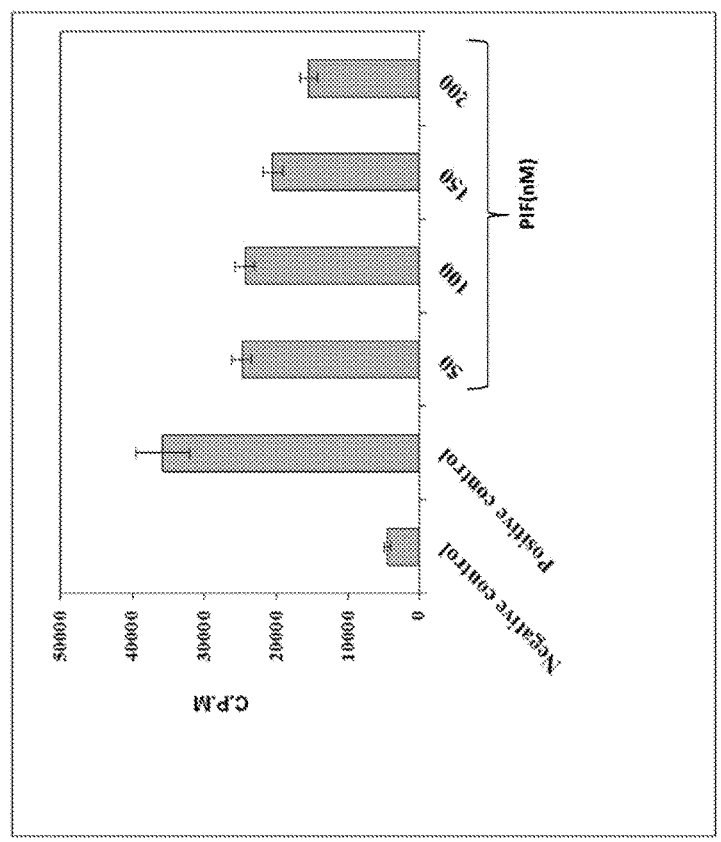
FIG. 2A illustrates that PIF reduces allogenic lymphocyte proliferation in a dose dependent manner in MLR analysis. Mouse splenocytes were used for mixed Lymphocytes Reaction (MLR). Balb/c cells were cultured in the presence of irradiated C57/B1 cells for 4 days. Different concentrations of PIF were added to the culture media. Cell proliferation was tested by H3 Tymidine uptake assay. PIF was found to reduce cells proliferation in a dose dependent manner. The differences between the positive control (Pos.), 150 nM and 200 nM PIF are significant (Mann-Whitney: P≤0.03). One representative experiment is shown out of four performed.
Figure 2C:
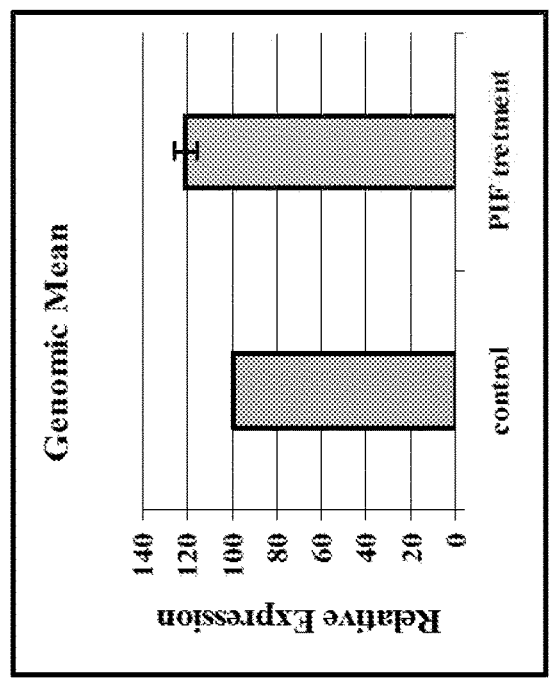
FIG. 2C illustrates PIF up-regulates B7-H1 regulatory protein in CD11b+ cells. Bone marrow derived Monocytes were grown in culture for 10 days in the presence or absence of 200 nM PIF. At day 7, 100 ng/ml IFN γ was added. After 10 days cells were analyzed by FACS analysis using anti-B7-H1 antibodies.
Figure 2B:
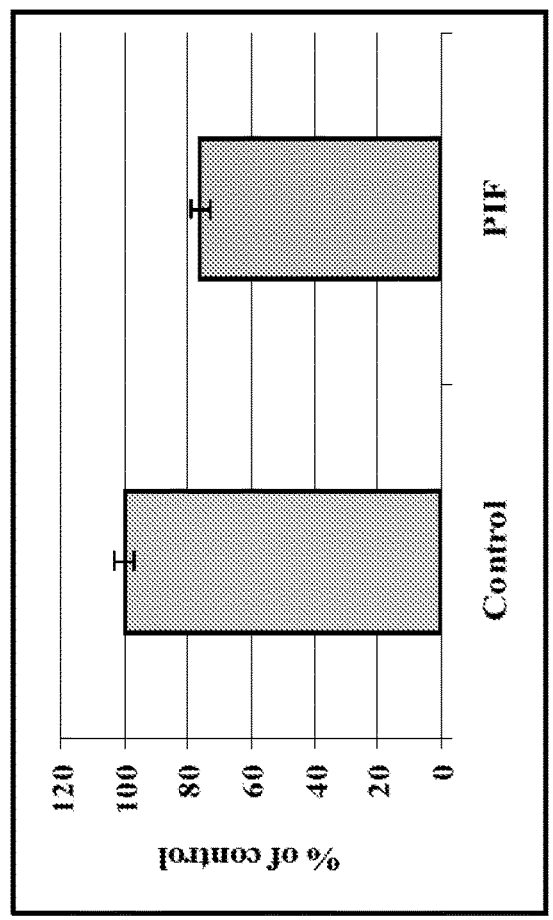
FIG. 2B illustrates PIF-treated CD11b+ cells were found to inhibit T cell proliferation. Bone marrow derived Monocytes were grown in culture for 10 days in the presence of 200 nM PIF and then co-cultured with T cells for 4 days. Anti-CD3 antibodies were added to the medium for T cell activation. Cell proliferation was tested by H3 Thymidine uptake. PIF-treated monocytes reduced proliferation but did not block it, which is likely because PIF's effect is modulatory and not inhibitory.
Figure 2D:
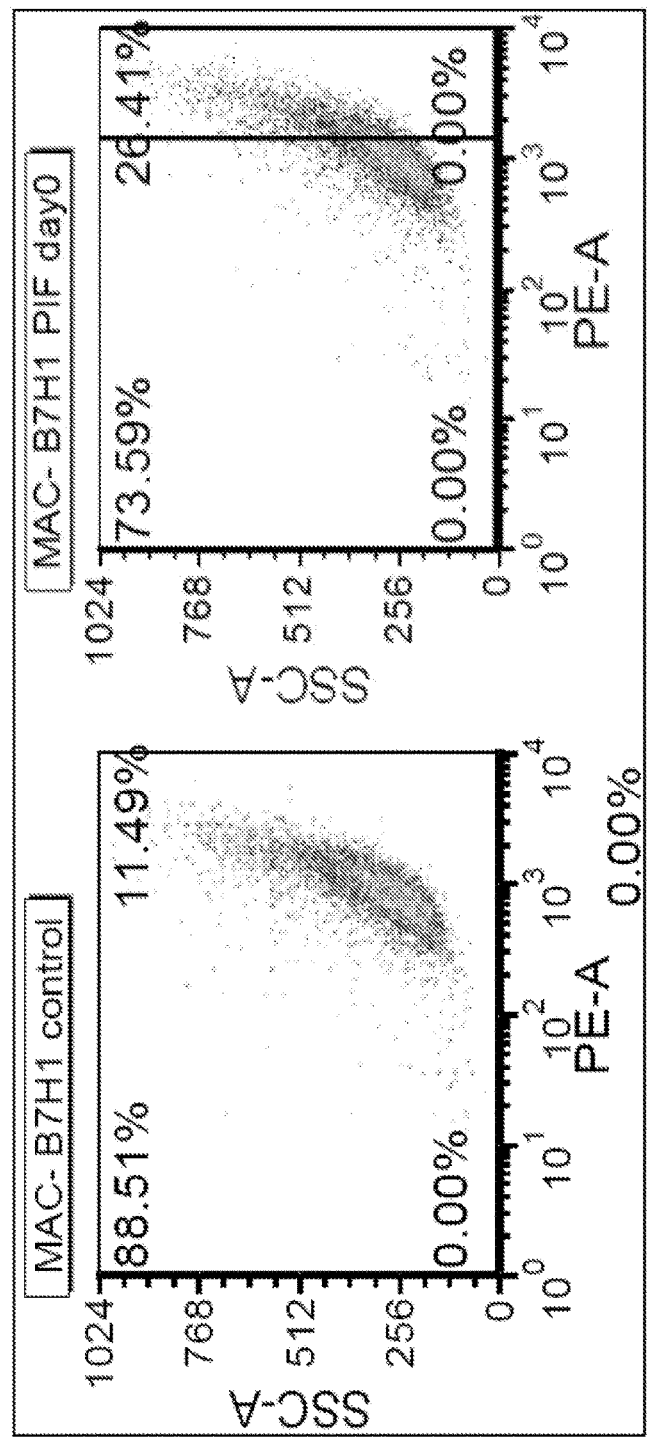
FIG. 2D illustrates murine macrophages were cultured with GM-CSF for 10 days. IFN-γ was added to the culture at day 7 for cell activation. When sPIF added to the culture at day 0 or 7, B7-H1 expression was significantly increased. This is relevant since B7-H1 is one of the newly defined inhibitory B7 family molecules. It is known that IFN gamma potently stimulates B7-H1 expression on APC.
Figure 2E:
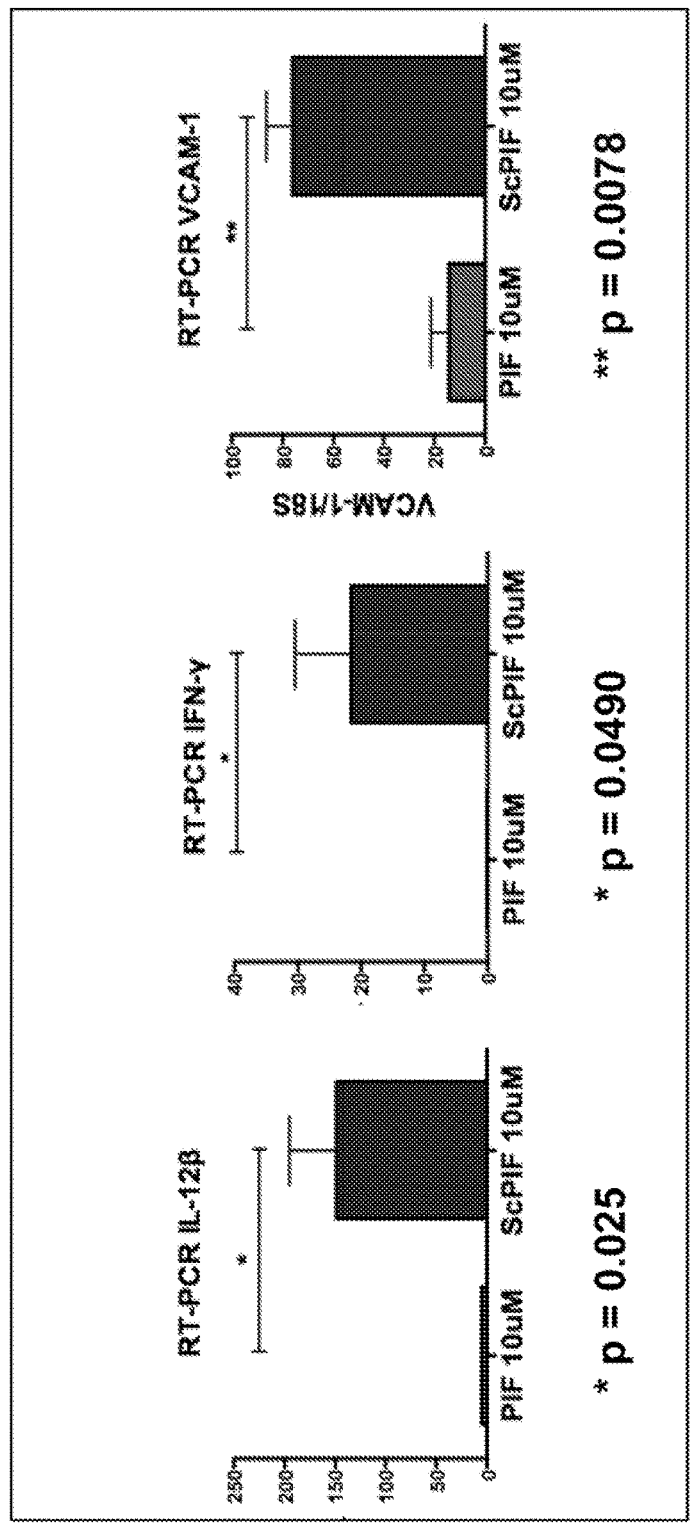
FIG. 2E illustrates PIF reduced VCAM-1, IL-12b and IFNg in THP-1 cells. THP-1 cells were incubated for 48 hours, then were stimulated with 10 ug/TGF-b and collected at 0, 1, 8, 12 and 24 hour time points. This showed gene regulation changes at certain time points. The 8 hour time point was selected to allow time for cell stimulation. The gene regulation comes quickly and the selected time point allows enough time for stimulation and not over/under.
Figure 2F:
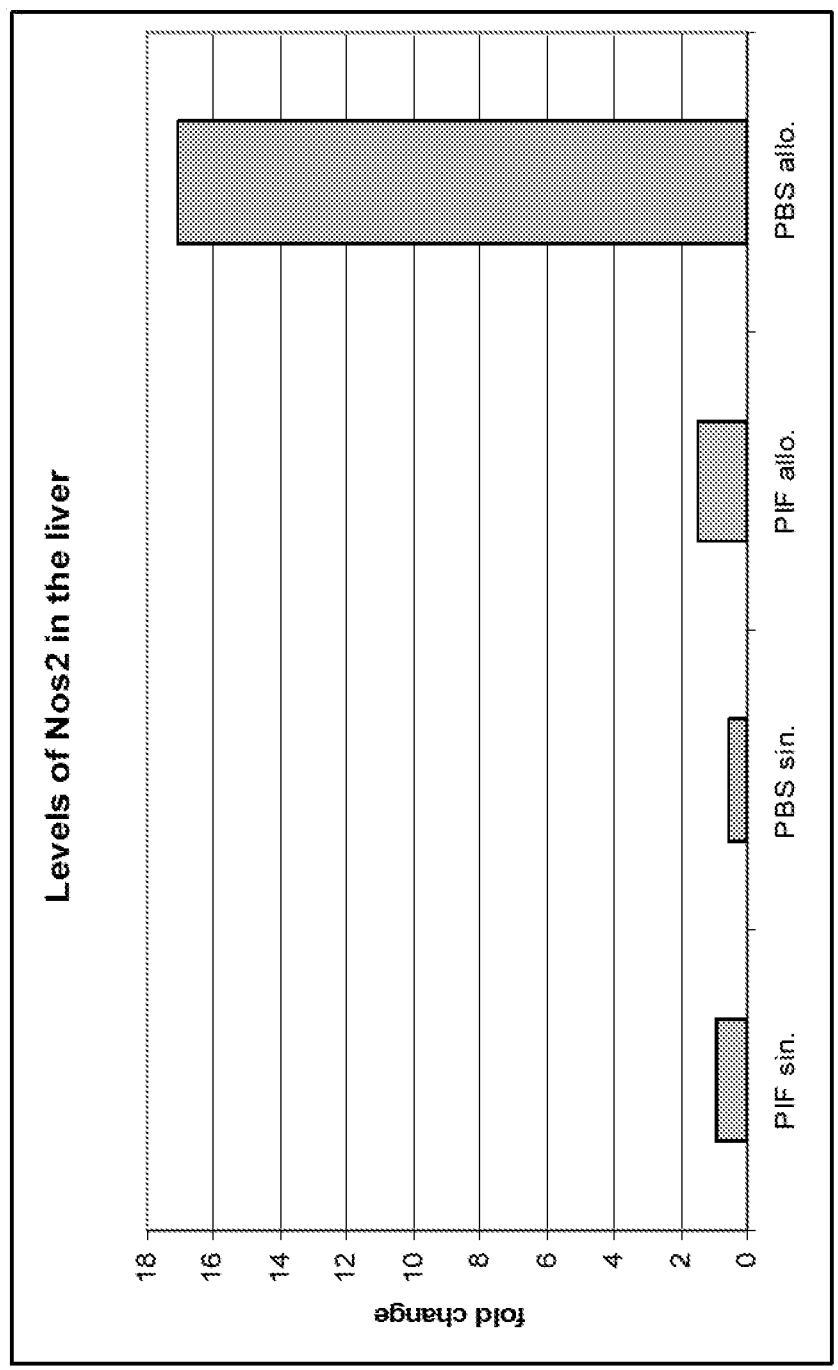
FIG. 2F illustrates PIF reduces Nos2 expression in vivo and NO secretion from RAW, mouse macrophage cell line, in vitro. These results were taken as part of Real-Time quantitative PCR analysis of inflammatory gene expression in the liver using "Mouse Inflammatory Response and Autoimmunity" array. cDNA samples were obtained from livers of normal mice or mice after semi-allogenic (allo.)/singenic (sin.) bone marrow transplantation, treated with PIF or PBS. The expression of Nos2 elevated in semi-allogenic BMT mice, 17 fold comparing with normal mice. PIF completely prevented this elevation.
Figure 2G:
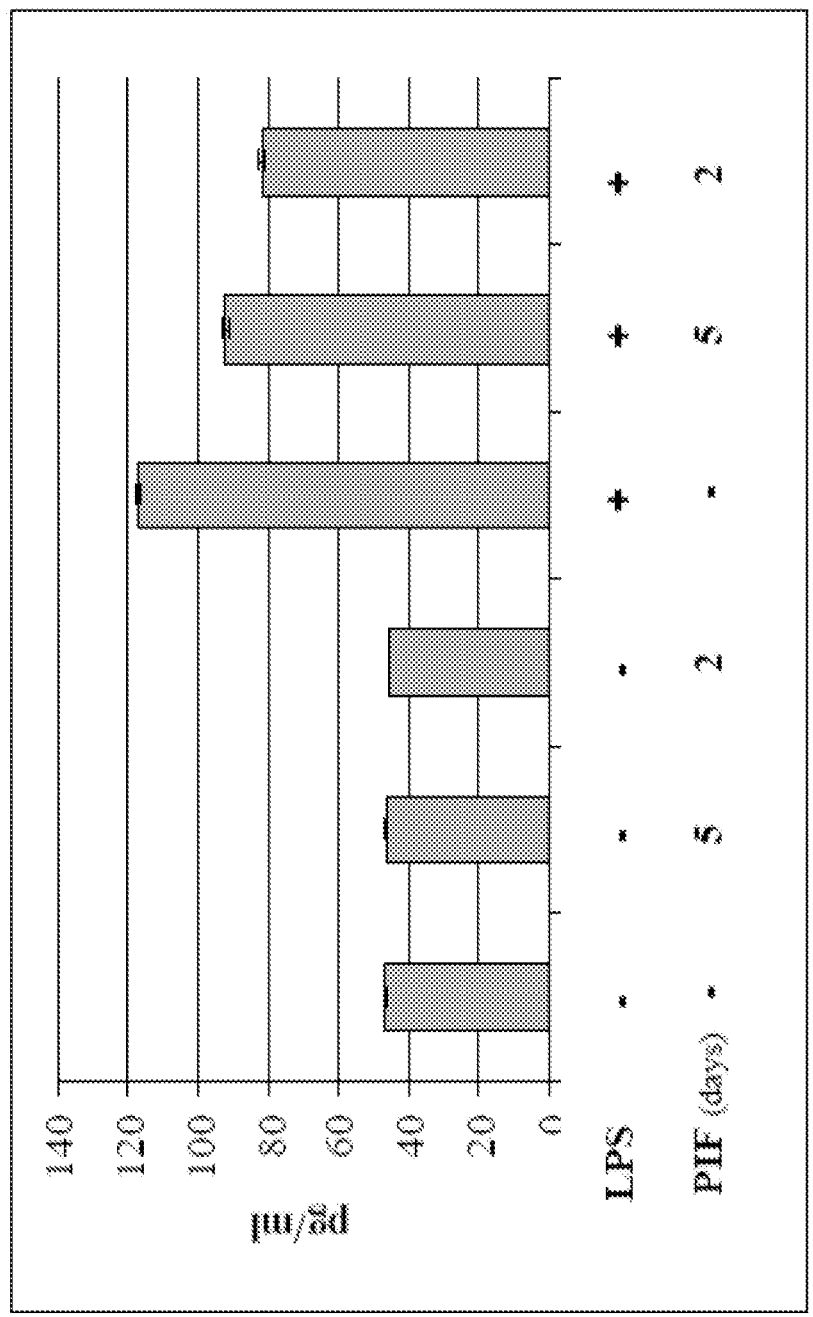
FIG. 2G illustrates RAW (Macrophage cell line) was cultured with 200 nM PIF for different time periods. In the last 24 hours of the experiment, LPS was added to the culture for cell activation. Greiss reagent test was performed to detect NO secretion to the supernatant. PIF was found to reduce NO secretion from RAW.
Figure 3A:
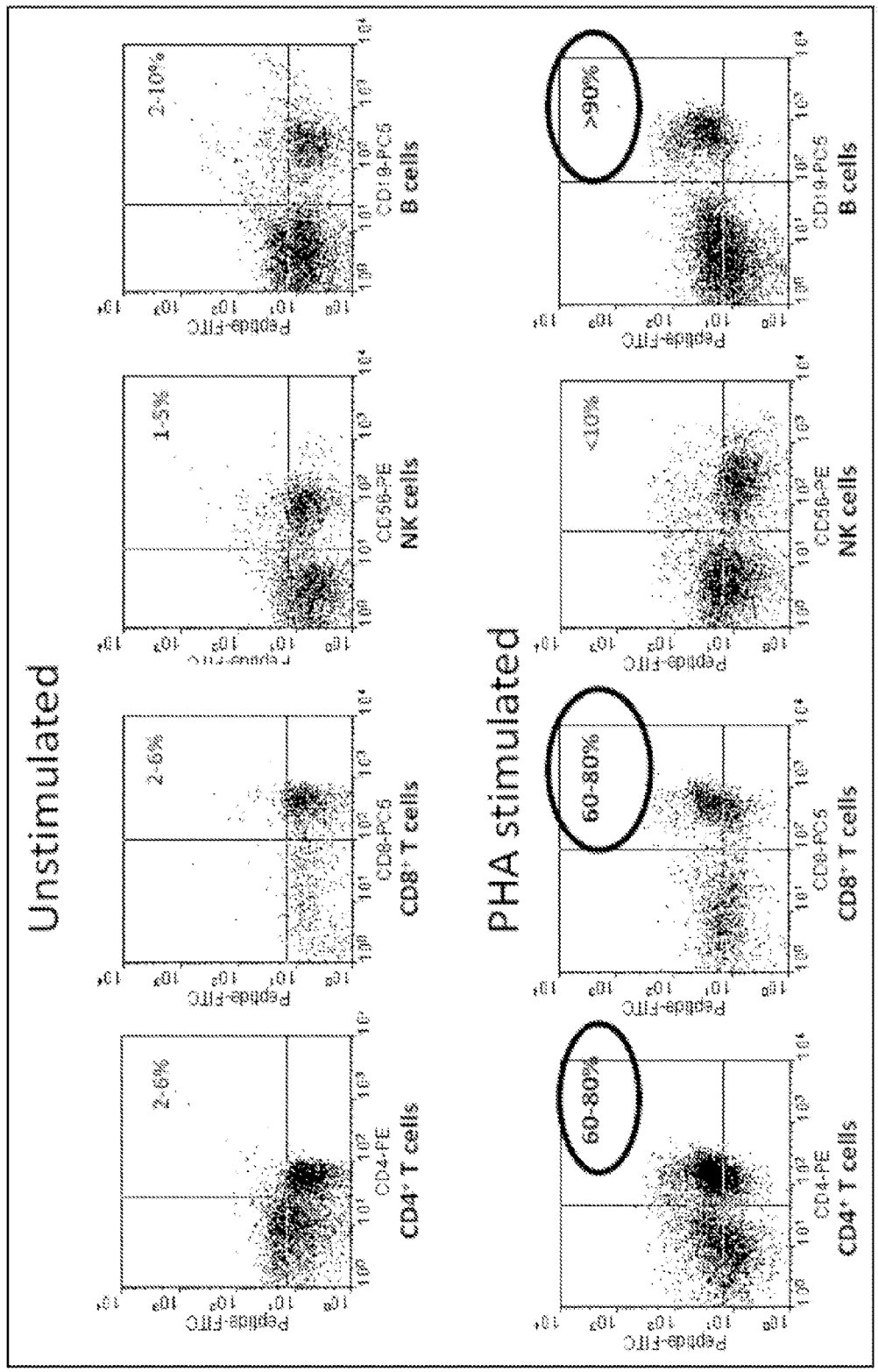
FIG. 3A and FIG. 3B illustrate that mitogen stimulation enhances FITC-PIF binding to T and B cell populations. PBMC were cultured with PHA for 24 h. Binding of FITC-PIF to different PBMC populations was determined by two color flow cytometry. Binding was low (<10% in unstimulated cells a, upper panel from left to right) CD4+, CD8+, NK, (CD56+) and B (CD19+) cells. However, it led to a ~30-fold increase in binding to b (lower panel from left to right), CD4+, CD8+ and B (CD19+) cells. Binding was unchanged for NK cells, even after a 72 hour incubation period.
Figure 3B:
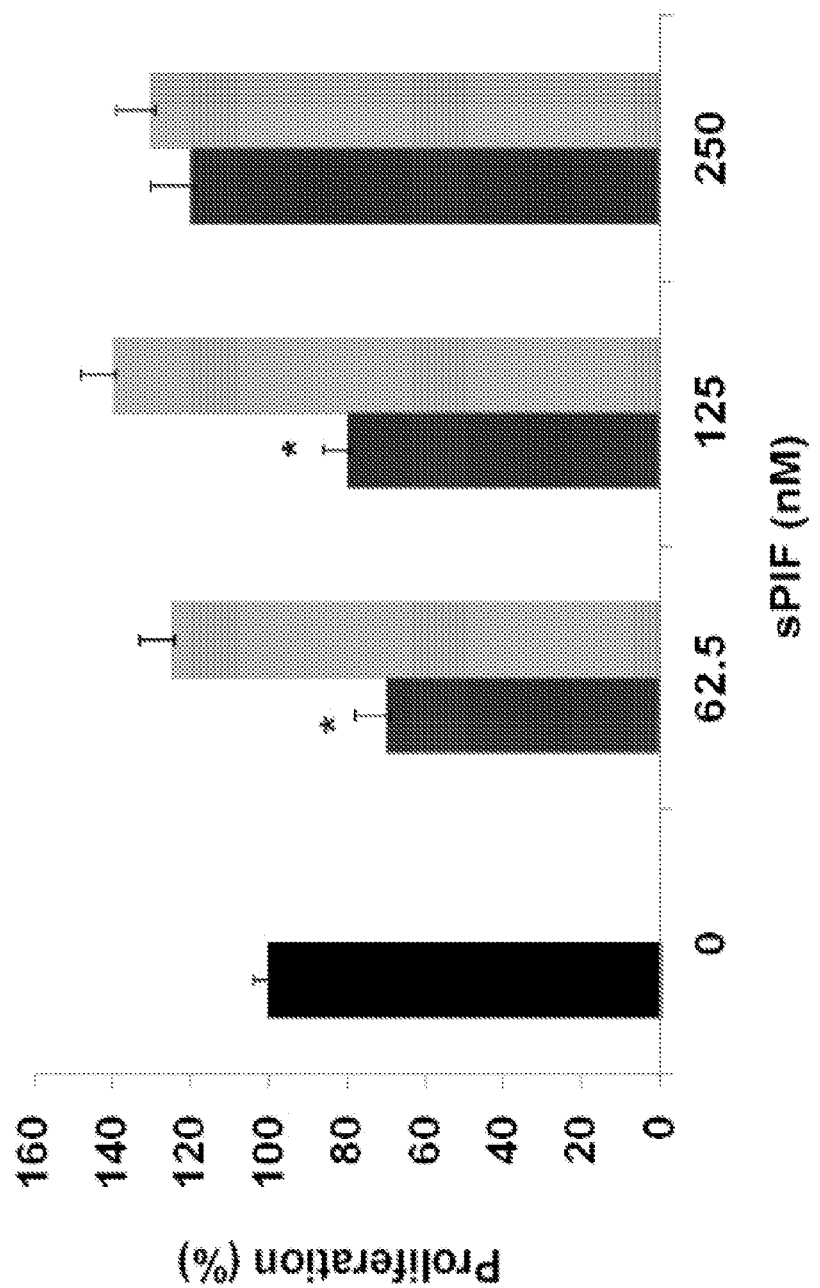
Figures 3C, 3D:
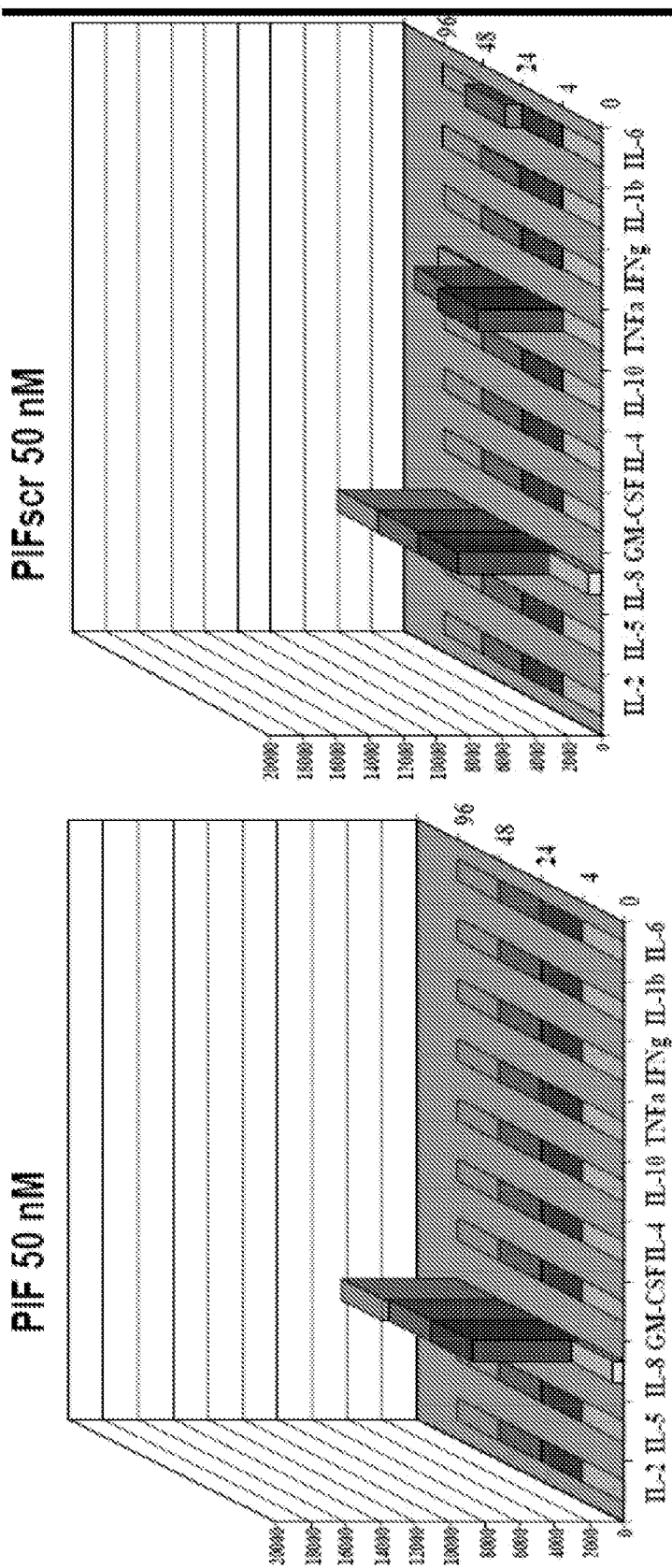
FIG. 3C, FIG. 3D, FIG. 3E, and FIG. 3F illustrate that sPIF promotes $T_H2/T_H1$ cytokine bias in stimulated PBMCs. PBMCs were cultured with +/−sPIF 50 nM+/−anti-CD3-mAb or 50 nM PIF scr+/−anti-CD3-mAb for 4-96 hours.
Figures 3E, 3F:
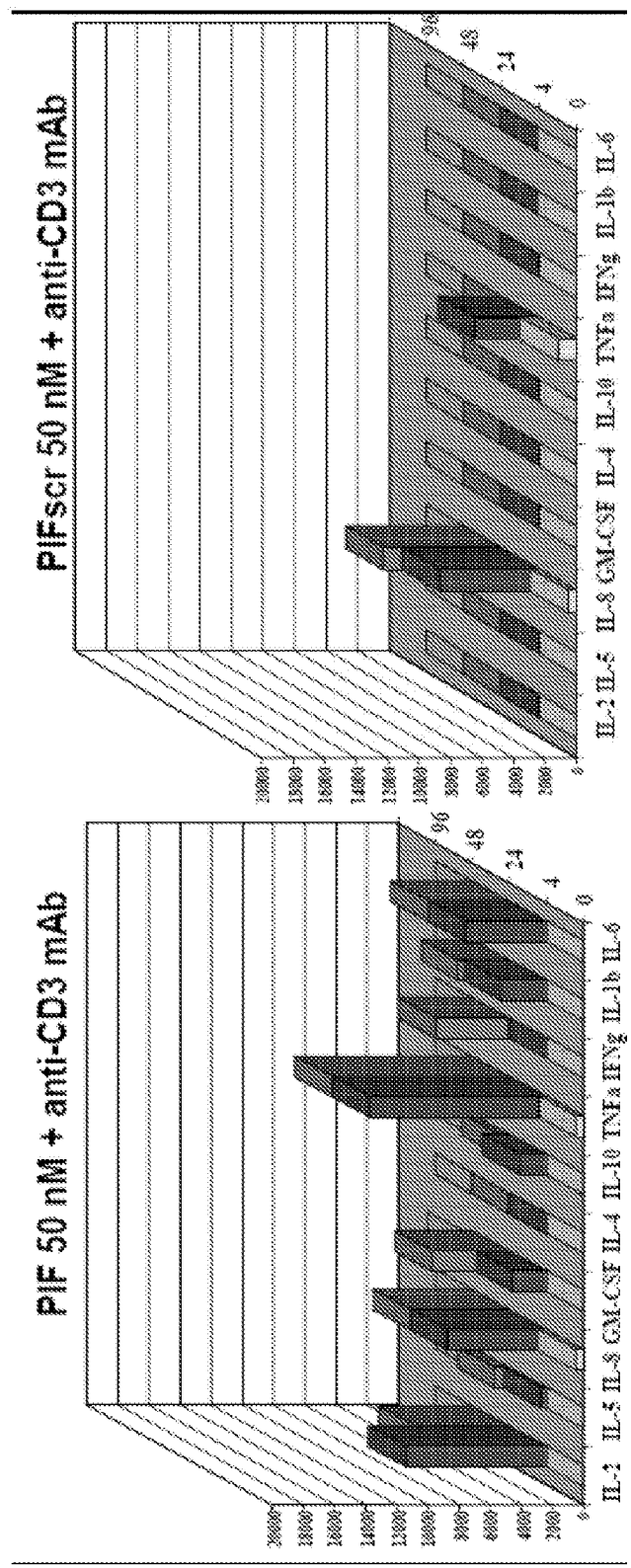
Figure 3G:
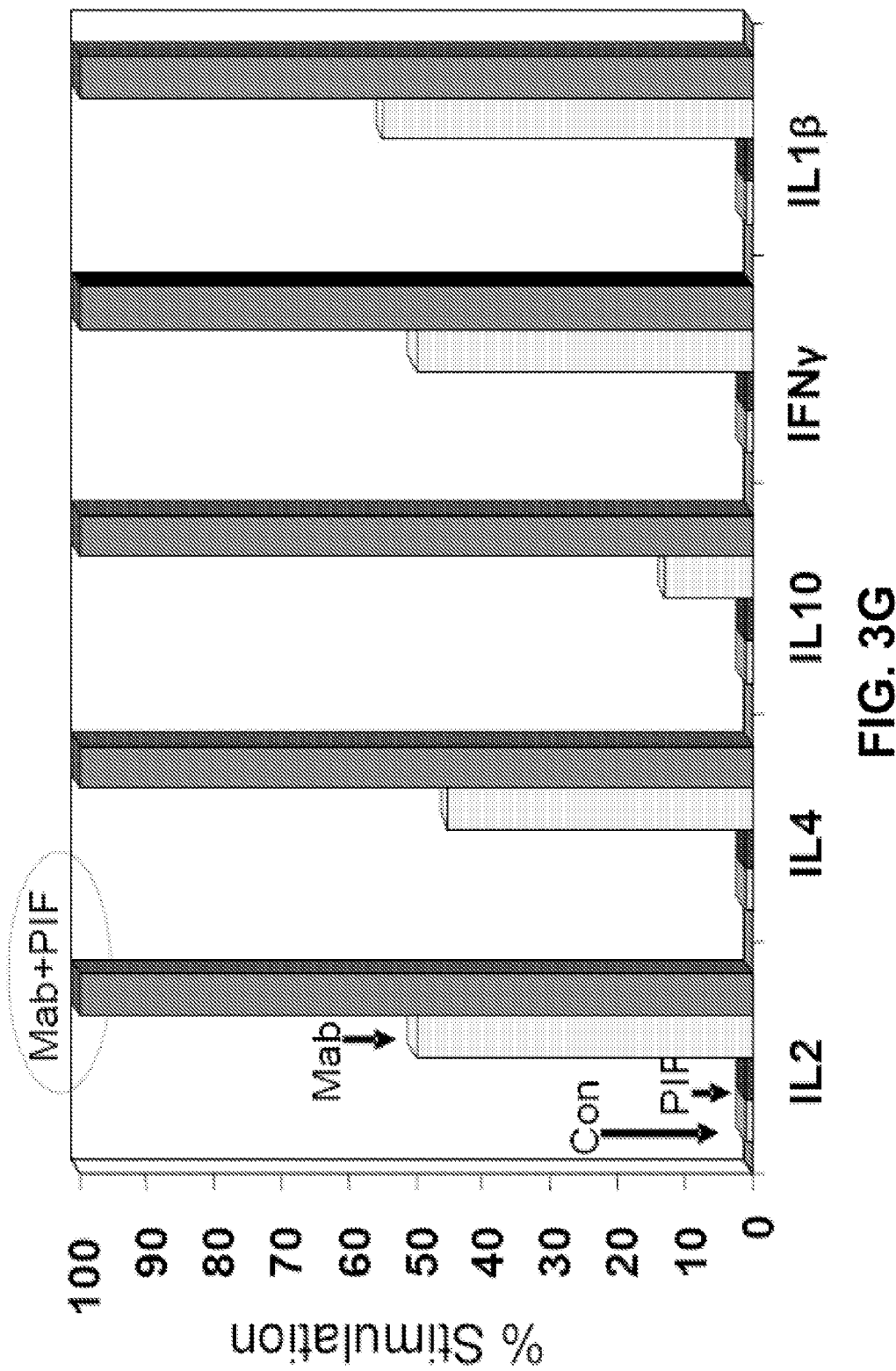
FIG. 3G illustrates the percent stimulation of PBMC cytokines IL2, IL4, IL10, IFNγ, and IL1β when exposed to control, PIF, mAb, and mAb+PIF, respectively.
Figure 4A:
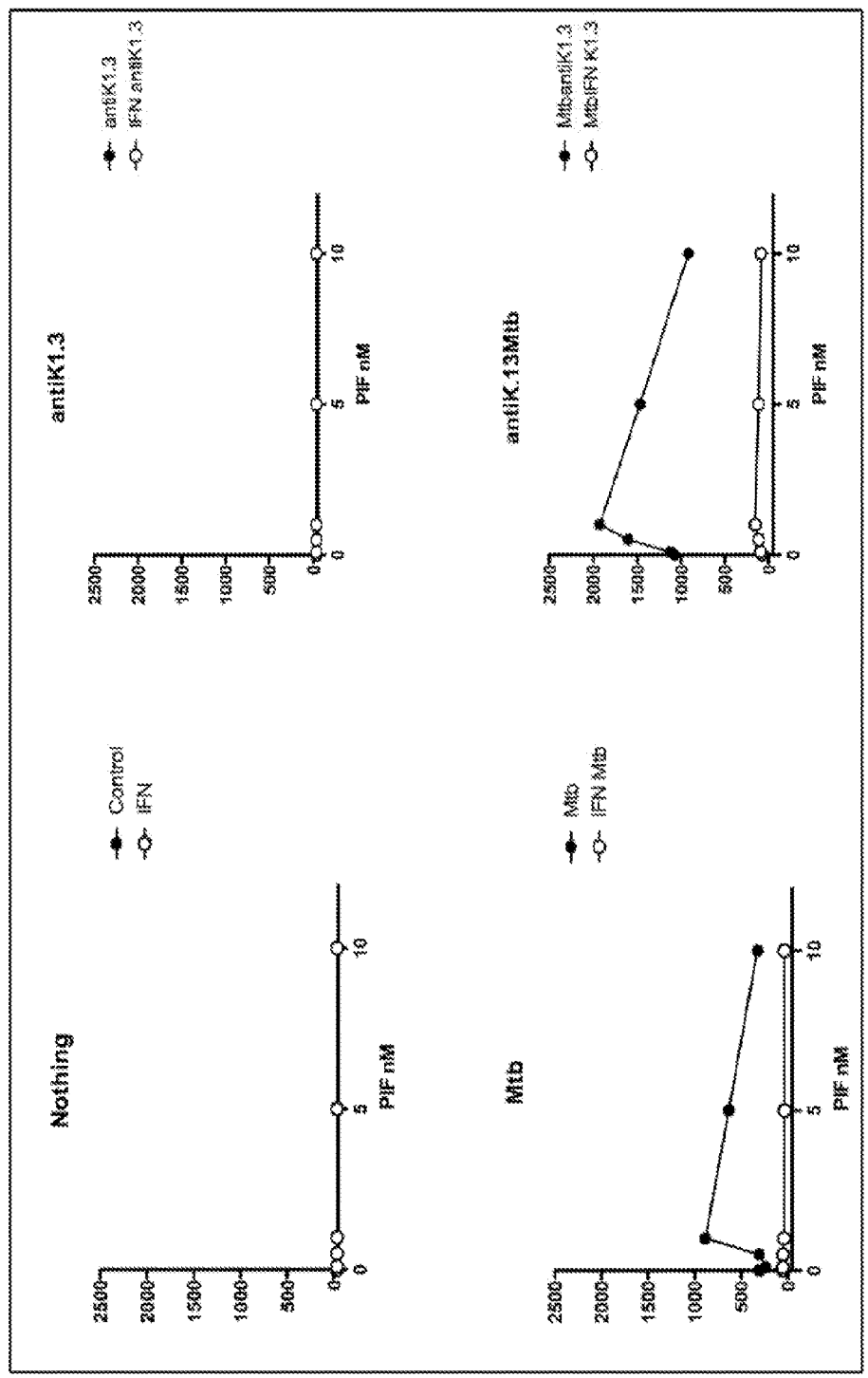
FIG. 4A illustrates that IL-1a was induced by Mtb and was then augmented by PIF and anti-Kv1.3. The response was lost in the presence of IFN.
Figure 4B:
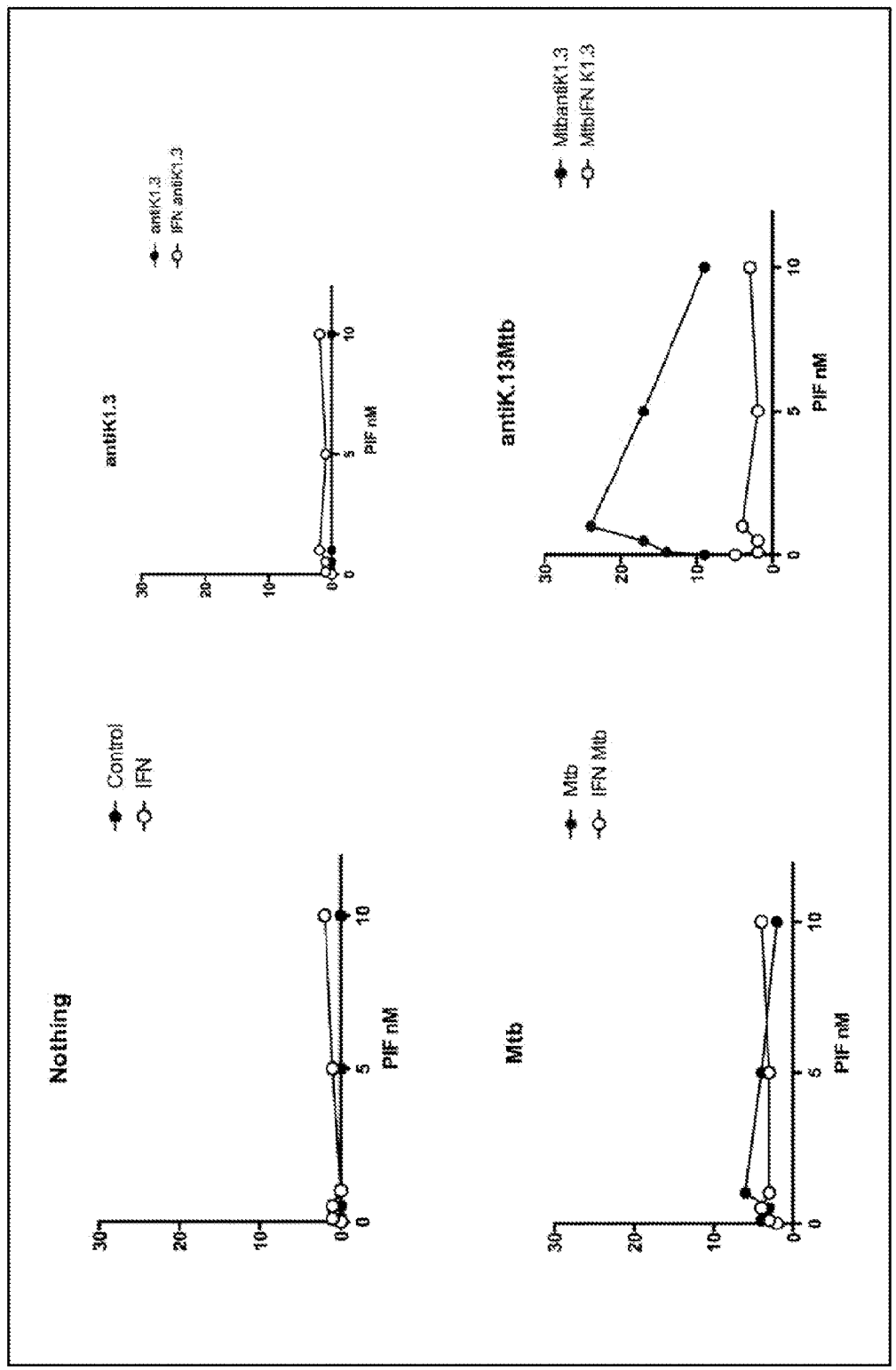
FIG. 4B illustrates IL-1b was induced by Mtb and was then augmented by PIF and anti-Kv1.3. The response was lost in the presence of IFN.
Figure 4C:
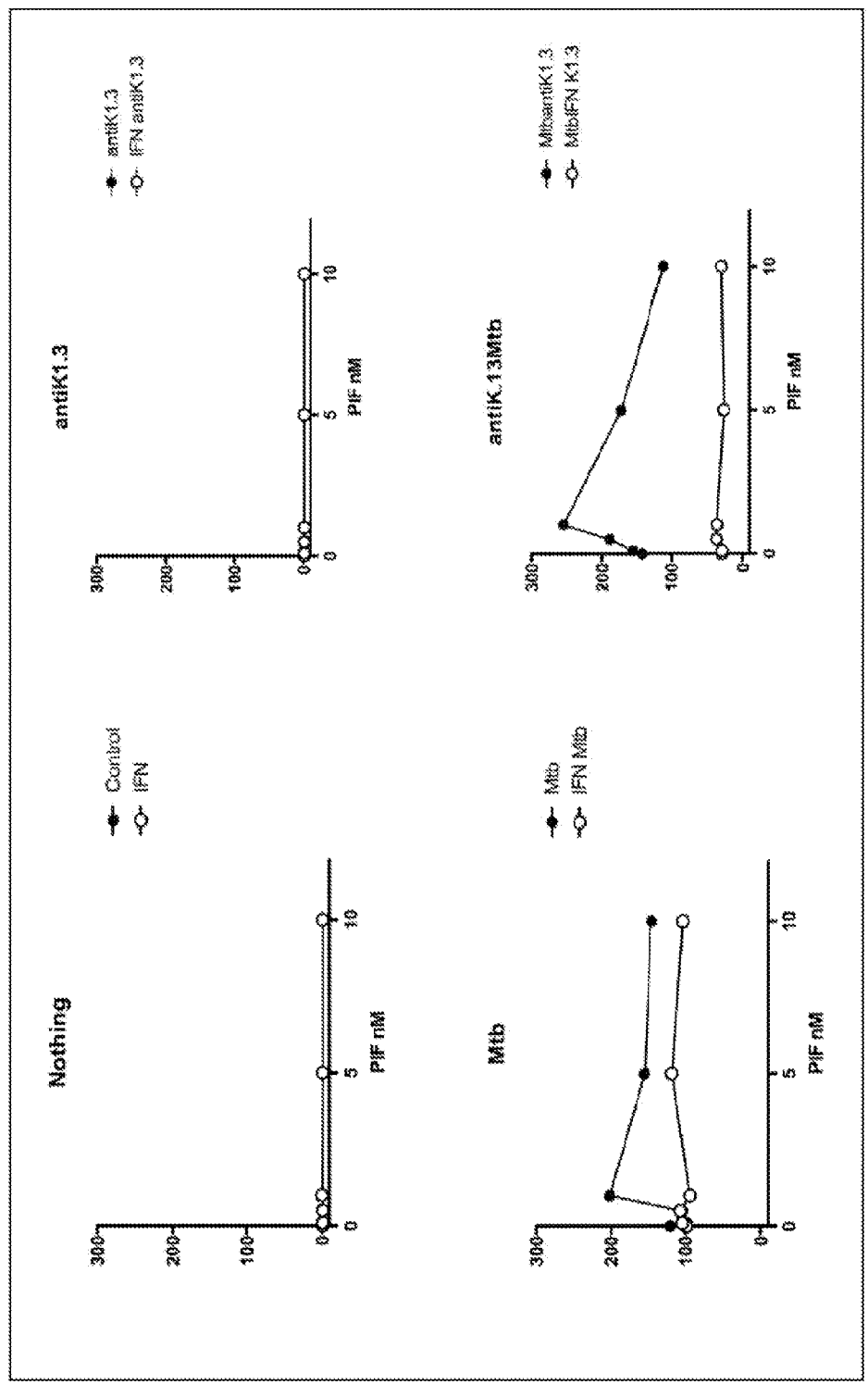
FIG. 4C illustrates (TNF)a was induced by Mtb and was then augmented by PIF and anti-Kv1.3. The response was lost in the presence of IFN.
Figure 4D:
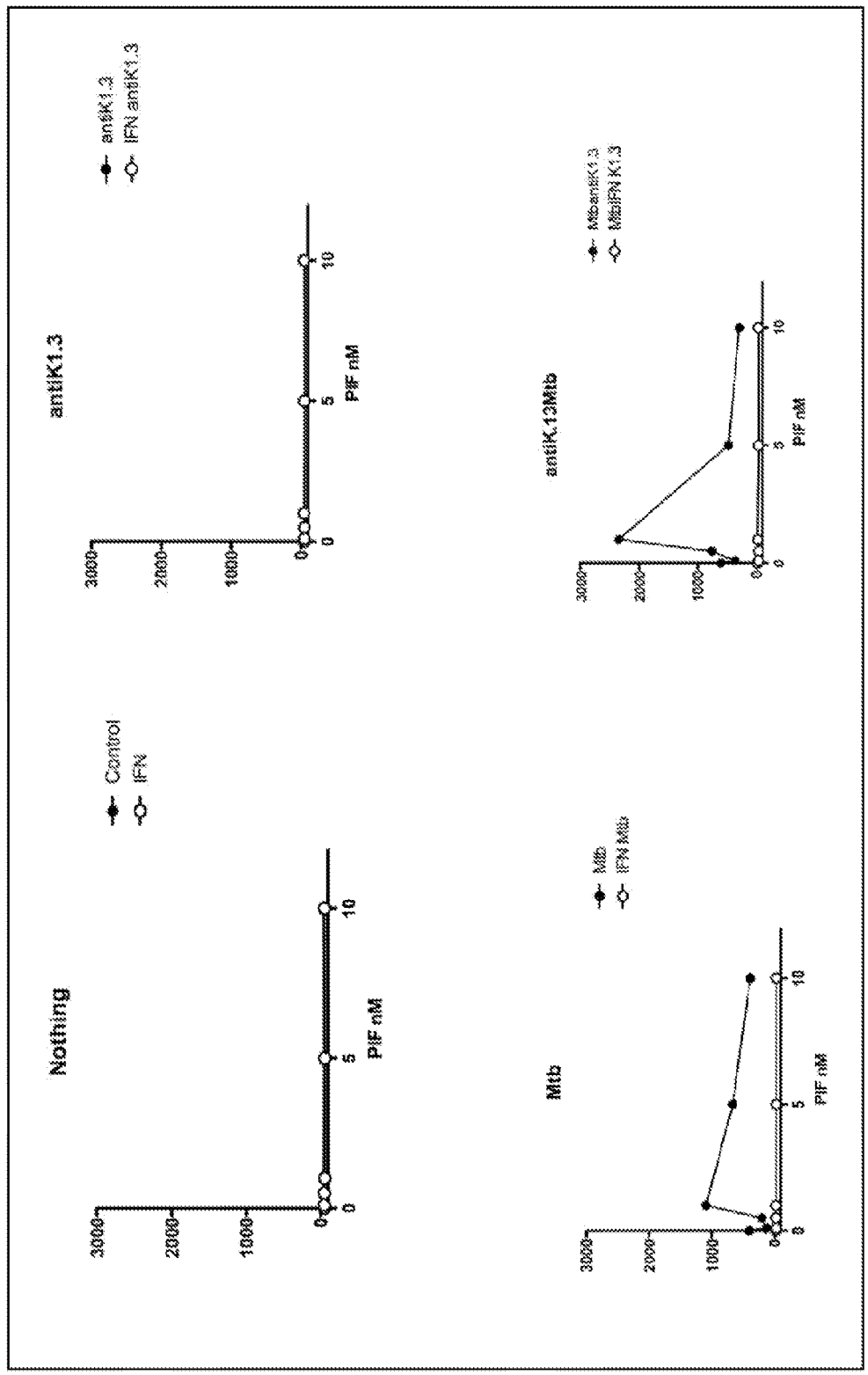
FIG. 4D illustrates MIP-1alpha was induced by Mtb and was then augmented by PIF and anti-Kv1.3. The response was lost in the presence of IFN.
Figure 4E:
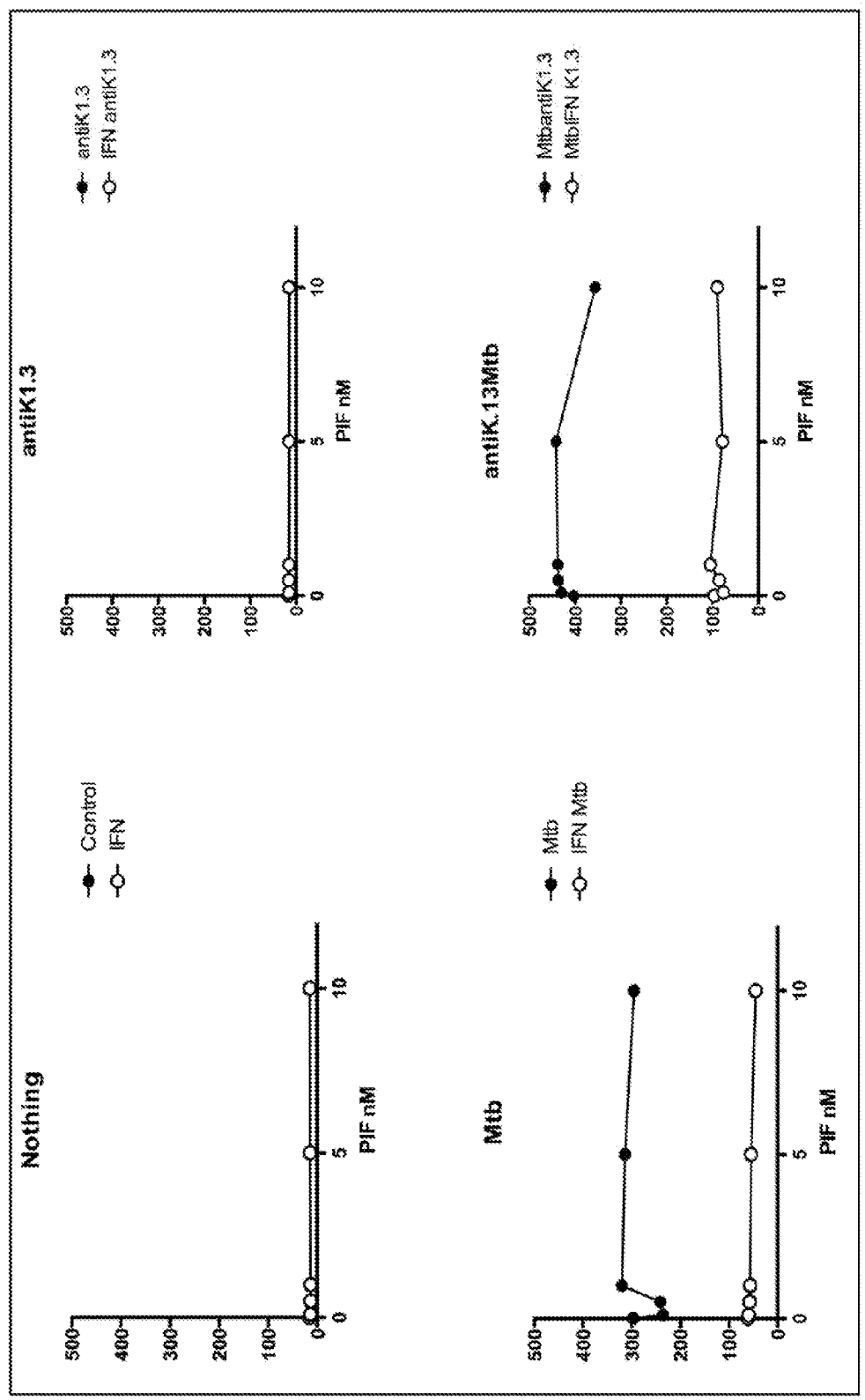
FIG. 4E illustrates KC was induced by Mtb and was then augmented by PIF and anti-Kv1.3. The response was lost in the presence of IFN.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "peptide" is a reference to one or more peptides and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with preimplantation factor (PIF), can include, but is not limited to, providing PIF into or onto the target tissue; providing PIF systemically to a patient by, e.g., intravenous injection whereby the therapeutic reaches the target tissue; providing PIF in the form of the encoding sequence thereof to the target tissue (e.g., by so-called gene-therapy techniques). "Administering" a composition may be accomplished by parenteral, oral or topical administration, or by such methods in combination with other known techniques. Such combination techniques include heating, radiation and ultrasound.

The term "animal" or "patient" or "subject" as used herein includes, but is not limited to, humans and non-human vertebrates such as wild, domestic and farm animals. Preferably, the term "animal" or "patient" or "subject" refers to humans.

The term "improves" is used to convey that the present invention changes either the appearance, form, characteristics and/or the physical attributes of the tissue to which it is being provided, applied or administered. The change in form may be demonstrated by any of the following alone or in combination: treatment of an infection/inflammation as the result of a disease such as *Listeria monocytogenes* infection, malaria, Lyme disease, cardiovascular disease, duodenal peptic ulcer, atherosclerosis, peritonitis and tuberculosis; alleviation of symptoms of a disease; increase in granuloma formation; increase in cytokine secretion; increase in secretion of perforin and granulysin; modulation of disease-infected phagocytes' cytokine/chemokine secretion; and decrease in dissemination of bacteria.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, the term "therapeutic" means an agent utilized to treat, combat, ameliorate, prevent or improve an unwanted condition or disease of a patient. In part, embodiments of the present invention are directed to methods of treating tuberculosis.

A "therapeutically effective amount" or "effective amount" of a composition is a predetermined amount calculated to achieve the desired effect, i.e., to reduce, inhibit or improve the symptoms of the disease or condition. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of embodiments of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

*Listeria monocytogenes*, a Gram-positive facultative intracellular bacterium, survives and replicates in the cytoplasm of phagocytes and hepatocytes following escape from the phagosome. The innate immune response to *Listeria* infection is a complicated process involving not only many cell types, including macrophages, chemokines (MIP)-1a and KC, natural killer (NK) cells and neutrophils, but also nitrogen intermediates and cytokines such as tumor necrosis factor (TNF)-a, interleukin (IL)-1, IL-6, IL-12, interferon (INF)-c, and the more recently identified early T lymphocyte activation (Eta)-1. It is widely believed that TNF-a and nitric oxide (NO), an end product of inducible nitric oxide synthase (iNOS) produced by macrophages and a newly identified TNF/iNOS-producing dendritic cell (Tip-DC), may be key effector molecules responsible for the protection of the host from early *Listeria* infection in conjunction with INF-c, which is mainly secreted by NK cells. Numerous studies also indicate that the CD8+ T-cell immune response may play a prominent role in the complete clearance of *Listeria monocytogenes* in infected mice through IFN-α-mediated mechanisms whereby escape of *L. monocytogenes* from the phagosome is inhibited and macrophages are activated. Furthermore, CD4+ T cells may also be engaged in antilisterial resistance by providing CD8+ T cells with B7-1/B7-2-mediated costimulation by DCs through the CD40-CD40L interaction, and by polarizing the immune response towards a T helper type 1 (Th1) pathway. Specifically, B7-1 and B7-2 costimulatory molecules may be necessary for the production of IFN-α and IL-2 from Th1 CD4+ T cells during *Listeria* infection. B7-H1 (also known as CD274 and PD-L1) is a member of the B7 family that positively or negatively controls Tcell receptor (TCR)-mediated signaling. The findings of a series of in vivo studies using either the antagonistic anti-B7-H1 antibody or gene knockout mice support the coinhibitory role of endogenous B7-H1; for example, in vivo blockade of B7-H1 with antagonistic monoclonal antibody (mAb) may activate effector T cells, leading to an increase in the incidence of autoimmune diabetes in non-obese diabetic (NOD) mice, hapten-induced contact hypersensitivity in normal mice, and susceptibility to experimental autoimmune encephalomyelitis in B7-H1 knockout mice. However, the findings that transgenic expression of B7-H1 by b-islet cells induces spontaneous diabetes and accelerates the rejection of b-islet cells in allogeneic hosts, and that the antagonistic antibody to B7-H1 inhibits the pathogenesis of inflammatory bowel disease, suggest that B7-H1 plays a costimulatory role in T-cell immunity in vivo. While B7-H1 has been implicated in T-cell immunity in cancer progression, autoimmunity and graft rejection in many studies, there are few reports elucidating the role of endogenous B7-H1 in infection models.

Tuberculosis (TB), caused by bacilli *Mycobacterium tuberculosis* (Mtb), is a serious and life threatening disease which infects about 8 million and kills 3 million people annually worldwide. Mtb invades and replicates within the endosomes of alveolar macrophages, altering their activity.

Localized immune suppression within mononuclear cell granulomas develops following Mtb infection. Macrophages, T lymphocytes, B lymphocytes and fibroblasts are among the cells that aggregate to form a granuloma, with lymphocytes surrounding the infected macrophages. The granuloma functions not only to prevent dissemination of the mycobacteria, but also provides a local environment for communication of cells of the immune system. Within the granuloma, T lymphocytes secrete cytokines such as interferon (IFN)-gamma, which activates macrophages to destroy the bacteria with which they are infected. Cytotoxic T cells can also directly kill infected cells, by secreting perforin and granulysin. Importantly, Mtb may survive in granulomas by going into a latent state.

Lyme disease, which is also known as Lyme borreliosis, is the most common tick-borne infectious disease in the northern hemisphere. Lyme disease is caused by at least three species of bacteria belonging to the genus *Borrelia*. The bacterium *Borrelia burgdorferi* sensu stricto causes most cases of Lyme disease in the United States, whereas *Borrelia afzelii* and *Borrelia garinii* cause most cases of Lyme disease in Europe. *Borrelia* is transmitted to humans by the bite of infected ticks belonging to a few species of the genus *Ixodes* ("hard ticks"). Early symptoms may include fever, headache, fatigue, depression, and a characteristic circular skin rash called erythema migrans (EM). Left untreated, later symptoms may involve the joints, heart, and central nervous system.

Atherosclerosis, which is also known as arteriosclerotic vascular disease (ASVD), is a condition noted by vascular wall thickening. The thickening is generally a result of an accumulation of fatty materials such as cholesterol, which form hard structures called plaques. Recent clinical and experimental evidence indicates that inflammatory processes in the vascular wall are the decisive factor that accounts for the rate of lesion formation and clinical development in patients suffering from atherosclerosis. Evidence has further indicated that recruitment of monocytes to, as well as the retention of monocytes within, the atherosclerotic lesions contributes to the progression of plaque development.

Mammalian pregnancy is a unique physiological event in which the maternal immune system interacts with the fetus in a very efficient manner, which is beneficial for both parties. Pregnancy is an immune paradox, displaying no graft vs. host or host vs. graft effect. Pregnancy is an immune-modulatory state which provides such desired effective immune protection (modulation without suppression). In it, vertical transmission of TB infection from mother/host to newborn/allograft is low, analogous to the protection observed against HIV and various immune disorders such as multiple sclerosis. Without wishing to be bound by theory, it is believed that activation of the host's immune system could be instrumental in the treatment of tuberculosis and embryo-specific protective compounds could have such a pivotal protective role against tuberculosis. Successfully transposing pregnancy's immune-modulatory effects to the non-pregnant immune state may result in a powerful, effective, nontoxic tool to control TB. Thus, having an agent that may act in synergy with anti-TB agents may represent a critical supportive element in the protection against this serious disease.

A novel pre-implantation factor (PIF) is an early (two-cell stage) message from the embryo/allograft to mother/host. PIF creates immune tolerance and acceptance while playing an essential role in responding as needed to pathogen challenge. The synthetic analog of PIF (sPIF) replicates the native peptide's effect on activated peripheral blood mononuclear cell (PBMC) proliferation and cytokine secretion, acting through novel sites on PBMC and having an effect which is distinct from known immune-suppressive drugs. As used herein PIF or PIF peptide is a synethetic PIF peptide or an isolated, naturally occurring PIF peptide. PIF's protective effect occurs throughout viable pregnancy without affecting the host's basal immunity. sPIF mimics its physiologic counterpart, enhances activated immunity "per need" both to prevent and regress ongoing immune injury without interfering with basal immunity required for survival. Thus, PIF controls inflammation without broad immunosuppression. Localized immune suppression within mononuclear cell granulomas develops following Mtb infection. Accordingly, PIF may prove useful in treatment of TB. Therefore, it is believed that PIF may target the Kv1.3 potassium channel, an anti-TB target.

While not wishing to be bound by theory, sPIF blocks activated PBMCs proliferation, creates a TH2/TH1 cytokine bias and promotes pro-tolerance while reducing pro-rejection genes. This is achieved by binding PIF to macrophages and in activated cells to T and B cells presumably acting through K+(not Ca++) channels used by immune suppressive agents. Within the pregnant uterus, PIF accumulates within NK cells, which mitigates maternal hostility. Hence, embryo-secreted PIF modulates both peripheral and local immunity, creates a favorable environment for the embryo for implantation and facilitates trophoblast invasion, thus revealing an essential role of the peptide in promoting pregnancy.

The observed biphasic binding and effect of PIF on immune cells provides interesting insights into pregnancy-related tolerance. The present study clearly has shown differences in PIF's effect on stimulated (challenged) and immune naïve cells. The decrease noted in MLR, following exposure to sPIF, reflects a diminished allo-antigenic response. This may explain why donor embryos (allogenic) can successfully implant, and genetic similarity or same species breeding is not necessary. PIF necessarily maintains basal immunity required for survival, and aids in tolerance for self by blocking activated T cells proliferation that would harm the embryo.

The differential effect of sPIF on naïve or stimulated, or even co-stimulated PBMCs is also evident on cytokines. In the former circumstance, sPIF reduced pro-inflammatory TH1 response, while following stimulation of PMBCs, sPIF created a TH2 cytokine bias. Increased levels of TH1 and TH2 cytokines in pregnancy were recently reported. Decrease in IL-2 and (associated genes) a prime inducer of cytotoxic T cells proliferation and TNF-family member was noted in naïve cells, while CCL7, a regulator of monocyte function, increased. In stimulated cells, since there is a need to respond to pathogens, potent TH1 cytokines (IFN$\gamma$ and TNF$\alpha$) increased. The divergent effects on IL10 secretion and gene expression (decrease in naïve and increase in activated cells) indicate that PIF prevents deleterious immune suppression under basal conditions while protecting against rejection when maternal immunity is under challenge.

Global PMBCs gene expression data further corroborated PIF-induced differences between basal and challenged environments. In the former, pro-tolerant genes increased while those that promote embryo rejection were reduced. Remarkably, under co-stimulation, the anti-rejection genes had to be balanced by promoting defense mechanisms required to fight disease. Both naïve and stimulated cells increased TGFBRII expression. TGF$\beta$ binding inhibited T cells proliferation and prevented macrophage activation. sPIF increased FKBP1, the FK506 binding protein, involved in the calcineurin pathway critical for tolerance induction. Of interest, that the same gene was also up-regulated in human decidua following sPIF exposure. In stimulated cells, sPIF promoted tolerance by increasing IDO that degrades L-tryptophan induced by IFNγ and cyclophylin B, a tolerance inducing molecule where cyclosporin binds. The increase noted in HLA-G3 expression mitigates immune cells attack on the embryo. On the other hand, facilitating maternal immune response sPIF increased two tyrosine kinases, LCK, which plays a key role in TCR-linked signal transduction pathways and Fyn, which is involved in control of cell growth. The reduction in CD31 reflects a decrease in neutrophil action, as does the decrease in CCR4, a pro-inflammatory chemokine. Overall, the gene data further substantiate dual comprehensive modulatory effects of PIF which result in balancing tolerance with supporting maternal immunity to combat disease.

The differential FITC-sPIF binding profile to subsets of naïve (CD14+) or stimulated PBMC (T and B) is in line with the observed immune modulatory effects. Innate immunity is readily preserved to avoid attack on the embryo. The enhanced binding to T and B cells at high ligand concentrations and in activated PBMCs at low concentration reflect effective interaction with the adaptive arm of the immune system. PIF also binds to Treg (FoxP3+) activated T cells subtype while only a limited binding to NK+ cells observed under mitogen challenge reflecting target specificity. Thus, PIF binding properties further support the observed differences on innate and adaptive immunity.

sPIF mechanism is unique, not exerted through calcium mobilization, binding to GPCR/Gq receptors seen with immune suppressive drugs (cyclosporine, FK506) since PIF has no effect alone or PBMC activated by PHA or PMA/Ionomycin. However PIF synergizes with anti-CD3 mAb to stimulate IL-2 a major product of calcineurin signaling, while also promoting FK506 binding protein up-regulation, suggesting a downstream involvement in this pathway. Recent data together with current study implicates K+ channels in the PIF-induced observed effects. PIF binds to Kv1.3 beta-channels that modulate the ion pore and gene expression data demonstrates modulation of K+ genes.

Beyond peripheral immunity, local uterine immunity may also need to be controlled to achieve successful reproduction. Embryo-secreted PIF may be localized within granules of murine uNK cells at the maternal-fetal interface, possibly, targeting intra cellular binding sites. PIF, derived from the surrounding trophoblastic cells rapidly diffuse into uNK cells. Thus, PIF may down-regulate uNK cytotoxic functions or modulate cytokine secretion to support the conceptus' survival. At the point when direct embryo-maternal interaction takes place during implantation, PIF plays a significant role in concert with other pro-implantation elements.

PIF may have an essential orchestrating role in creating a perfect immune balance, through a contradictory "immune paradox" profile that is only observed in pregnancy. The increase in TH2 cytokines coupled with binding to Treg cells may protect the embryo while the increase in TH1 cytokines under challenge may protect against infection. PIF expression shortly post-fertilization may reflect its dominant role in early pregnancy events.

Embodiments described herein are directed to the use of PIF for the treatment of intracellular damage. Embodiments are directed to a method of treating intracellular damage comprising administering a PIF peptide to a subject in need thereof. In some embodiments, the PIF administered may increase cytokine secretion in response to intracellular damage. In some embodiments, PIF may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, the PIF administered is in a therapeutically effective amount. In some embodiments, a subject is diagnosed with intracellular damage. In some embodiments, the subject is at risk for intracellular damage. In some embodiments, the intracellular damage may be the result of a disease. In some embodiments, the disease is caused by an intracellular bacterium. In some embodiments, the intracellular bacterium may be selected from *Listeria monocytogenes, Mycobacterium tuberculosis, Heliobacter pylori, Borrelia burgdorferi* sensu stricto, *Borelia afzelii*, and *Borrelia garinii*. In further embodiments, the disease may be selected from *Listeria*, malaria, Lyme disease, cardiovascular disease, duodenal peptic ulcer, atherosclerosis, peritonitis and tuberculosis. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years. In some embodiments, the method may further comprise administering PIF in combination with other anti-intracellular damage agents.

In embodiments of the present disclosure, methods of treating atherosclerosis in a subject comprising administering a PIF peptide are provided. In some embodiments, PIF may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, a therapeutically effective amount of PIF is administered. In some embodiments, a subject is diagnosed with atherosclerosis. In some embodiments, the subject is at risk for atherosclerosis. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years. In some embodiments, the method may further comprise administering PIF in combination with other anti-atherosclerotic agents.

In some embodiments, PIF may treat atherosclerosis by reducing plaque in the aortic root. In some embodiments, PIF may treat atherosclerosis by reducing plaque in the aortic arch. In some embodiments, PIF may treat atherosclerosis by reducing a monocyte protein in the aortic arch. In further embodiments, the monocyte protein may be selected from vascular cell adhesion molecules (VCAM-1), monocyte chemotactic proteins (MCP-1) and clusters of differentiation (CD68). In some embodiments, PIF may treat atherosclerosis by reducing a monocyte protein in the aortic root. In further embodiments, the monocyte protein may be selected from vascular cell adhesion molecules (VCAM-1), monocyte chemotactic proteins (MCP-1) and clusters of differentiation (CD68). In some embodiments, PIF may treat atherosclerosis by reducing lipids in the aortic root. In some embodiments, PIF may treat atherosclerosis by reducing a cytokine in THP-1 cells. In further embodiments, the cytokine may be selected from interleukein 12, subunit beta (IL-12b) and interferon gamma (IFN-γ). The effect on plaque reduction on the aorta is direct without affecting circulating lipids. In embodiments, the level of circulating lipids is not substantially affected or otherwise substantially reduced.

In embodiments of the present disclosure, methods of treating tuberculosis in a subject comprising administering a PIF peptide are provided. In some embodiments, methods of treating tuberculosis may comprise decreasing dissemination of *Mycobacterium tuberculosis* comprising administering a PIF peptide. In some embodiments, methods of treating tuberculosis may comprise increasing cytokine secretion in response to *Mycobacterium tuberculosis* infection comprising administering a PIF peptide. In some embodiments, the PIF peptide may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, a therapeutically effective amount of a PIF peptide is administered. In some embodiments, the subject is diagnosed with tuberculosis. In some embodiments, the subject is at risk for tuberculosis infection. In some embodiments, the subject has been exposed to *Mycobacterium tuberculosis*. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or, preferably, oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years. In some embodiments, the method may further comprise administering PIF in combination with other anti-TB agents.

In embodiments of the invention, methods of treating the symptoms of tuberculosis in a subject comprising administering a PIF peptide are provided. In such methods, the symptoms of tuberculosis may be selected from chest pain, cough, weight loss, energy loss, poor appetite, fever, night sweats, chills and combinations thereof. In some embodiments, the PIF peptide may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, a therapeutically effective amount of a PIF peptide is administered. In some embodiments, the subject is diagnosed with tuberculosis. In some embodiments, the subject is at risk for tuberculosis infection. In some embodiments, the subject has been exposed to *Mycobacterium tuberculosis*. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years. In some embodiments, the method may further comprise administering PIF in combination with other anti-TB agents.

In embodiments of the present disclosure, methods of treating peritonitis in a subject comprising administering a PIF peptide are provided. In some embodiments, PIF may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, a therapeutically effective amount of PIF is administered. In some embodiments, a subject is diagnosed with peritonitis. In some embodiments, the subject is at risk for peritonitis. In some embodiments, the PIF peptide is coadministered with a potassium channel inhibitor. In further embodiments the potassium channel inhibitor may be selected from IFNγ, Kv1.3 inhibitor and combinations thereof. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years. In some embodiments, the method may further comprise administering PIF in combination with other anti-atherosclerotic agents.

Embodiments are directed to a method of upregulating B7-H1 comprising administering a PIF peptide to a subject in need thereof. In some embodiments, B7-H1 may positively control T-cell receptor-mediated signaling. In other embodiments, B7-H1 may negatively control T-cell receptor-mediated signaling. Some embodiments may be directed to methods of inhibiting a Kv1.3 channel comprising administering a PIF peptide to a subject in need thereof. Some embodiments may be directed to methods of inhibiting a Kv1.3 channel further comprising administering a Kv1.3 inhibitor to a subject in need thereof. In some embodiments, the administration of PIF peptide blocks the activity of the Kv1.3 potassium channel. In some embodiments, the PIF peptide blocks the activity of the Kv1.3 channel by binding to the channel. In some embodiments, the PIF peptide may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, a therapeutically effective amount of a PIF peptide is administered. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years.

Embodiments are directed to a method of treating inflammation from intracellular damage comprising administering a PIF peptide to a subject in need thereof. Some embodiments may be directed to methods of increasing cytokine secretion in response to intracellular damage comprising administering PIF to a subject in need thereof. Some embodiments may be directed to methods of increasing cytokine secretion in response to intracellular damage further comprising administering a Kv1.3 inhibitor to a subject in need thereof. In some embodiments, the PIF peptide may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, a therapeutically effective amount of a PIF peptide is administered. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years.

In some aspects, a method of decreasing dissemination of tuberculosis bacteria comprising administering PIF to a subject in need thereof. In some embodiments, the PIF administered is in a therapeutically effective amount. In some embodiments, the PIF peptide may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years.

Further embodiments are directed to the use of PIF to neutralize local immune suppression induced by Mtb-infected macrophages and/or increase host's immune response against Mtb infection. In some embodiments, the PIF peptide may be selected from SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8. In embodiments, the PIF peptide is selected from SEQ ID NO: 1; SEQ ID NO: 2; SEQ ID NO: 3; SEQ ID NO: 4. In other embodiments, the PIF peptide is selected from SEQ ID NO: 1; SEQ ID NO: 2; SEQ ID NO: 3. In some embodiments, a therapeutically effective amount of a PIF peptide is administered. In some embodiments, the subject is diagnosed with tuberculosis. In some embodiments, the subject is at risk for tuberculosis infection. In some embodiments, the subject has been exposed to *Mycobacterium tuberculosis*. In some embodiments, the PIF peptide is administered in a pharmaceutical composition, wherein the pharmaceutical composition may comprise a therapeutically effective amount of a PIF peptide and a pharmaceutically acceptable excipient. In some embodiments, the PIF peptide is administered from a route selected from parenteral, transdermal, rectal, nasal, local intravenous administration, or oral administration. Such pharmaceutical compositions are prepared in a manner well known in the art and comprise at least one active PIF peptide associated with a pharmaceutically carrier. In some embodiments, the PIF peptide is administered once a day, twice a day, three times a day or four times a day. In some embodiments, the PIF peptide is administered for one week, two weeks, three weeks, four weeks, two months, three months, four months, six months, seven months, eight months, nine months, ten months, eleven months, twelve months, eighteen months, two years, three years, four years or five years. In some embodiments, the method may further comprise administering PIF in combination with other anti-TB agents. Furthermore, PIF may prevent intracellular damage caused by tuberculosis. Whereas most conventional therapies act outside the cell rendering them ineffective to address intracellular damage, PIF acts within the cell and thereby may prevent immune cells from being taken hostage by invading intracellular bacteria, such as *Mycobacterium tuberculosis*.

Glucocorticoids suppress the immune system, thus reducing inflammation and attendant pain and swelling at the site of the injury. A multi-protein complex composed of the unliganded glucocorticoid receptor ("GR"), Hsp90, and the tyrosine kinases LCK and FYN is recruited to the antigen activated T cell receptor (TCR) in T cells. This GR complex is necessary for TCR signaling. PIF in activated PBMC upregulates LCK, Fyn, and by reducing BAG3 expression HSP70, and 32 are activated. On binding of glucocorticoids to GR, this multi-protein complex dissociates blocking TCR signaling, thus suppressing the immune system. By binding to the T-cell receptor (TCR), PIF replaces cortisone and prevents immune suppression. Furthermore, by binding to the cortisone site, PIF reduces cortisone's side effects. Long-term cortisone exposure potentially has a number of severe side-effects including, but not limited to, hyperglycemia, insulin resistance, diabetes mellitus, osteoporosis, anxiety, depression, gastritis, colitis, hypertension, ictus, erectile dysfunction, hypogonadism, hypothyroidism, amenorrhoea, and retinopathy, among other problems. Accordingly, PIF affects Mtb-infected phagocytes, in particular the secretion of cytokines and chemokines, and prevents Mtb induced-immune suppression. Additionally, PIF binds to intracellular potassium channel KV 1.3 beta (a sub-unit of a protein (Kv1.3)) which modulates major immune cell functions, controls potassium pore flux, and also binds to intracellular insulin degrading enzyme which may increase cytokine secretion in CD3/CD28-stimulated T-cells. Without wishing to be bound by theory, PIF may act as a treatment for TB in a similar way to clofazimine (anti-TB drug), which acts by binding the Kv1.3 channel. PIF also blocks NFAT1 and the calcineurin pathways. Thus sPIF action may involve a direct antimacrobial effect acting within the infected macrophages. Thus, aspects of the invention are directed to the use of PIF for the treatment of tuberculosis.

Due to its specific immune profile, PIF may be able to precisely enhance the immune response against Mtb within the granuloma, counteracting local immune suppression by acting synergistically to augment an anti-TB drug's effectiveness, reducing drug resistance, and the likelihood development of latent TB. Nowadays, to be effective, anti-TB therapy may need to be used for several months and in cases of resistant TB multiple drugs may be required. However, PIF may effectively activate the immune system against tuberculosis and latent tuberculosis (TB and LTB). Therefore, PIF may help in shortening the length of therapy and may even reduce the need for multiple drug use. Additionally, PIF may also address the other pathological aspects that generally occur (ex. organ damage) in connection with TB. Thus, in some embodiments, PIF may be administered in conjunction with other anti-TB agents. Such anti-TB agents may be selected from isoniazid, rifampin, ethambutol, pyrazinamide and combinations thereof.

In some embodiments, PIF may be potentially used at all stages of intracellular damage: (1) early stages post-exposure where the immune system may be aided by PIF enabling immunity restoration; (2) later phase (if the attack was not timely caught) in which the disease or infection, such as, without limitation, TB, would have progressed and where PIF is expected to minimize the side-effects, allowing restoration of the immune system; and (3) latent infection, for example, in TB, where PIF may lower tuberculin-induced disease burden while maintaining body's fighting efficacy.

As used herein, the terms "peptide," "polypeptide" and "protein" are used interchangeably and refer to two or more amino acids covalently linked by an amide bond or non-amide equivalent. The peptides of the invention can be of any length. For example, the peptides can have from about two to about 100 or more residues, such as, 5 to 12, 12 to 15, to 18, 18 to 25, 25 to 50, 50 to 75, 75 to 100, or more in length. Preferably, peptides are from about 2 to about 18 residues. The peptides of the invention include 1- and d-isomers, and combinations of l- and d-isomers. The peptides can include modifications typically associated with post-translational processing of proteins, for example, cyclization (e.g., disulfide or amide bond), phosphorylation, glycosylation, carboxylation, ubiquitination, myristylation, or lipidation.

Peptides disclosed herein further include compounds having amino acid structural and functional analogues, for example, peptidomimetics having synthetic or non-natural amino acids or amino acid analogues, so long as the mimetic has one or more functions or activities of compounds of the invention. The compounds of the invention therefore include "mimetic" and "peptidomimetic" forms.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

In some aspects, the invention is directed to a pharmaceutical composition comprising a PIF peptide, as defined above, and a pharmaceutically acceptable carrier or diluent, or an effective amount of a pharmaceutical composition comprising a compound as defined above.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the therapeutic of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

In one embodiment, the PIF peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7 membered alkyl, amide, amide lower alkyl, amide di (lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24, 243-252, 1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to PIF receptors, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, Curr. Op. Chem. Biol. 2, 441-452, 1998; Hruby et al., Curr. Op. Chem. Biol. 1, 114-119, 1997; Hruby & Balse, Curr. Med. Chem. 9, 945-970, 2000). One class of peptidomimetics a backbone that is partially or completely non-peptide, but mimics the peptide backbone atom-for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

Embodiments and methods of the present invention may use any of the following PIF peptides: Met-Val-Arg-Ile-Lys-Pro-Gly-Ser-Ala (SEQ ID NO: 1); Met-Val-Arg-Ile-Lys-Pro-Gly-Ser-Ala-Asn-Lys-Pro-Ser (SEQ ID NO: 2); Met-Val-Arg-Ile-Lys-Pro-GlySer-Ala-Asn-Lys-Pro-Ser-Asp-Asp (SEQ ID NO: 3); Met-Val-Arg-Ile-Lys-Tyr-Gly-Ser-Tyr-Asn-Lys-Pro-Ser-Asp (SEQ ID NO: 4); Ser-Gly-Ile-Val-Ile-Tyr-Gln-Tyr-Met-Asp-Asp-Arg-Tyr-Val-Gly-Ser-Asp-Leu (SEQ ID NO: 5); Val-Ile-Ile-Ile-Ala-Gln-Tyr-Met-Asp (SEQ ID NO: 6); Ser-Gln-Ala-Val-Gln-Glu-His-Ala-Ser-Thr (SEQ ID NO: 7); Ser-Gln-Ala-Val-Gln-Glu-His-Ala-Ser-Thr-Asn-Xaa-Gly, where Xaa can be any amino acid (SEQ ID NO: 8).

A list of PIF peptides, both the isolated, natural and synthetic, are provided below in Table 1. Antibodies to various PIF peptides and scrambled PIF peptides are also provided.

TABLE 1

PIF Peptides

| (SEQ ID NO) | Peptide | Amino Acid Sequence (isolated, natural or synthetic) |
|---|---|---|
| SEQ ID NO: 1 isolated native, matches region of Circumsporozoite protein (Malaria) | PIF-1$_{(9)}$ | MVRIKPGSA |
| SEQ ID NO: 2 isolated native, matches region of Circumsporozoite protein (Malaria) | PIF-1$_{(13)}$ | MVRIKPGSANKPS |
| SEQ ID NO: 3 isolated native, matches region of Circumsporozoite protein (Malaria) | PIF-1$_{(15)}$ | MVRIKPGSANKPSDD |
| SEQ ID NO: 4 isolated native, matches region of Circumsporozoite protein (Malaria) | PIF-1$_{(14)}$ | MVRIKYGSYNKPSD |
| SEQ ID NO: 5 isolated native, matches region of Rev Trans | PIF-3$_{(18)}$ | SGIVIYQYMDDRYVGSDL |
| SEQ ID NO: 6 | PIF-4$_{(9)}$ | VIIIAQYMD |
| SEQ ID NO: 7 iolated native, matches region of human retinoid and thyroid hormone receptor-SMRT | PIF-2$_{(10)}$ | SQAVQEHAST |
| SEQ ID NO: 8 isolated native, matches region of human retinoid and thyroid hormone receptor-SMRT | PIF-2$_{(13)}$ | SQAVQEHASTNXG |

() = number of AA

This invention and embodiments illustrating the method and materials used may be further understood by reference to the following non-limiting examples.

EXAMPLE 1

Peptide Synthesis: Synthetic PIF-1$_{15}$ (MVRIKPG-SANKPSDD) was obtained by solid-phase peptide synthesis (Peptide Synthesizer, Applied Biosystems) employing Fmoc (9-fluorenylmethoxycarbonyl) chemistry. Final purification is carried out by reverse-phase HPLC and identity is verified by MALDI-TOF mass spectrometry and amino acid analysis and purified to >95%, by HPLC, and documented by mass spectrometry (Biosynthesis, Texas).

EXAMPLE 2

As shown in FIG. 4, cultured bone marrow derived phagocytes were exposed to PIF (SEQ ID NO. 4; peptide MVRIKPGSANKPSDD), interferon-gamma (phagocyte-activating cytokine) and Mtb and measured the cytokine response in the presence or absence of Kv1.3, a potassium channel inhibitor. MCP-1 (a chemokine) interleukin (IL)-6 and IL-5 were increased by Mtb; this induction was augmented by PIF and blocked by Kv1.3 inhibition. MIG and IP10 chemokines were modestly augmented by PIF when IFN activated phagocytes were exposed to Mtb; inhibition of Kv1.3 reduced the PIF effect. PIF augmented VEGF and FGFβ induction by Mtb (regardless of phagocyte activation by IFNγ) and inhibition of Kv1.3 augmented this response. Inflammatory cytokines TNF, IL-1α, IL-1β, MIP1α and KC were induced by Mtb, augmented by PIF and further augmented by anti Kv1.3. In conclusion, PIF-conditioned macrophages exhibit an altered response to Mtb. PIF was able to modulate the phagocyte response to Mtb and may therefore modulate disease development

EXAMPLE 3 sPIF effectively controls Mtb-infected macrophages: In vitro studies used mouse bone marrow derived dendritic cells (BMDCs) exposed to Mtb+/−PIF for 24 hrs in culture. sPIF clearly modulated the phagocyte response to Mtb at low (nM) physiological PIF concentrations. Pre-treatment with sPIF resulted in BMDCs augmented response to Mtb specifically: inflammatory cytokines TNF, IL-1a, IL-1b and IL-6 and chemokines MCP-1 MIP1a and KC were increased. Importantly, sPIF acted to increase the response of BMDC even in absence of pre-activation by interferon-γ. VEGF and FGFb (growth factors) were also augmented by sPIF suggesting its capability to modulate the remodeling activity of BMDCs. Hence, PIF exerts a potent anti-mycobacterial response that is evidenced both in absence and presence of acquired immunity as represented by interferon-γ pre-treatment.

Whether binding to Kv1.3b is also relevant in the BMDC context was demonstrated by using an anti-Kv1.3 inhibitor. A number of sPIF induced cytokine and chemokine secretion patterns were modified in the presence of the inhibitor. Collectively the in vitro and in vivo data (BMDC Mtb data) support the sPIF's efficacy to control Mtb infection.

EXAMPLE 4

Figure 5A:
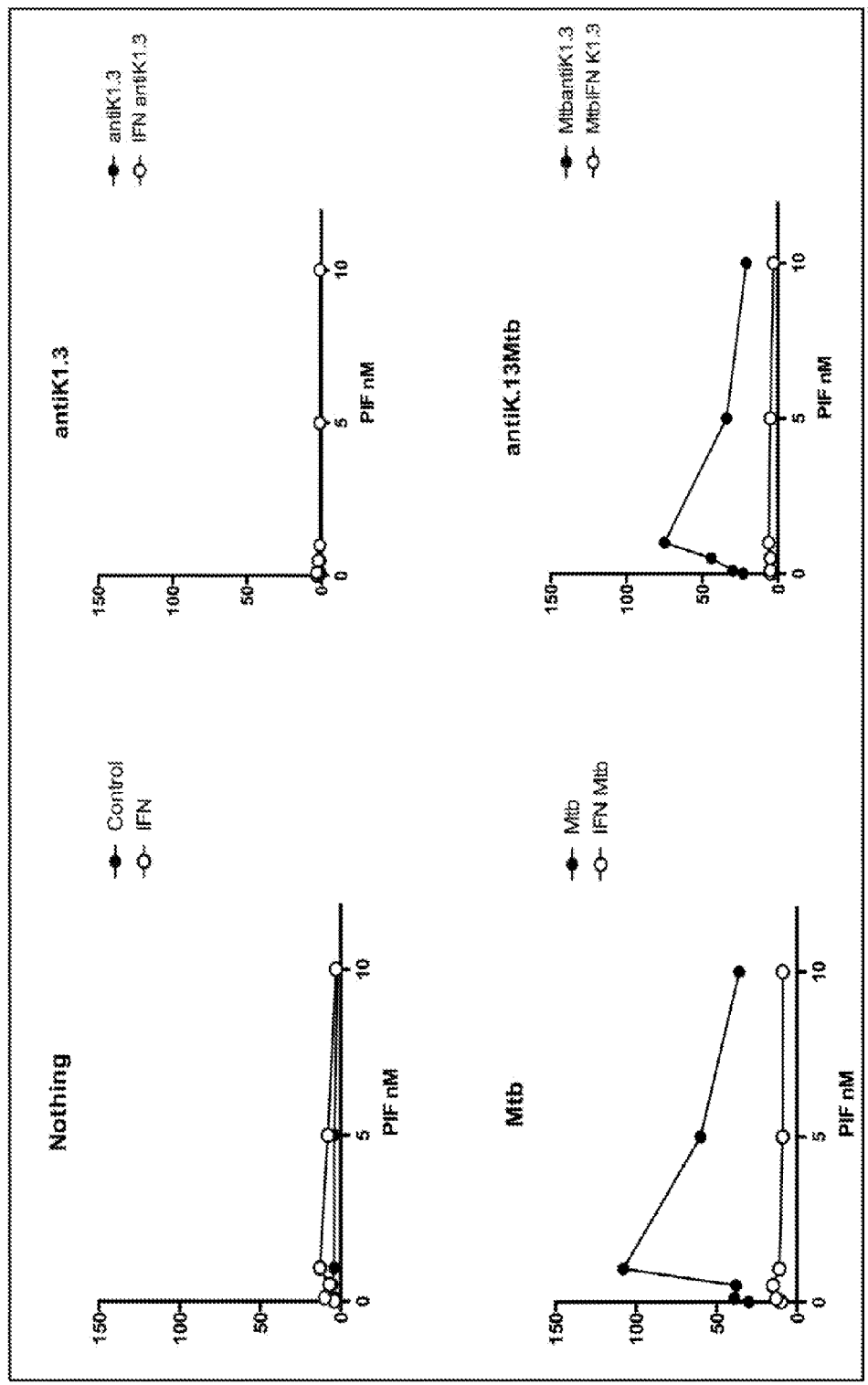
FIG. 5A illustrates that MCP-1 (a chemokine) was induced by Mtb, which was augmented by PIF and a Kv1.3 inhibitor. Administration of IFNγ stopped the response. Low sPIF doses increased MCP-1 (Monocyte chemotactic protein-1) secretion by isolated macrophages. The Kv1.3 inhibitor at 100 nM blocked sPIF effect.
Figure 5B:
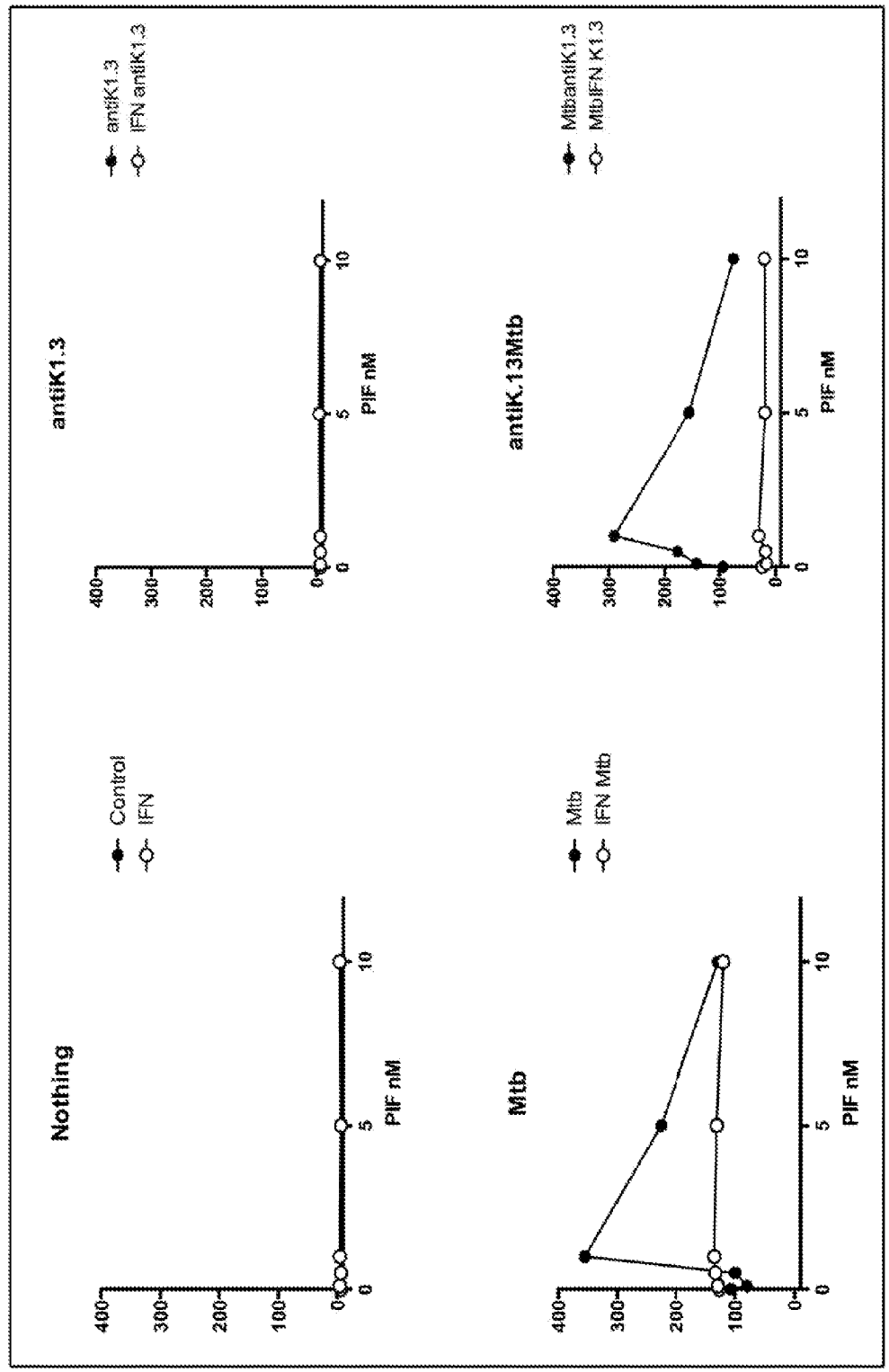
FIG. 5B illustrates IL-6 was induced by Mtb and this induction was augmented by PIF and reduced by anti-Kv1.3. Administration of IFN stopped the response.
Figure 5C:
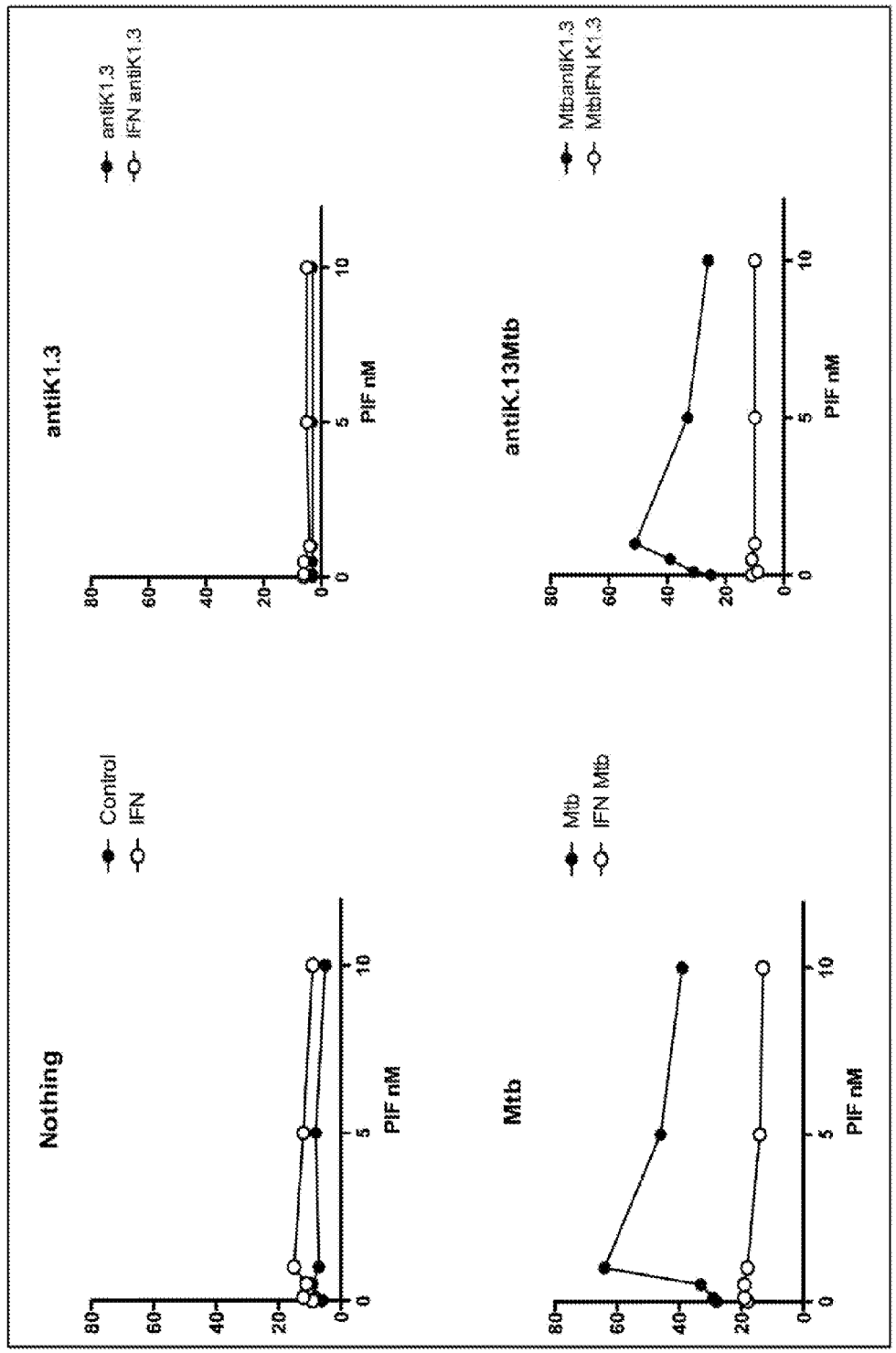
FIG. 5C illustrates IL-5 was induced by Mtb and this induction was augmented by PIF and reduced by anti-Kv1.3. Administration of IFN stopped the response.

As shown in FIGS. 4 and 5, the objective of this study was to assess the ability of PIF to (1) modulate Mtb infected cultured phagocytes; and (2) control chronic acquired Mtb infection in a murine model. Results indicated that PIF modulates cytokine/chemokine secretion. MCP1, IL6, and IL5, were increased by Mtb, further induced by PIF, and blocked by Kv1.3 inhibitor. MIG, and IP10 were modestly augmented by PIF when IFNγ was added to Mtb, Kv1.3 inhibitor blocked effect. PIF promoted VEGF, and FGFβ induction by Mtb (regardless of IFNγ activation); and the Kv1.3 inhibitor augmented this effect. TNFa, IL-1a, IL-1b, MIP1a, and KC were induced by Mtb, is augmented by PIF, and further augmented by Kv1.3 inhibitor. Mice were infected via aerosol with 75 cfu Mtb at day 0. Infected mice were then treated with 0.1 mg/kg PIF daily injection at day 60-70, followed by 10 day observation. Viable Mtb bacteria count of lung tissue was assessed on day 80, 10 days post-therapy. In vivo, short-term, low-dose PIF treatment reduced Mtb infection. This effect persisted 10 day post-therapy (see FIG. 5).

In conclusion, PIF treated phagocytes exhibited an altered response to Mtb. PIF modulated Mtb infected phagocytes cytokine/chemokine secretion in a response which was partially Kv1.3 dependent. PIF had a therapeutic effect on chronically Mtb-infected mice. PIF Rx was low-dose, short-term and achieved long-term effects persisting after the end of PIF administration (0.1 mg, 10 day, 10-80 day post-therapy).

EXAMPLE 5

Two inhibitors were tested for an effect on PIF modulation of cytokine production by stimulated human T lymphocytes. Peripheral blood was obtained from two healthy donors. Mononuclear cells were purified by Ficol-Hypaque centrifugation. Cultures were prepared in duplicate wells at $8 \times 10^4$ cells per well having either (1) Media with 0, 1, 10 and 50 nM PIF; (2) anti-CD3/CD28 stimulation without and with Kv1.3 inhibitor at 100 nM, IDE inhibitor at 5 µM, or both together or (3) anti-CD3/CD28 stimulation without and with Kv1.3 inhibitor at 100 nM, IDE inhibitor at 5 µM, or both together with 1, 10 or 50 nM PIF. The culture supernatants were collected 24 hours post-treatment and were assayed for eleven Th1/Th2 cytokines using a multiplex system (Bender, Cat. No. BMS810FF): IL-1beta, IL-2, IL-4, IL-5, IL-6, IL-8, IL-10, IL-12p70, TNF-alpha, TNF-beta, IFN-gamma.

As shown in FIG. 3, results indicated that PIF alone tested at 1, 10 and 50 nM had no effect on the multiple analytes tested. CD3/CD28 did not activate the production of IL-12, IL-4, IL-5, IL-1b and TNFβ. Without CD3/CD28 induction, the level of IL-8 is very high (over the Upper limit of Quantification −8.91 ng/mL)). It appears that CD3/CD28 down-regulates the IL-8 production. A significant effect of PIF or Kv1.3 inhibitor, or IDE inhibitor, was not clear. CD3/CD28 T-cell stimulation induced secretion of IFNg, IL-2, Il-6 and TNFα. A slightly higher induction with the donor 2 cells was observed. In the presence of PIF at 1, 10 and 50 nM, the analytes' level was reduced in the presence of 5 µM IDE inhibitor, but not in the presence of 100 nM Kv1.3 inhibitor. There was a decrease in the presence of both inhibitors.

In conclusion, PIF was shown to bind intracellular insulin degrading enzyme (IDE) in a cell based assay using specific IDE inhibitor.

EXAMPLE 6

PIF antipathogenic effect is further documented on PBMC mRNA modulating TOLL receptors among many other genes. The embryo/allograft is a perfect transplant, tolerated by mother/host, while preserving her defense mechanisms to fight disease. Preimplantation factor (PIF) is necessary for viable pregnancy, orchestrating implantation, possibly modulating maternal immunity favoring acceptance.

As shown in FIG. 1, sPIF (PIF analog) was tested on naïve and TCR-co-activated human PBMCs assessing proliferation, cytokine secretion and mRNA expression. FITC-sPIF binding to PBMCs subsets was determined using flow cytometry. sPIF's effect on Ca++ mobilization was tested by Flex station. PIF was detected within pregnant mouse uterus using anti-PIF-monoclonal antibody. sPIF was found to modulate PBMCs: blocked anti-CD3-Mab-stimulated proliferation and mixed lymphocyte reaction. In naïve-PBMCs, sPIF reduces TH1 (TNF-α, IL2) cytokines while in activated PBMCs. sPIF promotes TH2 (IL-10, IL4, IL5, IL3), and TH1 (IL2, IFNγ) cytokines. Co-stimulation led to TH2/TH1 cytokine bias and global gene analysis demonstrated an increased pro-tolerant and reduced pro-inflammatory profile. FITC-sPIF binds all CD14+, and activated T cells, key regulatory FOXP3+ Tregs (Treg) and B cells. PIF does not act through Ca++ mobilization, a common pathway for immune suppressive agents. PIF is preferentially taken up by uterine NK cells in pregnant murine uterus.

In conclusion, the post-fertilization embryo, through its comprehensive 1 PIF-based signaling, modulates peripheral immunity to create tolerance without immune suppression. Under challenged conditions, PIF promotes maternal ability to fight disease. Through control of NK cells, PIF may reduce maternal rejection towards the embryo within the uterus. Overall, PIF plays a fundamental role in the implantation process, orchestrating maternal recognition of pregnancy, and controlling both peripheral and local immune environments. PIF binds CD14+ cells and at elevated concentrations to T and B 580 cells. Unstimulated PBMC were cultured for 24 hours, and the binding of FITC-PIF 581 (0.3-25 µg/ml) to specific PBMC sub-populations was determined using surface markers 582 by flow cytometry with two-color stain or microscopy. FIG. 1 shows FITC-PIF presence inside the cell.

EXAMPLE 7

As shown in FIG. 2, cells (200,000/well) were stimulated with plate-bound anti-CD3 antibody or anti-CD3/anti-CD28 MAb 10 µg/ml or by heterologous mixed lymphocyte reaction (MLR), cultured 2-4 days in serum-free medium (GIBCO™ AIM-V Medium, Invitrogen Corp., Carlsbad, Calif.) containing 0-500 nM sPIF or PIFscr. In some experiments, IL2r recombinant (30 U/ml)+/−sPIF was added. Proliferation was determined by [3H]-thymidine incorporation. In other experiments, sPIF0-1000 nM tested on isolated T-cells (CD3+) on both MLR and anti-CD3/anti-CD28 MAb10 µg/ml stimulated-PBMCs.

EXAMPLE 8

Invitrogen's Protein-Protein Interaction Profiling Service was performed on ProtoArray® Human Protein Microarrays v5.0 (protein microarray) and the interaction with more than 9,000 human proteins was investigated. One Alexa Fluor® (fluorescent dye) 647-conjugated synthetic peptide, provided by the CARL Reproductive Institute, designated as PIF-Alexa 647, was used to probe the microarrays at two concentrations (250 nM and 2.5 µM) in duplicate. The results from these assays were compared to a negative control assay in which the probe protein was excluded. All interactions of the probe protein with the immobilized proteins on the microarrays were evaluated by specified statistical threshold criteria within the array and compared to interactions observed on the negative control array. Visual confirmation of the positive hits was also performed by directly inspecting the array images to verify the authenticity and quality of the signals. From these analyses, a total of eleven (11) human proteins were identified as candidate interactors for PIF-Alexa 647 (fluorescent dye).

EXAMPLE 9

To demonstrate the therapeutic potential of PIF, male ApoE−/− mice were fed a high fat Western diet containing 22% fat and 0.15% cholesterol for 7 weeks. Mice were then randomly assigned to one of six clusters; 3 intervention groups of varied PIF doses, and 3 control groups of scrPIF or PBS. Treatments were administered via 150 µL i.p. injection every 3rd day, for a total of 7 weeks.

Figure 7A:
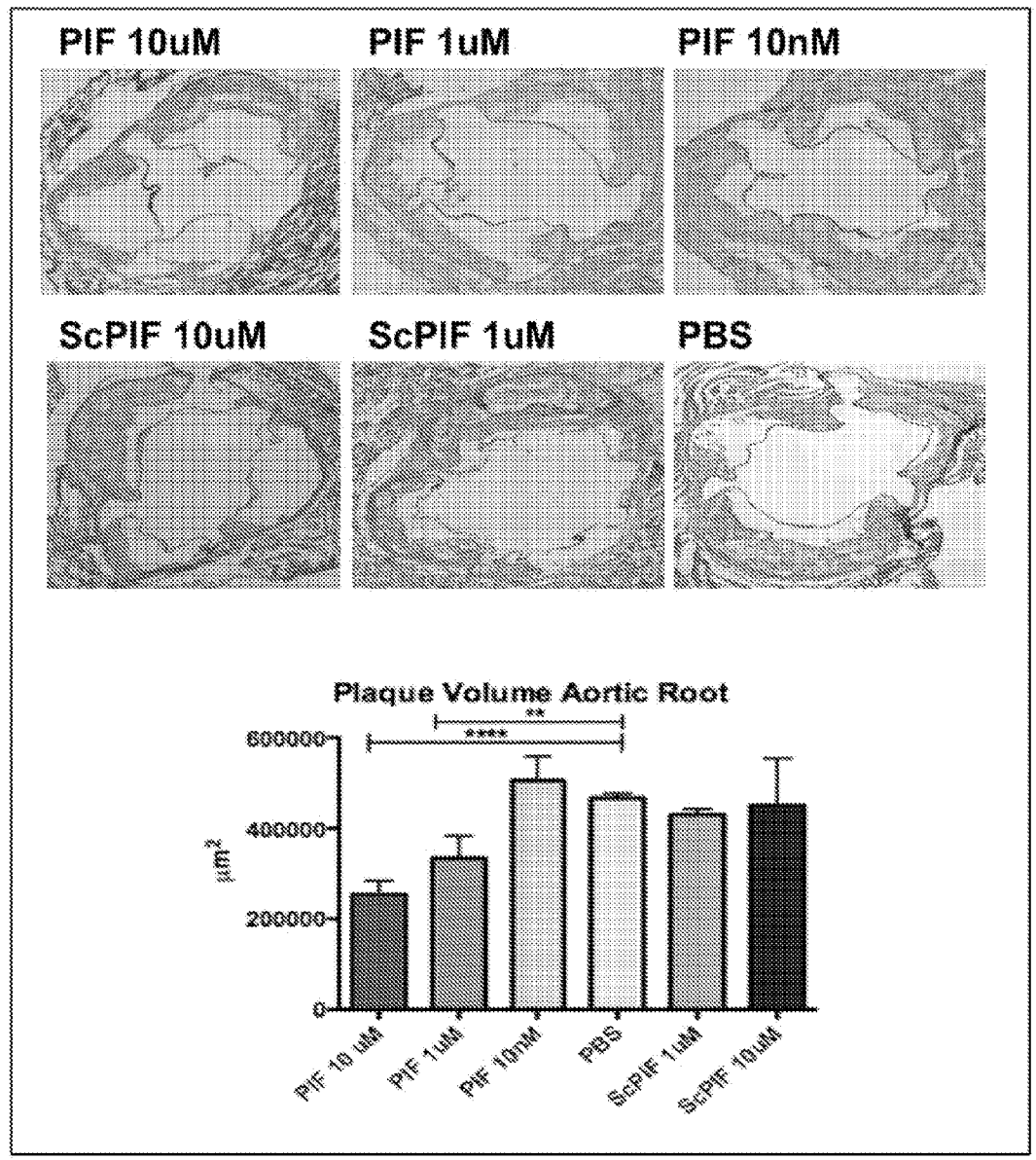
FIG. 7 illustrates that PIF reduces atherosclerotic plaque area in the (FIG. 7A) aortic root and (FIG. 7B) the aortic arch. Aortic root and arch sections were stained with HE. The mean atherosclerotic area (μm2)±SEM was quantified. PIF 0.1 mg/kg/day treatment significantly reduced the plaque area in the aortic root by 30% compared to the PBS control (p=0.0008). A greater reduction of 46% was evident in PIF 1 mg/kg/day compared to PBS (p<0.0001). The higher dose of PIF also statistically significantly reduced plaque area compared to both doses of scrPIF (p<0.0001). PIF 1 mg/kg/day treatment significantly reduced the plaque area of the aortic arch by 43% compared to the PBS control (p<0.002). A reduction was again also evident between PIF 1 mg/kg/day and both doses of scrPIF (*p=0.0005, **p<0.0001 respectively).
Figure 7B:
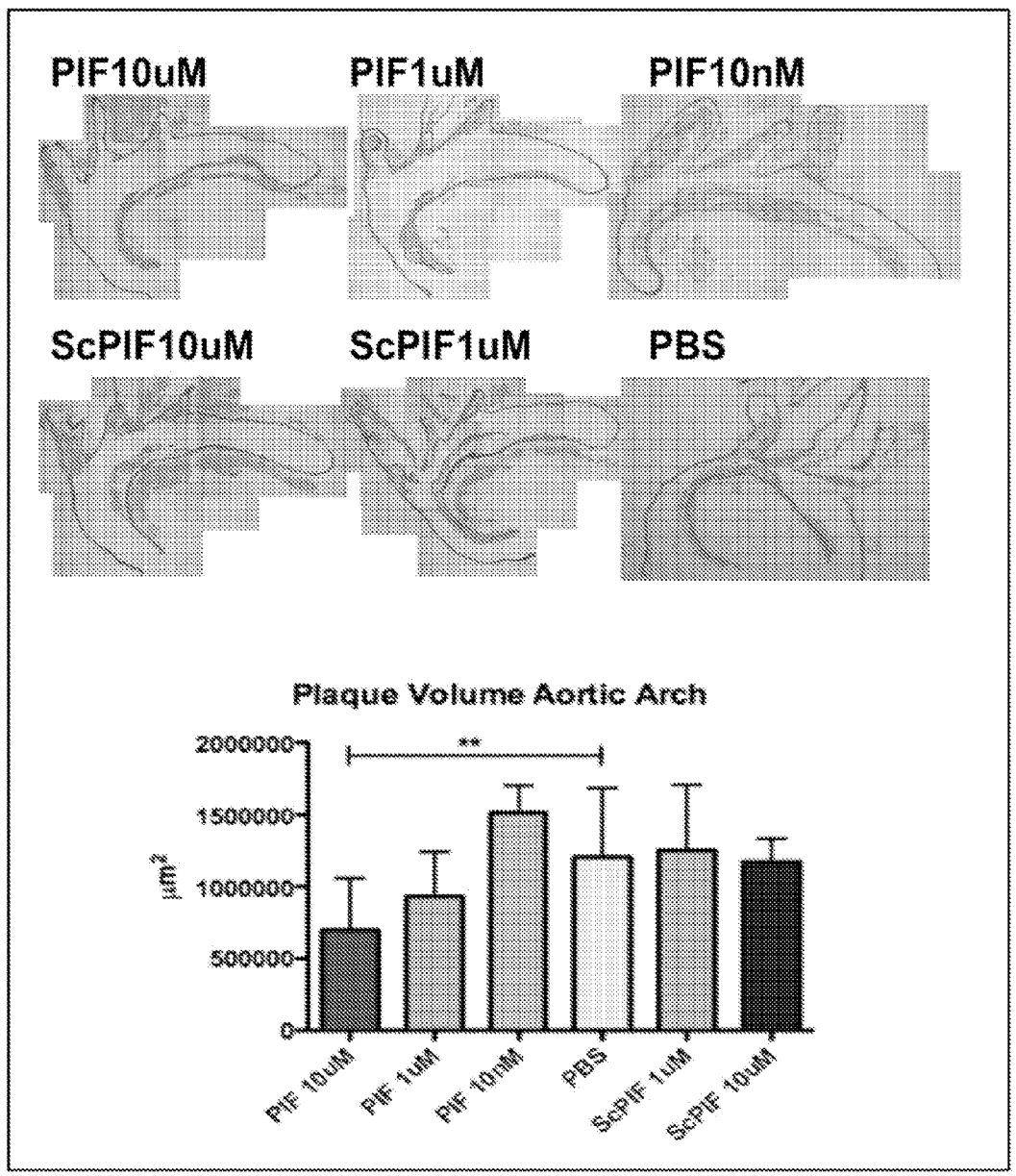
Figure 8:
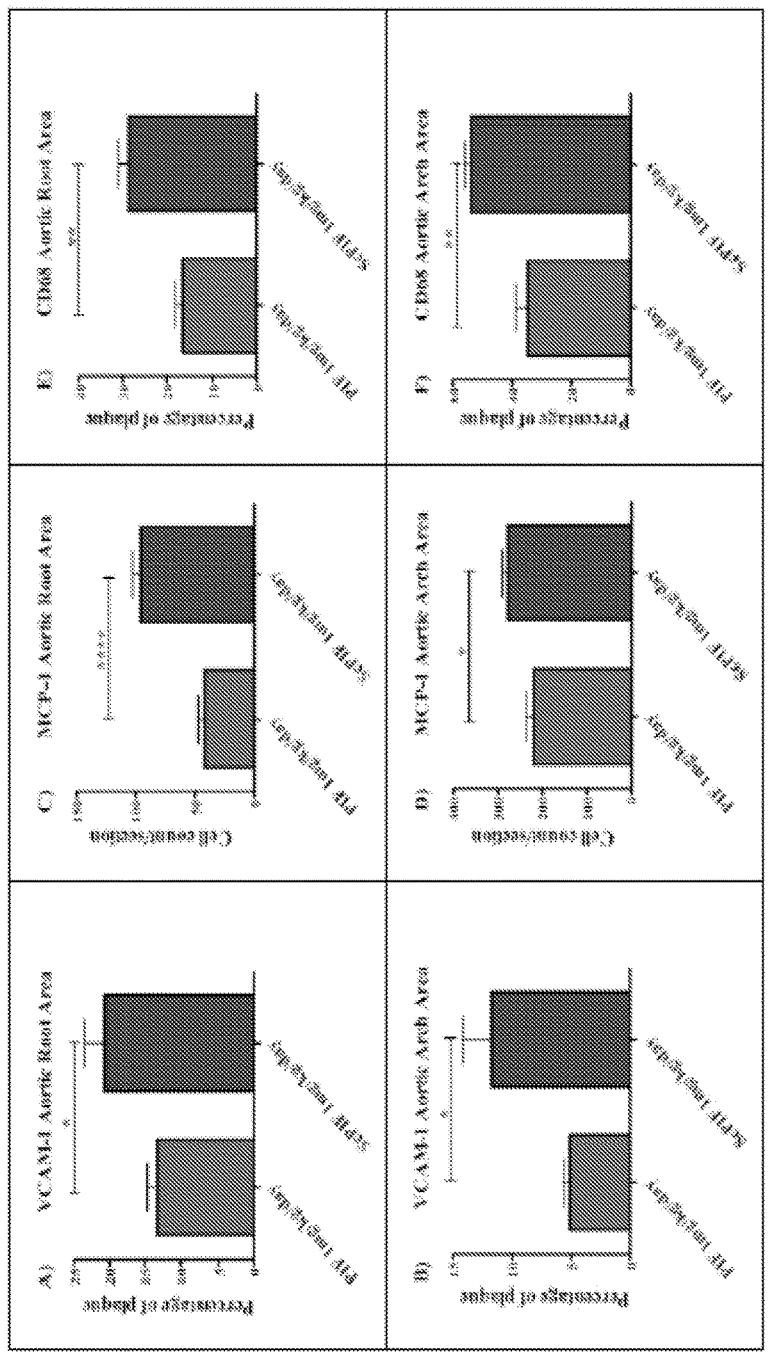
FIG. 8A, FIG. 8B, FIG. 8C, FIG. 8D, FIG. 8E, and FIG. 8F illustrate that PIF reduces VCAM-1, MCP-1 and CD68 in the aortic root and arch of ApoE−/− mice fed with high fat diet (n=8 each, mean and SEM, *p<0.05, p<0.01, *p<0.001, ****p<0.0001).
Figure 9:
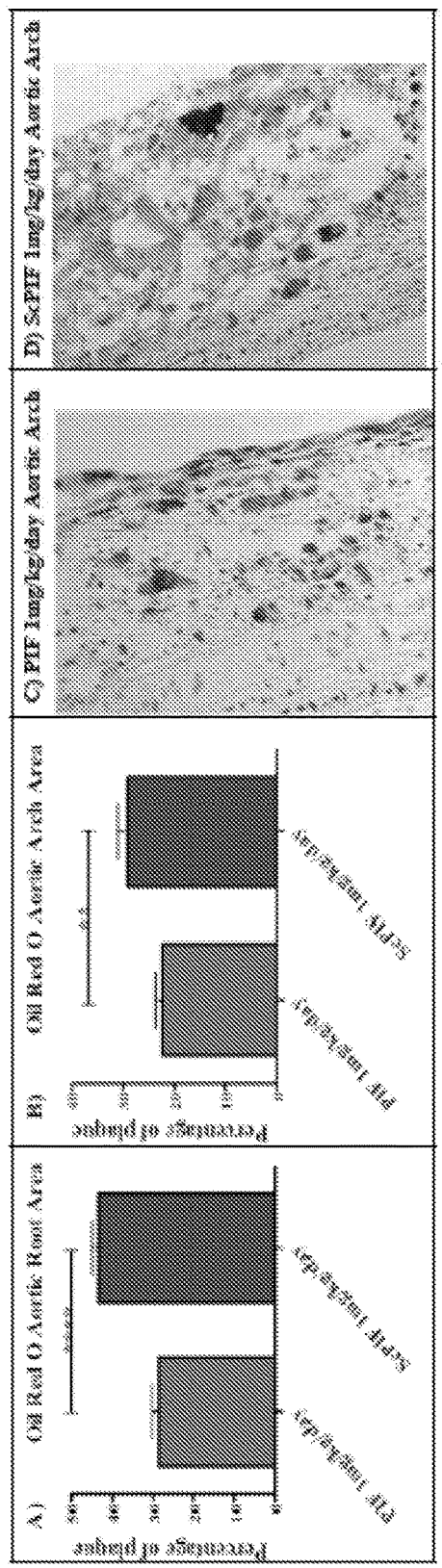
FIG. 9A, FIG. 9B, FIG. 9C, and FIG. 9D illustrate that PIF but not scrPIF reduces Oil Red 0 (ORO) staining in the aortic arch and root. ORO histology was employed to identify lipids in the mouse atherosclerotic plaque. Lipids were quantified by red signal intensity percentage area of plaque±SEM.
Figure 10A:
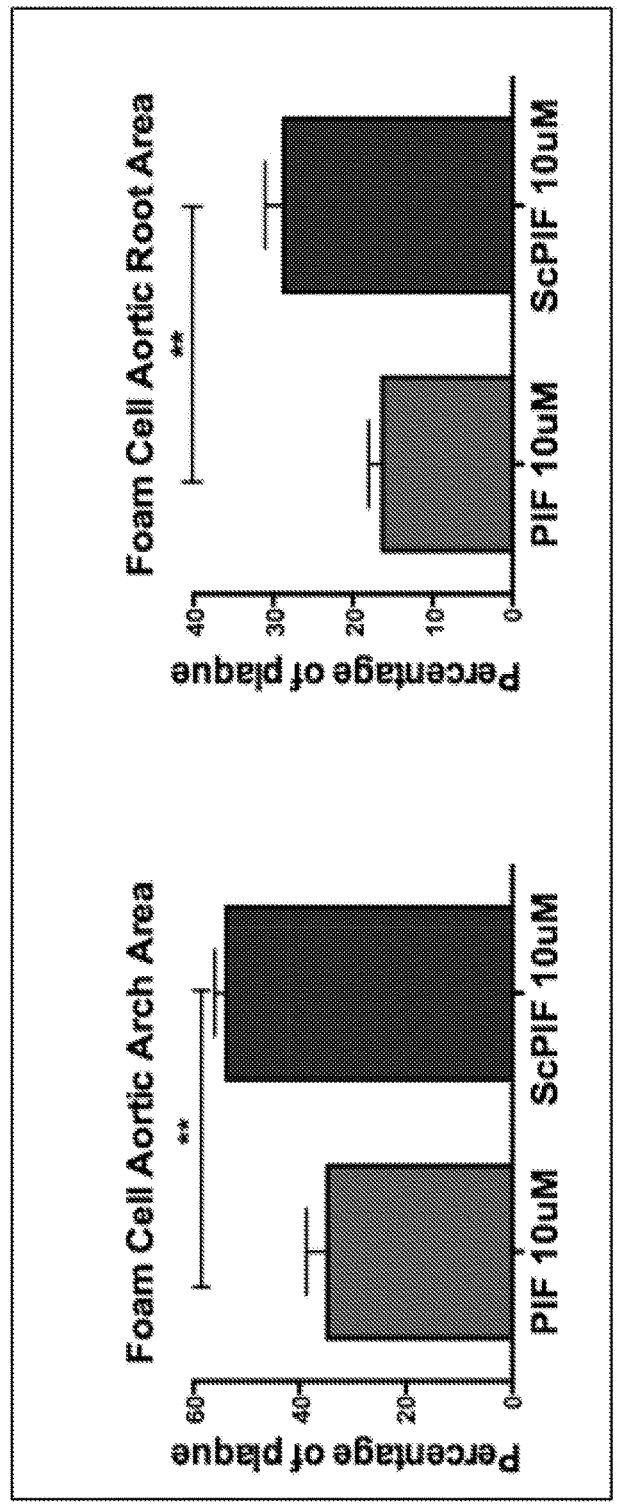
(FIG. 10A) CD68 in the aortic root (p=0.0017) and the aortic arch (p=0.0035), and (FIG. 10B) lipids in the aortic root (**p=<0.0001) and the aortic arch (p=0.0093).
Figure 10B:
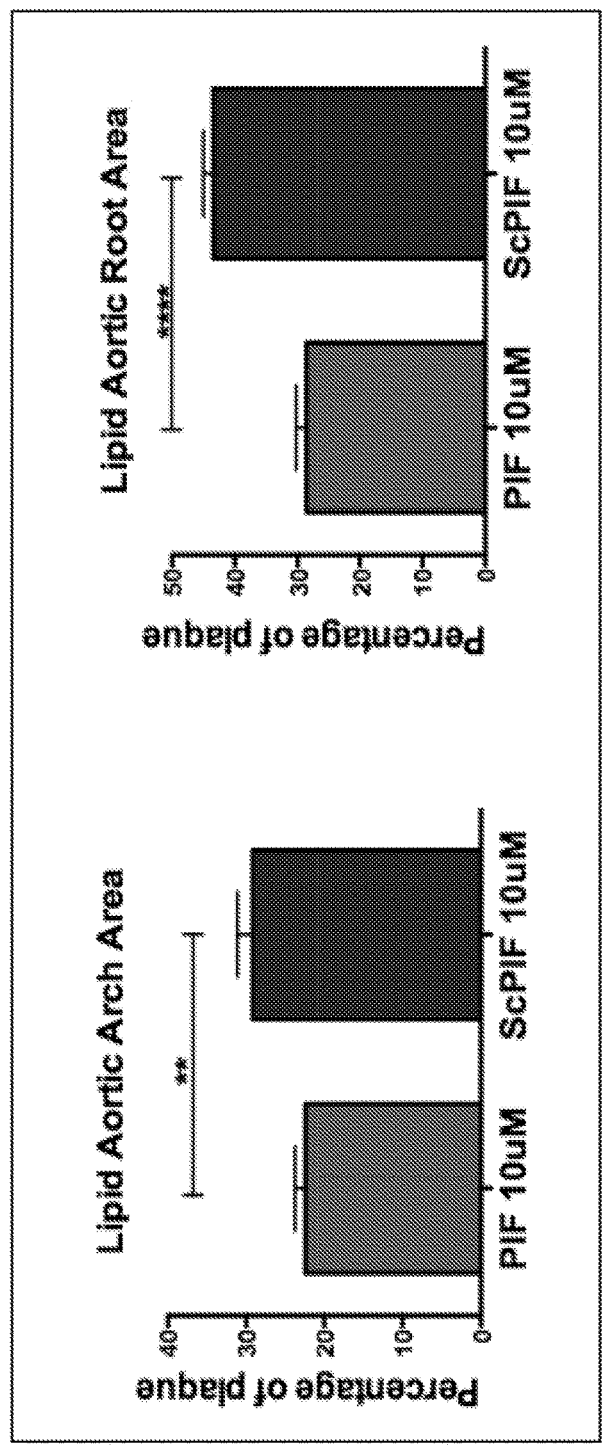
FIG. 10 illustrates that PIF reduces.

As shown in FIG. 7, PIF 0.1 mg/kg/day treatment significantly reduced the plaque area in the aortic root by 30% compared to the PBS control (D, p=0.0008). A greater reduction of 46% was evident in PIF 1 mg/kg/day compared to PBS (D, p<0.0001). The higher dose of PIF also statistically significantly reduced plaque area compared to both doses of scrPIF (p<0.0001). PIF 1 mg/kg/day treatment significantly down-regulated the plaque area of the aortic arch by 43% compared to the PBS control (E, p<0.002). A reduction was again also evident between PIF 1 mg/kg/day and both doses of scrPIF (*p=0.0005, p<0.0001 respectively). Furthermore, as shown in FIGS. 8-10**, PIF also reduced VCAM-1, MCP-1, CD68 and lipids in the aortic root and arch.

Figure 11:
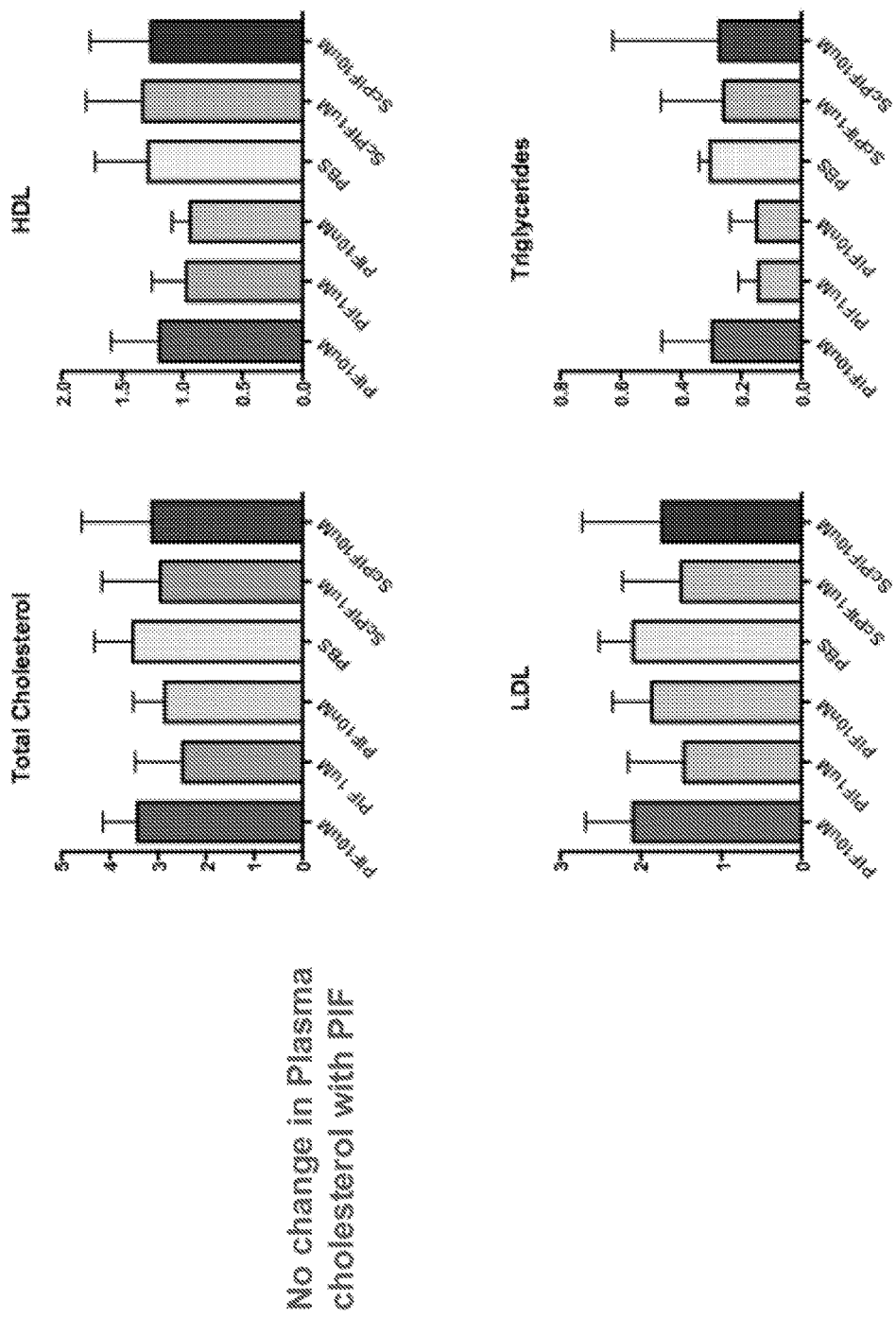
FIG. 11 illustrates that PIF does not affect circulating lipids, and no change in plasma cholesterol is noted. A COBAS analyzer was used to determine the cholesterol levels by using mouse plasma from the various treatment groups. All animals still had very high cholesterol levels, and to obtain a reading the plasma needed to be diluted to 1:10. No statistical difference was seen between any group using one way ANOVA paired with Tukey's Multiple Comparison Test. This confirmed that the reduction in lipids and foam cells were due to PIF's actions on the atherosclerotic lesion and not on the fat levels as a whole.

In conclusion, PIF reduces atherosclerosis formation in a mouse model that is prone to the disease and is fed a high fat diet. The protection was direct and led to reduced atherosclerotic plaques on both the aortic arch and root-target sites. A decrease in fat accumulation was evident, as well as a decrease in inflammatory macrophages and a lower number of fat foam cells. The protective effect was not related to changes in circulating lipids, as their levels did not change following PIF administration (see FIG. 11). The effect was specific since it was not replicated by PIFscr and PBS. PIF offers a new safe and targeted treatment for protection against atherosclerosis, which is a major health disorder mainly in the developed world.

EXAMPLE 10

To demonstrate that PIF inhibits MCP-1 induced monocyte migration, a mouse peritonitis model study was conducted. In this model, 8-12 weeks old C57bl6 mice were injected with either PIF, scPIF (0.3 nmol/g i.p.) or PBS as a vehicle control. Peritonitis was induced by injecting 3 ml 4% thioglycolate i.p. and after 20 hours, the mice were anaesthetized and the peritoneal cavity was flushed with 5 ml sterile PBS. Subsequently, monocytes and macrophages were quantified with F4/80 and CD11b in flow cytometry.

Figure 6:
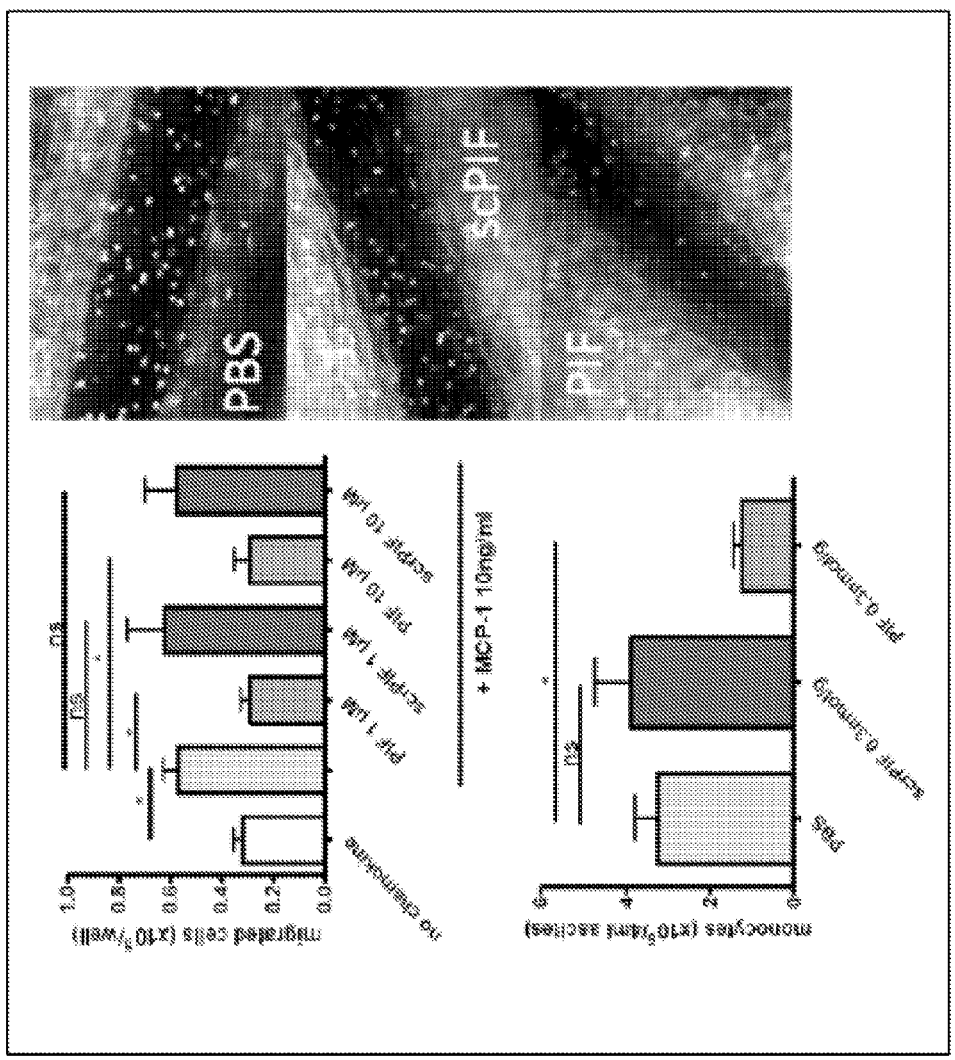
FIG. 6 illustrates that PIF inhibits MCP-1 induced monocyte migration in a mouse peritonitis model. 8-12 weeks old C57bl6 mice were injected with PIF or scPIF (0.3 nmol/g i.p.) or PBS as vehicle control. Peritonitis was induced by injecting 3 ml 4% thioglycolate i.p. and after 20 hours, the mice were anaesthetized and the peritoneal cavity was flushed with 5 ml sterile PBS. Subsequently, monocytes/macrophages were quantified with F4/80 and CD11b in flow cytometry. PIF (1 μM & 10 μM) significantly reduced MCP-1 induced transmigration of THP-1 cells in an in vitro transwell migration assay (*p<0.01). PIF inhibits leukocyte adhesion and rolling in mesenteric venules in intravital microscopy using the peritonitis model and cell staining with rhodamine.

As shown in FIG. 6, the results showed that PIF (1 µM & 10 µM) significantly reduced MCP-1 induced transmigration of THP-1 cells in an in vitro transwell migration assay (*p<0.01). PIF further inhibited leukocyte adhesion and rolling in mesenteric venules in intravital microscopy using the peritonitis model as described in and cell staining with rhodamine.

EXAMPLE 11

Healthy pregnancy requires coordination of several soluble factors acting individually or in synergy with each other. Examples of those soluble factors include HLA-G, cytokines, and progesterone. The soluble factors are secreted during infection, which affects fetal development and often causes complications which may result in abortive pregnancy. PIF exerts an autocrine trophic protective effect on the embryo and promotes embryo implantation and trophoblast invasion. A determination was made as to whether PIF affects LPS-induced nitrous oxide (NO) secretion by macrophages and how PIF limits macrophage responses to LPS, which is the major endotoxin of gram negative bacteria.

A macrophage cell line was cultured with 200 nM PIF (synthetic PIF analog) for 2 and 5 days. In the last 24 hours of the experiment, LPS was added to the culture for cell activation. A Greiss reagent test was performed to detect NO secretion to the supernatant. Surface Plasmon Resonance spectroscopy (SPR) was used to evaluate LPS and LPS receptors binding (TLR4-MD2 and CD14) to the PIF-labeled sensor surface. Two chemotypes of LPS (From *E. coli* 055:B5 and *E. coli* EH100) at 3 concentrations (5, 25 and 100 µM) were tested.

The results showed that PIF 200 nM did not affect the baseline NO at either the 2 or the 5 day incubation. In contrast, PIF significantly down-regulated NO production following LPS activation. The effect at 2 days was more pronounced than at 5 days (P<0.05). Preliminary results indicated an apparent absence of binding of immobilized PIF to both LPS chemotypes tested; similarly, no binding was observed to the scrambled PIF used as the control (random peptide of same amino acid in random order). To ascertain PIF's structural integrity, a PIF-specific antibody was incubated with purified PIF and results showed that the antibody bound to PIF. Under the conditions set up for the SPR analysis, PIF exhibited no apparent LPS binding.

In conclusion, PIF was shown to block NO secretion, a major LPS-induced reactive nitrogen intermediate produced by iNOS, which is an enzyme absent in resting macrophages. PIF does not bind directly LPS, but its action might involve binding to LPS-associated receptors such as CD14, MD2 and macrophage scavenger receptor (SR). Such data supports a targeted anti-inflammatory effect of PIF on the innate immune system.

The invention claimed is:

1. A method of therapeutically treating *Mycobacterium tuberculosis* infection comprising administering to a subject in need thereof a therapeutically effective amount of a PIF peptide comprising an amino acid sequence of SEQ ID NO: 3.

2. The method of claim 1 further comprising administering a potassium channel inhibitor.

3. The method of claim 2, wherein the potassium channel inhibitor is a Kv1.3 inhibitor.

4. The method of claim 2, wherein the potassium channel inhibitor is IFNγ.

5. The method of claim 1, wherein the therapeutically effective amount is from about 0.01 to about 10 milligrams of PIF peptide per kilogram of subject.

6. A method of therapeutically treating tuberculosis comprising administering to a subject in need thereof a therapeutically effective amount of a PIF peptide comprising an amino acid sequence of SEQ ID NO: 3.

7. The method of claim 6 further comprising administering a potassium channel inhibitor.

8. The method of claim 7, wherein the potassium channel inhibitor is a Kv1.3 inhibitor.

9. The method of claim 7, wherein the potassium channel inhibitor is IFNγ.

10. A method of decreasing dissemination of tuberculosis bacteria comprising administering to a subject in need thereof a therapeutically effective amount of a PIF peptide comprising an amino acid sequence of SEQ ID NO: 3.

11. The method of claim 10 further comprising administering a potassium channel inhibitor.

12. The method of claim 11, wherein the potassium channel inhibitor is a Kv1.3 inhibitor.

13. The method of claim 11, wherein the potassium channel inhibitor is IFNγ.

* * * * *